US007822627B2

(12) United States Patent
St. Martin

(10) Patent No.: US 7,822,627 B2
(45) Date of Patent: Oct. 26, 2010

(54) METHOD AND SYSTEM FOR GENERATING AN ECHOCARDIOGRAM REPORT

(76) Inventor: Edward St. Martin, 1521 Dufossat St., New Orleans, LA (US) 70115

( * ) Notice: Subject to any disclaimer, the term of this patent is extended or adjusted under 35 U.S.C. 154(b) by 1332 days.

(21) Appl. No.: 11/119,679

(22) Filed: May 2, 2005

(65) Prior Publication Data

US 2006/0247545 A1      Nov. 2, 2006

(51) Int. Cl.
G06F 19/00      (2006.01)
G06Q 40/00      (2006.01)
(52) U.S. Cl. ........................................................ 705/3
(58) Field of Classification Search ..................... 705/2, 705/4; 600/437, 450
See application file for complete search history.

(56) References Cited

U.S. PATENT DOCUMENTS

| | | | |
|---|---|---|---|
| 4,528,988 | A | 7/1985 | Wong |
| 5,027,406 | A | 6/1991 | Roberts et al. |
| 5,526,407 | A | 6/1996 | Russell et al. |
| 5,581,460 | A | 12/1996 | Kotake et al. |
| 5,852,819 | A | 12/1998 | Beller |
| 5,911,133 | A | 6/1999 | Soble |
| 6,115,626 | A | 9/2000 | Whayne et al. |
| 6,149,587 | A | 11/2000 | Raines |
| 6,213,945 | B1 | 4/2001 | Tynan |
| 6,346,124 | B1* | 2/2002 | Geiser et al. ................ 600/450 |
| 6,480,186 | B1 | 11/2002 | McCabe et al. |
| 6,490,561 | B1 | 12/2002 | Wilson et al. |
| 6,514,207 | B2 | 2/2003 | Ebadollahi et al. |
| 2001/0041991 | A1 | 11/2001 | Segal et al. |
| 2002/0007117 | A1* | 1/2002 | Ebadollahi et al. .......... 600/437 |
| 2002/0065854 | A1 | 5/2002 | Pressly |

(Continued)

FOREIGN PATENT DOCUMENTS

JP      2000135216      5/2000

(Continued)

OTHER PUBLICATIONS

Text Interpreter Language for Flexible Generation of Patinet Notes and Instructions; Thomas S. Forker, M.D.; AMIA, Inc. 1993.*

*Primary Examiner*—Gerald J. O'Connor
*Assistant Examiner*—John A Pauls
(74) *Attorney, Agent, or Firm*—Juan J. Lizarraga

(57) ABSTRACT

An echocardiogram report generation method and system are disclosed for creating a complete medical report describing an echocardiogram without dictation, transcription or typing. The report is tailored to describe an individual patient and generated in complete grammatically complex sentences in response to the user's input with a text report that is complete and understandable for a primary care physician. The method and system provides the user the parallel options of an anatomical structure approach and a disease-specific approach in order to amplify the description of the echocardiogram in specific areas and give a more meaningful report. The echo report generated by the method and system creates a table of measurements and calculations in compact form, omitting any data fields not used. The method and system guides the user through the various areas of the heart which merit comment on the report and provides clear color coded segments of the heart muscle and provides several heart segment classifications so that the user can use his favored classification scheme. Diagnostic possibilities are provided for inclusion in the report conclusions.

8 Claims, 75 Drawing Sheets

U.S. PATENT DOCUMENTS

| | | |
|---|---|---|
| 2002/0077849 A1 | 6/2002 | Baruch et al. |
| 2002/0131625 A1 | 9/2002 | Vining et al. |
| 2002/0133062 A1 | 9/2002 | Arling et al. |
| 2002/0138731 A1 | 9/2002 | Collamore et al. |
| 2002/0184053 A1 | 12/2002 | Arling |
| 2002/0190980 A1 | 12/2002 | Gerritsen et al. |
| 2002/0198454 A1 * | 12/2002 | Seward et al. ............... 600/437 |
| 2003/0101056 A1 | 5/2003 | Howes |
| 2003/0144886 A1 | 7/2003 | Taira |
| 2003/0177041 A1 | 9/2003 | Millican, III et al. |

FOREIGN PATENT DOCUMENTS

| | | |
|---|---|---|
| WO | WO 0112055 | 4/2001 |

* cited by examiner

SELECT INDICATIONS FOR ECHOCARDIOGRAPHY — A PARTIAL LIST

| VALVE | SIGNS + SX | | AORTA | CONGENITAL | | SYSTEMIC DIS | TUMOR/MASS | |
|---|---|---|---|---|---|---|---|---|
| LV + CM | HBP | AMI + CAD | PERICARDIUM | INFECTION | THROMBOEMB | ARRHYTHMIA | PULMONARY | CRITICAL ILL |

HBP
- Hypertension, malignant 401.0
- Hypertension, benign 401.1
- Hypertension, unspecified 401.9
- Malignant HCVD without CHF 402.00
- Malignant HCVD with CHF 402.01
- Benign HCVD without CHF 402.10
- Benign HCVD with CHF 402.11
- Unspecified HCVD without CHF 402.90
- Unspecified HCVD with CHF 402.91
- Malignant HCVD and renal disease 404.00
- Malignant HCVD and renal disease with CHF 404.01
- Malignant HCVD and renal disease with CRF 404.02
- Malignant HCVD and renal with CHF and CRF 404.03
- Benign HCVD and renal disease 404.10
- Benign HCVD and renal disease with CHF 404.11
- Benign HCVD and renal with CHF and CRF 404.13
- Unspecified HCVD with renal disease 404.90
- Secondary hypertension, malignant renovascular 405.01

PERICARDIUM
- Acute idiopathic pericarditis 420.91
- Acute pericarditis in diseases classified elsewhere 420.0
- Acute pericarditis, unspecified 420.90
- Acute rheumatic pericarditis 391.0
- Adhesive pericarditis 423.1
- Chronic rheumatic pericarditis 393
- Constrictive pericarditis 423.2
- Coxsackie pericarditis 074.21
- Hemopericardium 423.0
- Other and unspecified acute pericarditis 420.99
- Other specified diseases of pericardium 423.8
- Unspecified disease of pericardium 423.9

ARRHYTHMIA
- AV block, complete 426.0
- AV block, unspecified 426.10
- AV block, first degree 426.11
- AV block, Mobitz 2 426.12
- Left bundle branch hemiblock 426.2
- LBBB other 426.3
- RBBB 426.4
- PSVT 427.0
- VT 427.1
- Atrial fibrillation 427.31
- Atrial flutter 427.32
- Ventricular fibrillation 427.41
- Cardiac arrest 427.5
- Sinus node dysfunction 427.81

Select indications from lists above

Cancel    Accept indications and close form

TWENTY FIRST CENTURY ECHOCARDIOGRAM REPORT by Edward St. Martin, M.D.

| RESTRICTIVE CARDIOMYOPATHY | MYXOMA | DIASTOLIC ANALYSIS | CARDIAC SOURCE OF EMBOLI |
| MYOCARDIAL INFARCTION | HYPERTROPHIC CARDIOMYOPATHY | DILATED CARDIOMYOPATHY | INFECTIVE ENDOCARDITIS | COMPARISON TO PRIOR ECHO |

AORTIC DISSECTION

UNDERLYING PATHOLOGY
- generalized aortic dilatation
- annuloaortic ectasia
- bicuspid aortic valve
- hypertensive heart disease with LVH

DEBAKEY CLASSIFICATION
- no comment
- Type I — proximal and distal
- Type II — proximal
- Type III — distal

ANATOMIC FEATURES
- M-mode dissection flap
- 2-D dissection flap in ascending aorta
- 2-D dissection flap in descending aorta
- compression of true lumen
- visible entry point into false lumen
- widening of anterior aortic wall
- widening of posterior aortic wall
- "smoke" in false lumen
- thrombus in false lumen
- compression of left atrium

FUNCTIONAL FEATURES
- aortic regurgitation
- pericardial effusion
- brisk color flow in false lumen

COMPLICATIONS
- aortic regurgitation
- pericardial effusion
- pericardial tamponade
- pleural effusion
- mediastinal hematoma
- myocardial infarction
- aortic leaflet dehiscence Enable all controls    Close

TWENTYFIRST CENTURY ECHOCARDIOGRAM REPORT by Edward St. Martin, M.D.

| MYOCARDIAL INFARCTION | HYPERTROPIC CARDIOMYOPATHY | DILATED CARDIOMYOPATHY | INFECTIVE ENDOCARDITIS | AORTIC DISSECTION |
| RESTRICTIVE CARDIOMYOPATHY | MYXOMA | DIASTOLIC ANALYSIS | CARDIAC SOURCE OF EMBOLI | COMPARISON TO PRIOR ECHO |

1132

LEFT ATRIUM
- ☑ flat EF slope of mitral valve.
- ☐ tumor echoes behind ALMV
- ☐ tumor descent time
- ☑ tumor echoes in LA in systole
- ☑ visible mobile tumor on 2-D

RIGHT ATRIUM
- ☐ flat EF slope of tricuspid valve
- ☐ tumor echoes in RV in diastole
- ☐ tumor descent time
- ☐ tumor echoes in RA in systole
- ☐ visible mobile tumor on 2-D

LEFT VENTRICLE
- ☐ globular demarcated mass
- ☐ attached to free wall
- ☐ in apex
- ☐ attached to septum
- ☐ single lesion
- ☐ multiple lesions

RIGHT VENTRICLE
- ☐ globular demarcated mass
- ☐ attached to free wall
- ☐ in apex
- ☐ attached to septum
- ☐ single lesion
- ☐ multiple lesions

1131

- ☑ narrow base along the fossa ovalis
- ☐ broad base
- ☐ calcification
- ☐ lucent areas

- ☐ narrow base along the fossa ovalis
- ☐ broad base
- ☐ calcification
- ☐ lucent areas

- ☐ rounded
- ☐ bilobular
- ☐ multilobular

- ☐ rounded
- ☐ bilobular
- ☐ multilobular

1133

BILATERAL ATRIAL MYXOMAS
- ☐ bilateral tumors along fossa ovalis
- ☐ equal bilaterally

- ☐ left atrial myxoma larger
- ☐ right atrial myxoma larger

There is a mass consistent with a left atrial myxoma. The images show a flat mitral EF slope, tumor echoes in the left atrium in systole and a typical rounded demarcated mobile left atrial mass on the 2-D images. The attachment is narrow-based, along the limbus of the fossa ovalis.

1134

Enable all controls                                                                                    Close

FIG. 119

TWENTY FIRST CENTURY [ECHOCARDIOGRAM REPORT] by Edward St. Martin, M.D.

| RESTRICTIVE CARDIOMYOPATHY | MYXOMA | DIASTOLIC ANALYSIS | CARDIAC SOURCE OF EMBOLI | COMPARISON TO PRIOR ECHO |
| --- | --- | --- | --- | --- |
| MYOCARDIAL INFARCTION | HYPERTROPHIC CARDIOMYOPATHY | DILATED CARDIOMYOPATHY | INFECTIVE ENDOCARDITIS | AORTIC DISSECTION |

ANATOMIC

- ☐ asymmetric septal hypertrophy
- ☐ basal asymmetric septal hypertrophy
- ☐ mid-septal asymmetric septal hypertrophy
- ☐ apical asymmetric septal hypertrophy
- ☐ apical hypertrophy
- ☐ midventricular hypertrophy
- ☐ lateral free wall hypertrophy
- ☐ diffuse left ventricular hypertrophy
- ☐ a small hyperkinetic LV
- ☐ left atrial enlargement

FUNCTIONAL

- ☐ SAM of the ALMV
- ☐ midsystolic closure of the aortic valve
- ☐ decreased septal motion
- ☐ hyperkinesis of the LVPW
- ☐ flat mitral EF slope
- ☐ contact of MV E point with septum
- ☐ mitral regurgitation
- ☐ LV systolic cavity obliteration
- ☐ Doppler turbulence in LVOT

IHSS

- ☑ asymmetric septal hypertrophy
- ☑ SAM of the ALMV
- ☑ LA enlargement
- ☐ midsystolic aortic valve closure
- ☐ dagger-shaped LVOT Doppler
- ☐ LVOT Doppler turbulence Features consistent with IHSS are asymmetric septal hypertrophy, SAM of the ALMV and LA enlargement.

Enable all controls

Close

FIG. 11h

FIG. 11i (Screen shown rotated 90°. Visible labels and elements:)

TWENTY FIRST CENTURY ECHOCARDIOGRAM REPORT by Edward St. Martin, M.D.

Tabs: RESTRICTIVE CARDIOMYOPATHY | MYXOMA | DIASTOLIC ANALYSIS | COMPARISON TO PRIOR ECHO | MYOCARDIAL INFARCTION | HYPERTROPIC CARDIOMYOPATHY | DILATED CARDIOMYOPATHY | CARDIAC SOURCE OF EMBOLI | INFECTIVE ENDOCARDITIS | AORTIC DISSECTION 1140 — (tab pointer to DILATED CARDIOMYOPATHY)

1139 — ANATOMIC
- ☑ four chamber dilatation
- ☐ LVH with dilatation
- ☑ globular LV shape
- ☑ spontaneous intracavitary echo contrast
- ☐ left ventricular dilatation
- ☐ left atrial dilatation
- ☐ mural thrombus 1141 — FUNCTIONAL
- ☑ mitral regurgitation
- ☐ tricuspid regurgitation
- ☐ pulmonic regurgitation
- ☐ increased PAP
- ☐ decreased mitral annular excursion OTHER FEATURES
- ☐ signs of LV systolic dysfunction
- ☐ combined systolic and diastolic LV dysfunction
- ☐ signs of LV diastolic dysfunction 1142 — Anatomic features consistent with dilated cardiomyopathy are four chamber dilatation, globular LV shape and spontaneous intracavitary echo contrast.

Enable all controls | Close

ECHOCARDIOGRAM REPORT  /— 1201
XYZ CARDIOLOGY CENTER

| Patient: Numbers, Test | Date: 5-1-04 |
|---|---|

Ordered by: Jones  Location: Emergency Room  Record: 1234  Study: 0001  Age: 45  BP: 120/80  Ht: 73 inches  Wt: 180 lbs.
Indication: Unspecified disease of pericardium 423.9

M-mode and 2-D echoes and Doppler studies with color flow mapping were performed. Good images were obtained.

The rhythm is sinus. The left ventricle is normal in diameter and contracts in an overall normal manner. There is no wall motion abnormality. The walls of the left ventricle are generally normal in thickness. The calculated ejection fraction is 50%. The mitral inflow Doppler shows a low E wave, tall A wave and long deceleration time indicating abormal relaxation. The left atrium is mildly dilated.

The right ventricle is normal in dimension, with normal systolic contraction and normal wall thickness. Right atrial size is normal.

The leaflets of the mitral valve appear normal. Neither mitral stenosis nor insufficiency is seen.

Aortic valve images show moderate sclerotic changes. Mild aortic stenosis is present. Color flow Doppler shows trivial aortic regurgitation.

The tricuspid valve shows no abnormality of morphology or motion. Color flow Doppler shows 1+ tricuspid regurgitation. Right ventricular systolic pressure is mildly elevated at 45mm. IVC diameter and respiratory change suggest normal right atrial pressure. The pulmonic valve is not clearly visible. There is no Doppler evidence of pulmonic regurgitation.

There is no pericardial thickening or effusion. There is no visible vegetation on any valve. There is uniform dilatation of the ascending aorta. No masses, thrombi, or foreign bodies are seen.

| LVD | LVS | LV EF | LVPW | Septum | LA diam | Ao Diam | AoValve | TR vel | RVSP |
|---|---|---|---|---|---|---|---|---|---|
| 55mm | 44mm | 50% | 11mm | 9 mm | 40mm | 35mm | 18mm | 2.8M/S | 45mm |

| Ao Vel | AoV Mn Grd | AoV Pk Grd | AV Area | AR T1/2 | MV E | MV A | MV E:A | IVC diam | IVC resp |
|---|---|---|---|---|---|---|---|---|---|
| 2.4M/S | 34mm | 45mm | 1.5cm | 555ms | 135cm | 67 cm | 2.01 | 25mm | 70% |

| Veg Dia | RV | MV A dur | PV AR | MV DT | MV Ea | PV AR Dur | Vp |
|---|---|---|---|---|---|---|---|
| 9 mm | 23mm | 50ms | 40ms | 300ms | 10cm/S | 40 ms | 45cm |

CONCLUSIONS:

1+ tricuspid regurgitation  left atrial dilatation
aortic stenosis 424.1  LV diastolic dysfunction 428.9
calculated LV EF 50  mildly elevated RVSP 416.8
dilated ascending aorta  sclerotic aortic valve Edward St. Martin

METHOD AND SYSTEM FOR GENERATING AN ECHOCARDIOGRAM REPORT

FIELD OF THE INVENTION

The present invention relates to a computer software product for generation of a medical report. More particularly, the present invention is related to the generation of a medical report describing an echocardiogram.

BACKGROUND OF THE INVENTION

The echocardiogram is a well-known diagnostic procedure that uses ultrasound to take moving pictures of the heart. It is estimated that there are over ten million echocardiograms performed annually in the United States. Among other things, the echocardiogram allows measurements of the chambers of the heart and the appearance and motion of the heart. A large amount of detailed information must be reviewed and evaluated by the interpreting physician, sometimes called an echocardiographer. Echocardiogram reports (hereinafter "echo reports") are typically arranged by the different anatomical structures in the heart such as chambers or valves. On the basis of this anatomical structure approach, the echocardiographer may identify a particular condition. The echo report is then dictated or hand-written before being typed and returned to the interpreting physician for review and signature. Only then is the echo report, which must be complete and understandable, sent to the primary care physician who ordered the report. Aside from the loss of time and money in this process, the echocardiographer must review and approve a report without the benefit of the echocardiogram images in front of him for review.

In addition to the large amount of information that must be reviewed and evaluated by the echocardiographer, there are differences in opinion among echocardiographers as to the number of segments appropriate for classification of the heart muscle. For example, some use a sixteen-segment classification and others use a fifteen-segment classification.

Aside from differences in preferred classification of the heart muscle segments, the number of measurements actually taken on a particular patient is usually less than the possible number of measurements. It is also true that some areas of the heart cannot be visualized well in every patient. What this means is that many data fields may be empty and make a report longer than necessary and require additional time on the part of the evaluation physician to dictate an explanation for the missing items.

Although there have been attempts to generate echo reports by computer software, there is a need for a method or system that allows the user, having identified a specific condition by an anatomical based approach to cross reference and compare other options by a condition or disease based approach. Likewise, there is a need for a method or system which gives the user the ability to create an echo report with minimal interaction and to edit the elements of the report as selections are made or to generate a report in grammatically correct sentences that is complete and understandable for the primary care physician.

What is also needed is a method or system that can quickly and easily guide the user through the various areas of the heart with color-coded diagrams of the various segments of the heart which merit comment on the report. Likewise, what is needed is a method or system that can be easily installed in a doctor's personal computer ("PC") or laptop and is suitable for both general cardiologists and echocardiographers.

SUMMARY OF THE INVENTION

The present invention is directed to a computer readable storage method and system allowing a physician to create a complete and well-organized medical report describing an echocardiogram (an echo report) without dictation, transcription or typing. The inventive method and system quickly and easily guides the doctor through the various areas of the heart which merit comment on the echo report. The inventive method and system allows the physician to create an echo report with minimal interaction and without the need to enter any measurements. However, any measurements entered by the technician can be corrected by the physician if needed.

The inventive method and system provides clear color-coded diagrams of the various named segments of the heart muscle. As there is a lack of unanimity among echocardiographers as to whether a fifteen-segment classification or a sixteen-segment classification is preferable, this invention provides each, as well as a third classification so the user can choose whichever classification scheme is desired.

In addition to the standard anatomical-based approach by which traditional echo reports are structured, the inventive method and system provides a parallel disease or condition specific section with a separate set of tabbed pages or interfaces each devoted to a specific disease entity. Thus the user, having identified the presence of a certain condition by a standard anatomical-based approach, may, if desired, shift to a specific disease-oriented page and be presented with a set of options reminding the user of all of the various possible echo findings in that disease. This gives the user the option to amplify the description of the echo in certain specific areas and give a more meaningful echo report The inventive method and system provides a list of normal values for certain measurements of artificial heart valve functions, important to the interpretation of artificial heart valve echo studies, and also provides diagrammatic prompts to aid in the interpretation of certain Doppler echo measurements that are infrequently made but important in certain cases.

The inventive method and system collects diagnostic possibilities based on the descriptive choices made by the user and presents a list of these diagnoses, which list can be amended from a predetermined list of common cardiac conditions or with free text additions. ICD-9 codes for each diagnosis are added automatically, eliminating the time consuming and expensive stage of coding the diagnosis.

The invention is compatible with a Windows® based operating system and can be installed and used on a PC in a physician's office or in a hospital. The invention operates by controlling Microsoft Word® as its word processing output and uses Microsoft Access® as a database. The invention will also operate with Windows® 98SE and Windows® XP. It can utilize Word® 2000 or later and likewise can utilize Access® 2000 or later.

Although mainly intended for use in a PC, the invention is easily adaptable to a larger echocardiogram-processing package or can be built into an echocardiogram machine.

The invention provides graphic user interfaces (herein referred to as "screen pages" or "screens") for use with any mouse-type pointing device or equally effective in a touch-screen computer, totally eliminating any mouse motion. The various sections of the echo report are shown "live" on the graphic user interface in the form of text in text boxes as the user's input occurs. This input is editable by the user at any stage if there are any nuances that need to be recorded. At the end of the user interface is another blank text box for additional free-text comments. In addition, a user can customize a number of check boxes with statements unique to that user which will be displayed each time the user initiates or logs in to the inventive system.

It is an object of this invention that the echo report includes a table of measurements and calculations on an individual patient, which table shall be compact and only include those measurements taken on that patient and omitting any unused data fields. In practice each patient will normally have only five to ten measurements out of a possible fifty.

It is an object of this invention that an echo report to describe an individual patient is created in complete sentences including complex sentences grammatically tailored by the software in response to the user's input.

The invention will create a final echo report instantly, allow its review immediately on the computer screen, and allow the immediate finalization of the echo report either with an electronic signature or an on-the-spot hard copy. The final product will be an ordinary Word® document, which can be sent electronically to a patient's chart or referring doctor's office.

It is therefore an object of this invention to provide a computer-implemented method of generating a medical report from an echocardiogram for a patient, comprising the steps of: creating at least one database comprising echocardiogram measurements for at least one patient; providing a user with a prompting graphical user interface to log in and gain access to said database and the echocardiogram measurements for a patient; providing the user with a start-up graphical user interface for display of echocardiogram measurements for the patient, said start-up graphical user interface having a plurality of tabbed anatomical-based graphical user interfaces pertaining to specific anatomical parts of a human heart for entry of a diagnosis by the user pertaining to any of said anatomical parts of the human heart based upon the echocardiogram measurements for the patient available in said data base; providing the user with a plurality of disease-based graphical user interfaces pertaining to disease states of the human heart accessible from the anatomical-based graphical user interfaces to assist the user in the entry of a diagnosis by the user pertaining to any of the specific anatomical parts of the human heart based upon the echocardiogram measurements for the patient available in said data base; generating complete grammatically correct sentences in response to the entry of diagnosis by the user pertaining to any of the specific anatomical parts of the human heart based upon the echocardiogram measurements for the patient available in said data base; generating complete grammatically correct sentences in response to the entry of diagnosis by the user pertaining to any of the disease states of the human heart based upon the echocardiogram measurements for the patient available in said data base; providing the user with a graphical user interface to create a medical report in complete grammatically correct sentences based on the entry of diagnoses by the user; and generating a medical report in complete grammatically correct sentences based on the entry of diagnoses by the user.

It is a further object of this invention to provide a computer-readable storage medium for use with a graphics display device bearing program code for instructing a computer to perform a method of generating a medical report from an echocardiogram for a patient, said method comprising the steps of: comprising the steps of: creating at least one database comprising echocardiogram measurements for at least one patient; providing a user with a prompting graphical user interface to log in and gain access to said database and the echocardiogram measurements for a patient; providing the user with a start-up graphical user interface for display of echocardiogram measurements for the patient, said start-up graphical user interface having a plurality of tabbed anatomical-based graphical user interfaces pertaining to specific anatomical parts of a human heart for entry of a diagnosis by the user pertaining to any of said anatomical parts of the human heart based upon the echocardiogram measurements for the patient available in said data base; providing the user with a plurality of disease-based graphical user interfaces pertaining to disease states of the human heart accessible from the anatomical-based graphical user interfaces to assist the user in the entry of a diagnosis by the user pertaining to any of the specific anatomical parts of the human heart based upon the echocardiogram measurements for the patient available in said data base; generating complete grammatically correct sentences in response to the entry of diagnosis by the user pertaining to any of the specific anatomical parts of the human heart based upon the echocardiogram measurements for the patient available in said data base; generating complete grammatically correct sentences in response to the entry of diagnosis by the user pertaining to-any of the disease states of the human heart based upon the echocardiogram measurements for the patient available in said data base; providing the user with a graphical user interface to create a medical report in complete grammatically correct sentences based on the entry of diagnoses by the user; and generating a medical report in complete grammatically correct sentences based on the entry of diagnoses by the user.

It is a further object of this invention that the user be provided with graphical user interfaces pertaining to specific anatomical parts of a human heart, comprising a graphical user interface for the aortic valve, a graphical user interface for the left ventricle and left atrium, a graphical user interface for the right ventricle and right atrium, a graphical user interface for the mitral valve, a graphical user interface for the tricuspid valve, the pulmonic valve and the inferior vena cava, a graphical user interface for the pericardium, a graphical user interface for the aorta, thrombus and foreign bodies, a graphical user interface for vegetations, a graphical user interface for atrial septal defect, patent foramen ovale and ventricular septal defect, a graphical user interface for M-mode and Doppler left ventricular signs; a graphical user interface for abnormal septal motion, a graphical user interface for prosthetic valves, and a graphical user interface for segmental wall motion. It is not intended that this invention be limited to this listing of anatomical parts of the human heart.

It is a further object of this invention that the user be provided with graphical user interfaces pertaining to disease states of the human heart comprising a graphical user interface for cardiac source of emboli, a graphical user interface for diastolic analysis, a graphical user interface for myxoma, a graphical user interface for restrictive cardiomyopathy, a graphical user interface for aortic dissection, a graphical user interface for infective endocarditis, a graphical user interface for dilated cardiomyopathy, a graphical user interface for hypertropic cardiomyopathy, and a graphical user interface for myocardial infarction. It is not intended that this invention be limited to these disease states.

BRIEF DESCRIPTION OF THE DRAWINGS

FIG. 3 is the start-up page of the report form screen page.
FIG. 4 is a search form screen page.
FIG. 5 is a new patient database form.
FIG. 6 is a technician's form screen page for display of data.
FIGS. 7*a* through 7*c* are maintenance form screen pages.

FIG. 8 is an "Omit Any Uninterpretable Data" box displayed on the start-up screen page.

Figure 9A:
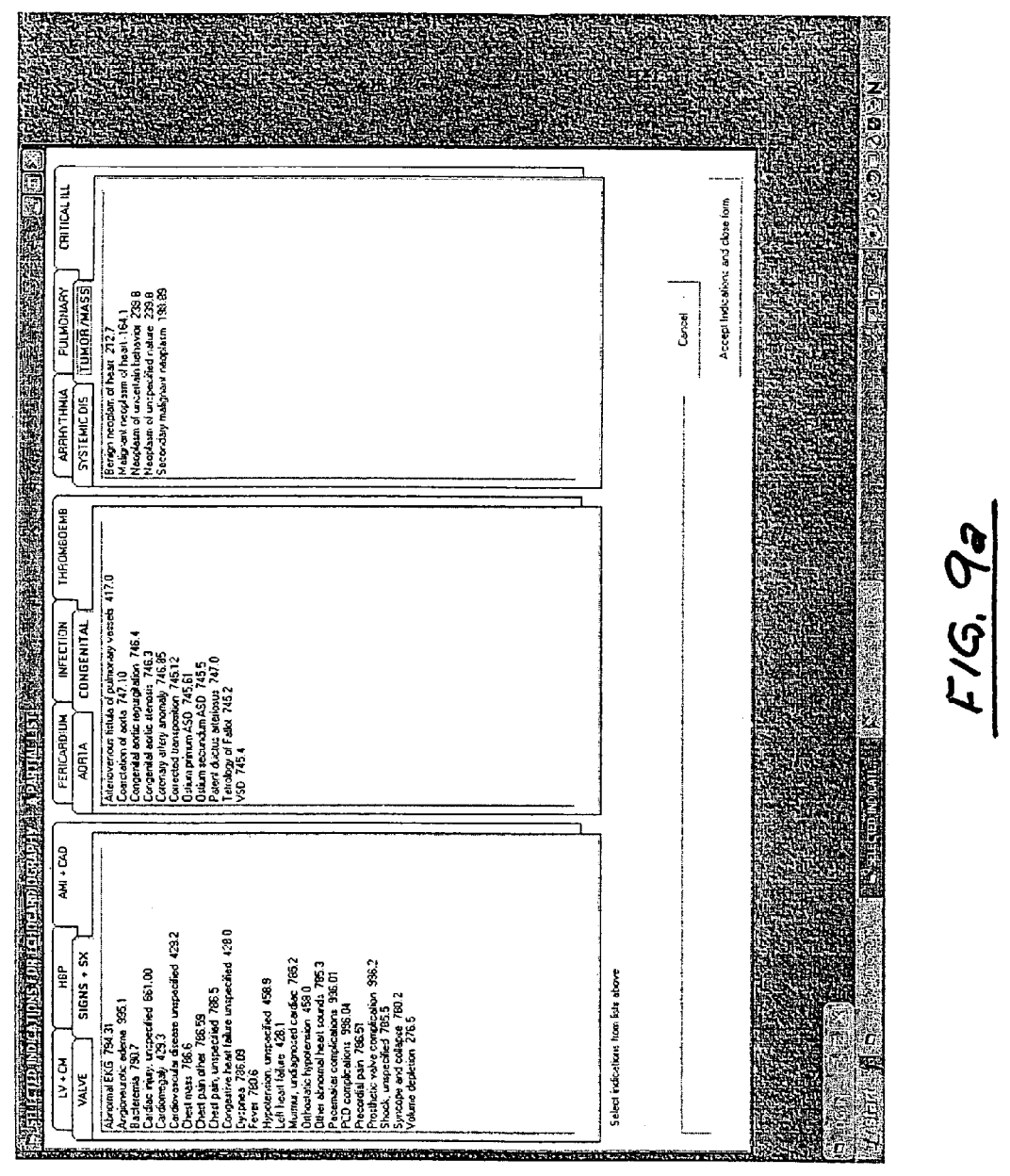
Figure 9B:
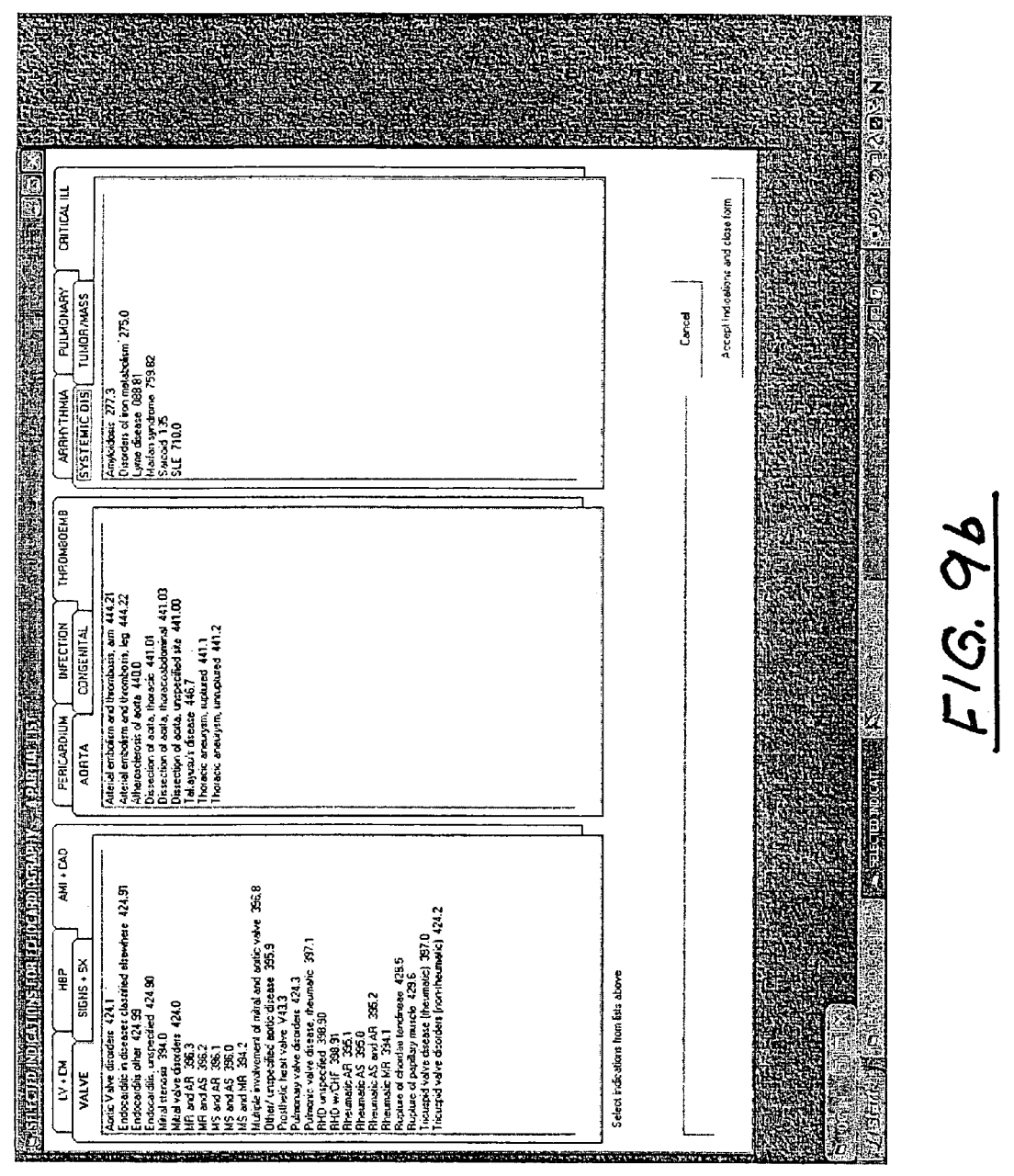
Figure 9C:
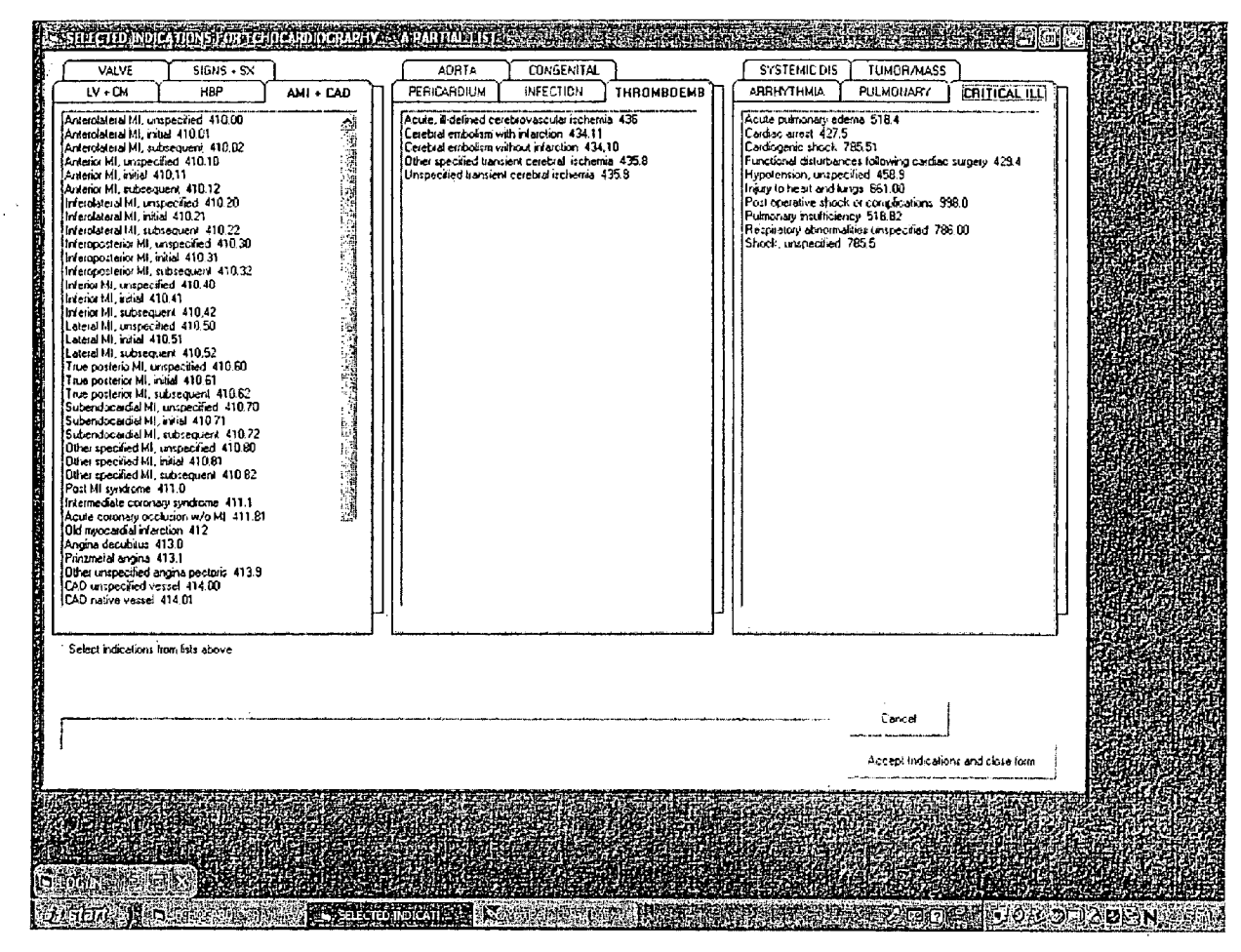
Figure 9E:
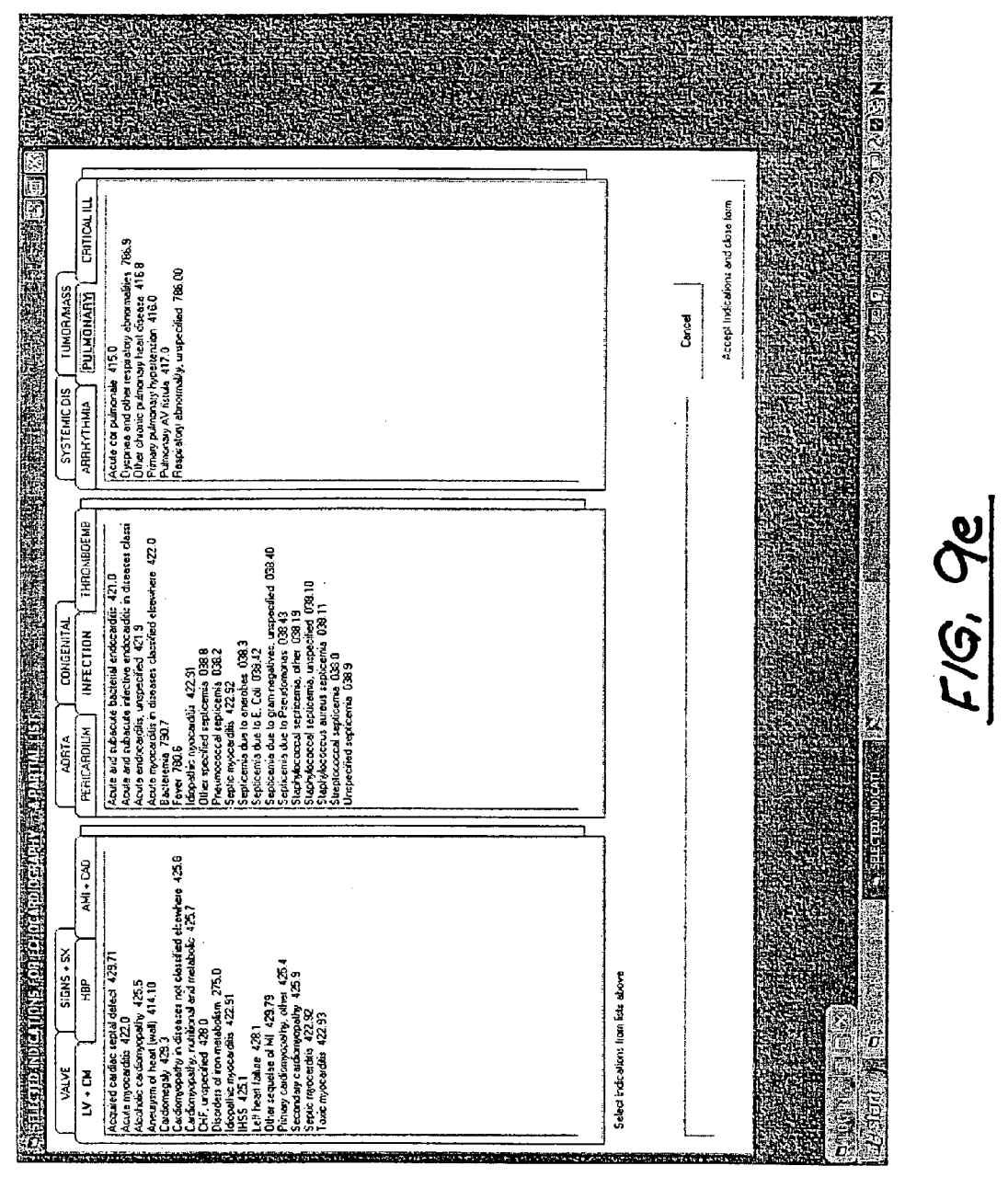

FIGS. 9a through 9e are tabbed screen pages of selected indications for echocardiography.

FIGS. 10aa through 10ab are the conclusion screen pages opened from the start-up page.

FIGS. 11a through 11k are the tabbed individual condition screen pages opened from the start-up page.

FIG. 12 is a completed exemplary echo report generated by the inventive computer-implemented method and computer-readable storage medium.

FIGS. 14a, 14b, 15a, 15b, 15c, 15d, 15e, 16, 17a, 17b, 17c, 17d, 18a, 18b, 18c, 18d, 18e, 18f, and 19 are tabbed anatomical-based screen pages showing the generation of complete grammatically complex sentences in response to the user's input with illustration of different inputs and the resulting sentences.

DETAILED DESCRIPTION OF THE INVENTION

Figure 1:
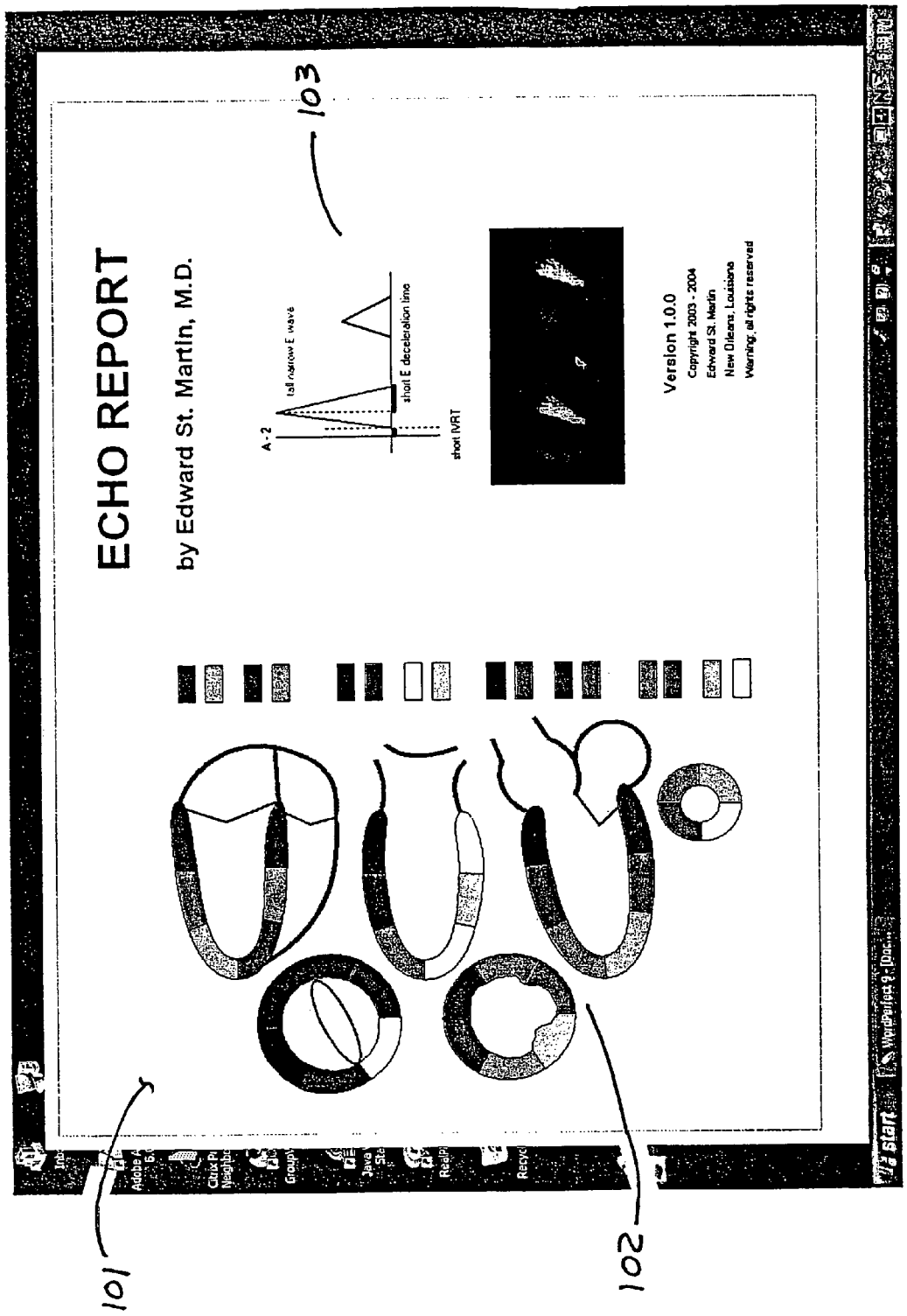
FIG. 1 is a splash screen introductory page.

FIG. 1 is a splash screen introductory page 101 with a graphic color representation 102 of sixteen segment classification of the heart muscle and a graphic representation 103 of a mitral diastolic Doppler.

Figure 2:
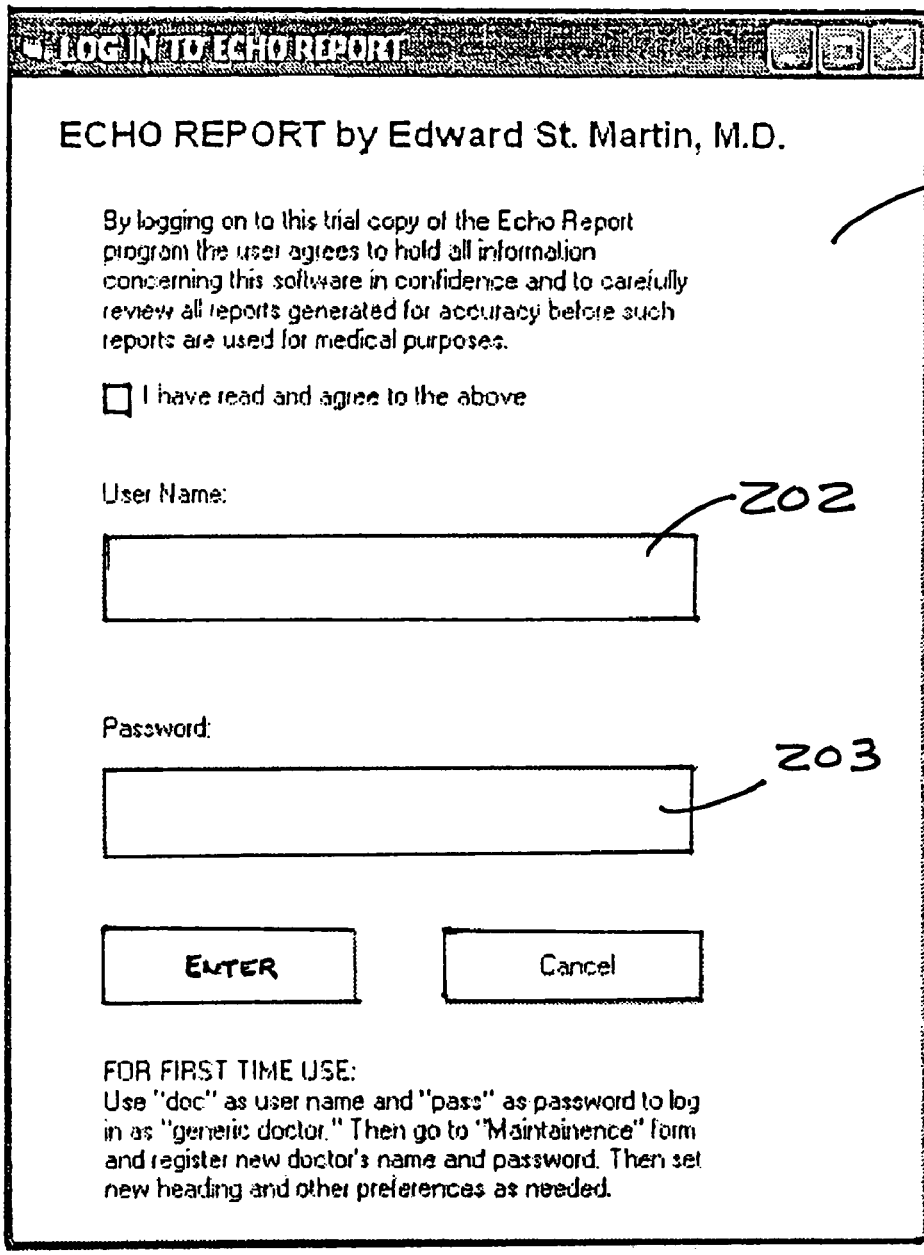
FIG. 2 is a log-in form screen page.

FIG. 2 is a log-in form screen page 201 for the using physician to enter a name into the User Name box 202 and a password into Password box 203 and engage an Enter button 204 to continue the inventive computer-implemented method and computer-readable storage medium for generating a medical report for a patient from an echocardiogram.

Figure 3:
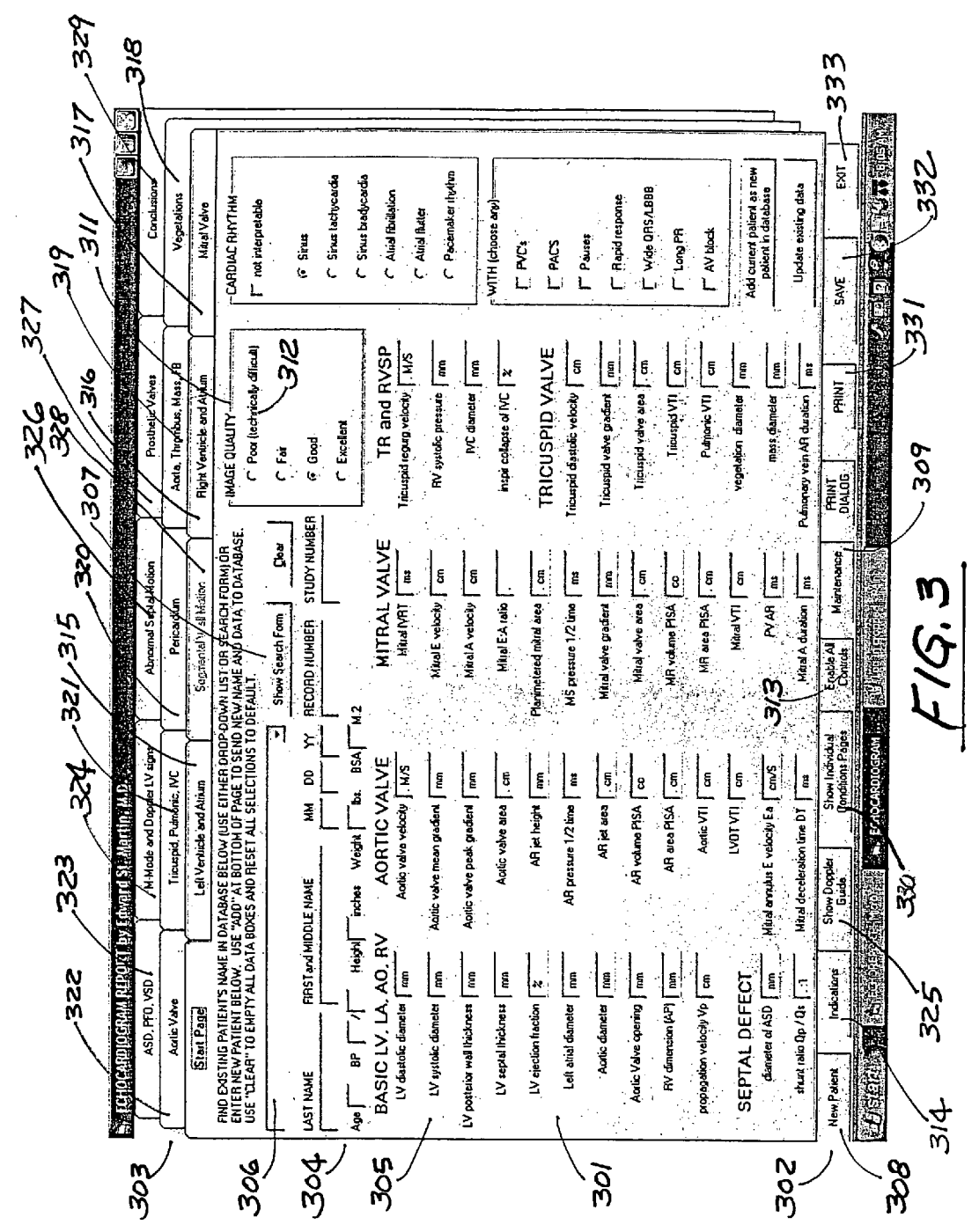

FIG. 3 is the start-up screen page 301 for opening the inventive computer-implemented method and computer-readable storage medium. There are command buttons 302 at the bottom of start-up screen page 301 for performing various functions and there are tabs 303 at the top of the start-up screen page 301 which allows the user to select different areas of the heart for comment. These buttons and tabs are illustrative examples and it is not intended that the present invention be limited to these examples nor to the location of these examples on the start-up screen page 301.

Figure 4:
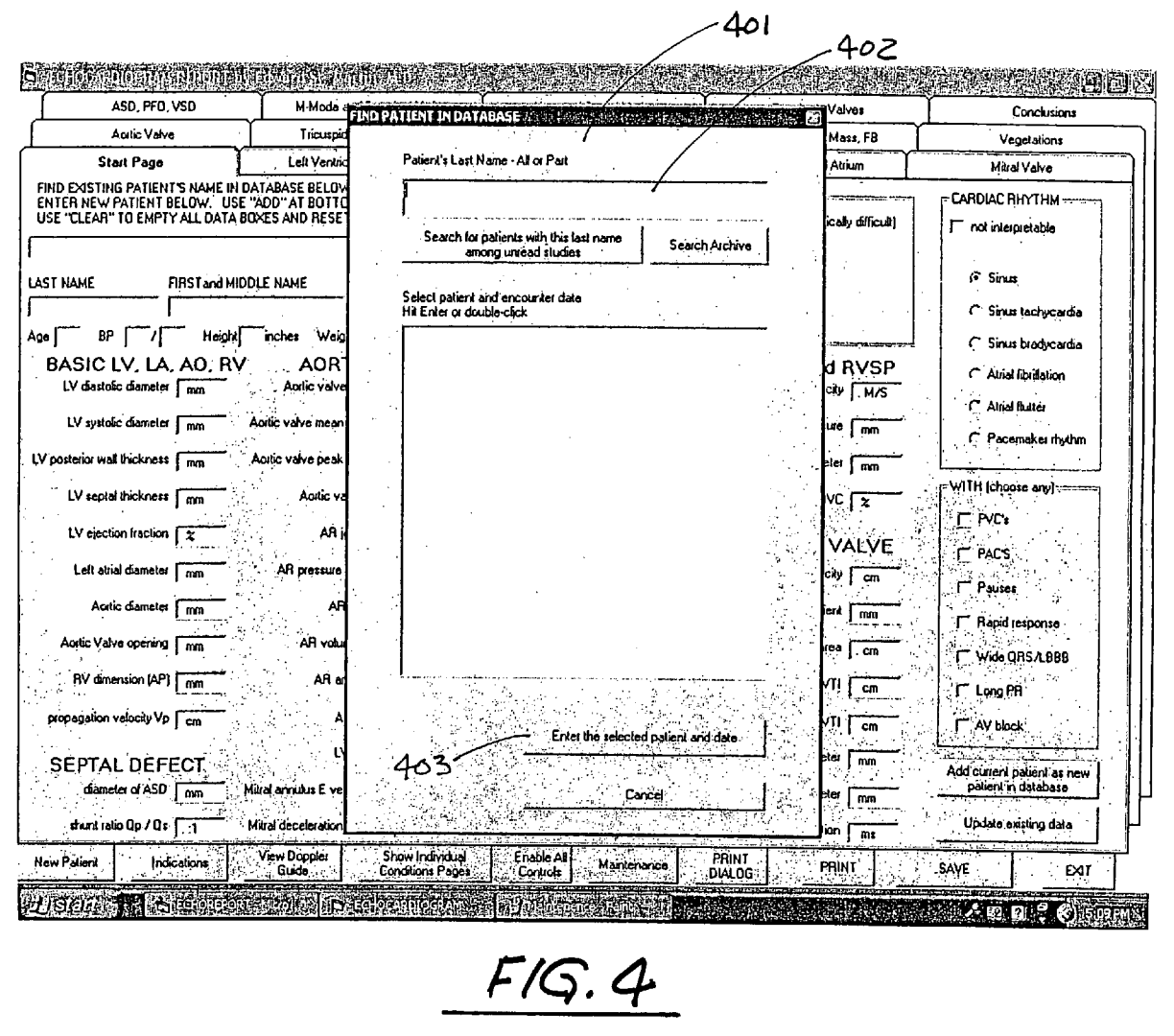
Figure 5:
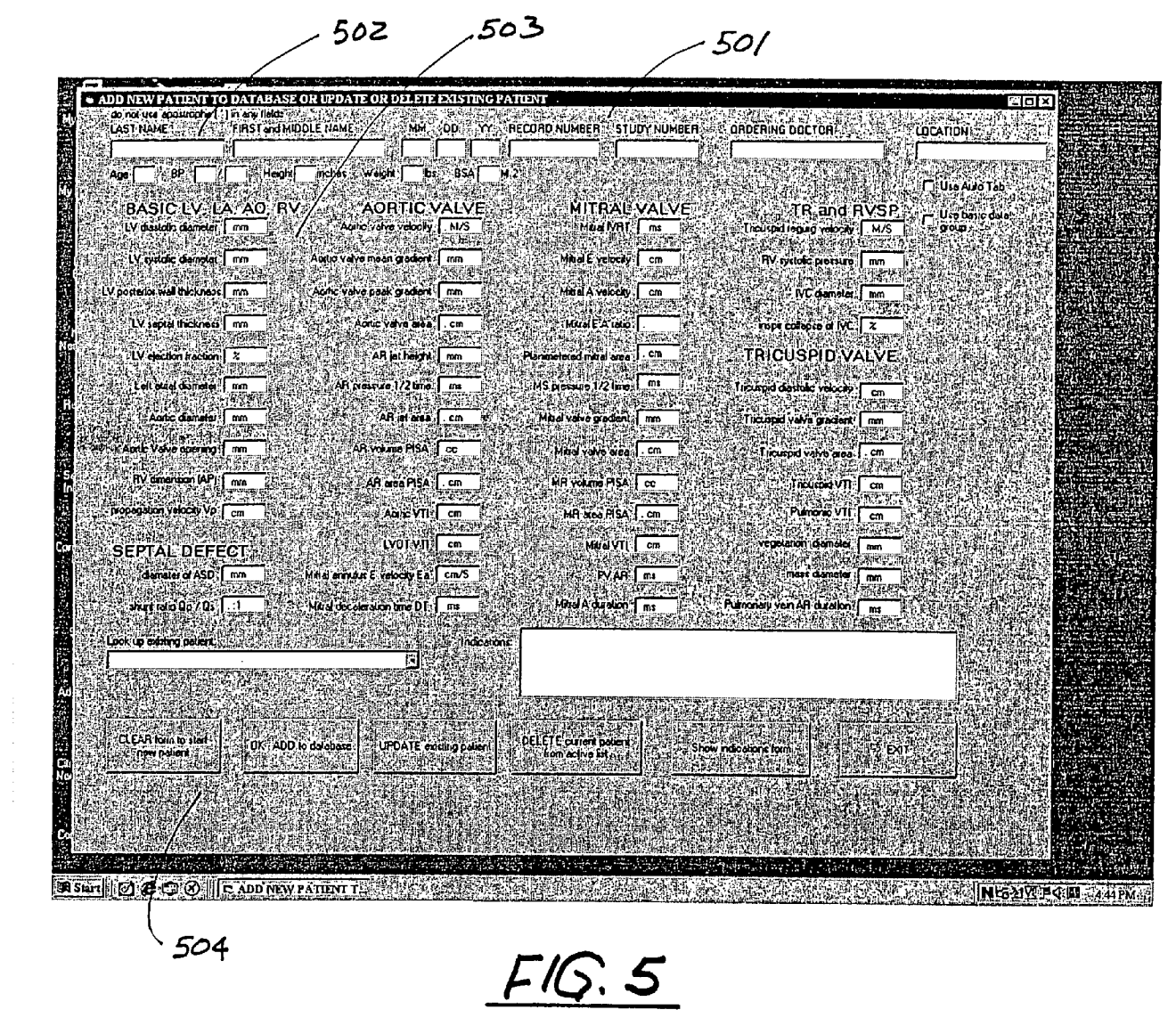

Start-up screen page 301 also contains boxes 304 for entry of patient name and data, as well as boxes 305 for entry of all measurements taken in an echocardiogram test for that patient. As shown in FIG. 3, start-up screen 301 allows the user to access a database and find an existing patient through a drop-down box 306, or by a Show Search Form button 307 which opens a search form screen page 401 as shown in FIG. 4. Search form screen page 401 has a box 402 for the patient's name and a button 403 for entry of the patient's data from the database. By use of the drop-down box 306 or the search form screen page 401, the data for an existing patient can be accessed and automatically entered into boxes 304 and 305. For a new patient, the user can depress the New Patient button 308 which will open a new patient database form 501 illustrated in FIG. 5, which contains boxes 502 for entry of patient name and data, as well as boxes 503 for entry of all measurements taken in an echocardiogram test for that patient. Also included on new patient database form 501 are command buttons 504 to perform various functions with the patient data. As indicated on form 501, the form may be used to add new patient data to the. database, update that data or delete an existing patient from the database.

Figure 6:
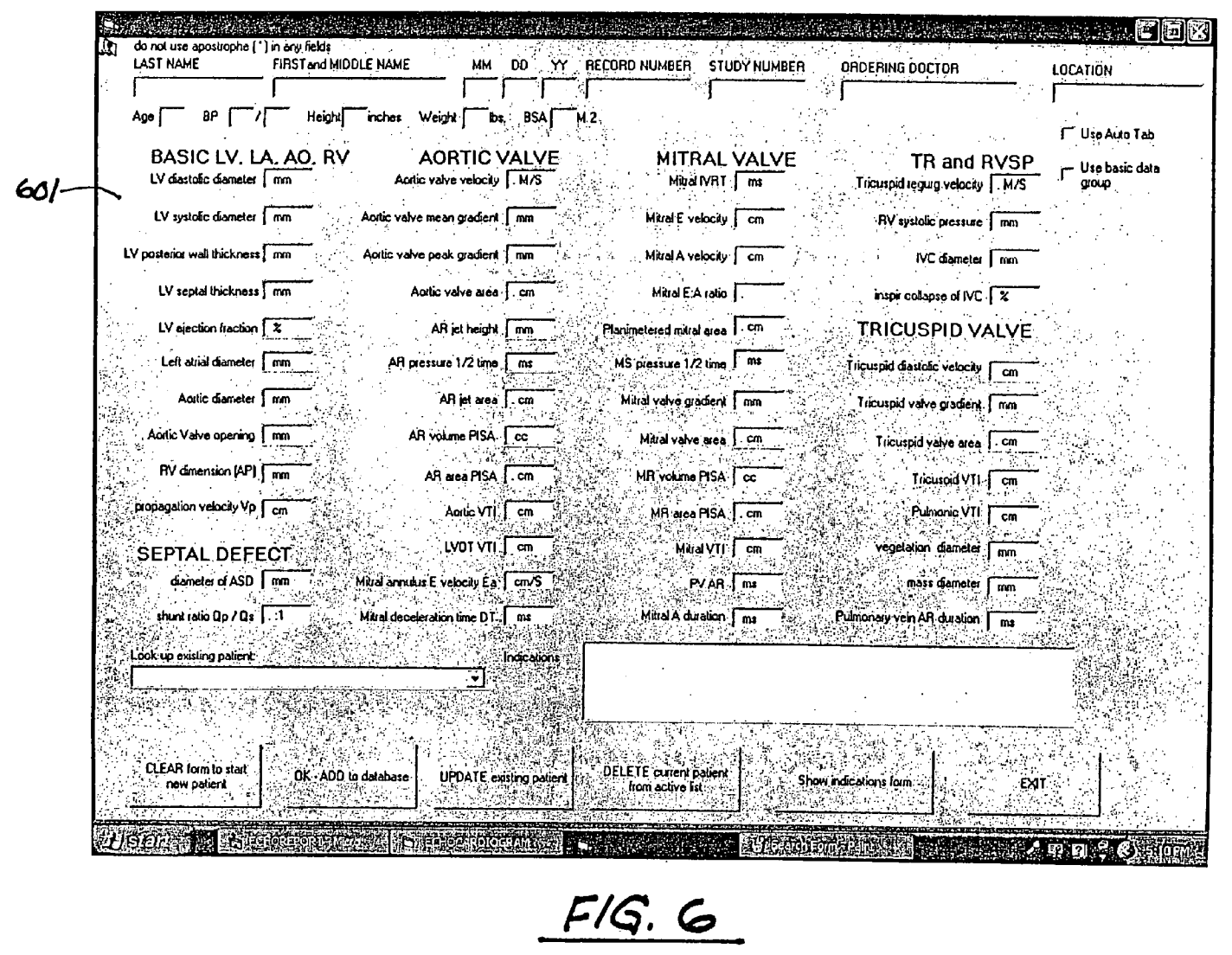

FIG. 6 is a technician's form screen page 601 used by an echocardiogram technician to enter data and measurements from an echocardiogram for a patient. This form screen page 601 is identical to the new patient database form screen page 501 and the information on screen page 601 is the source of information which may be ultimately entered for a new patient by using form screen page 501.

All measurements visible in boxes 305 on the start-up screen page 301 are brought forward to each screen page as needed.

Figure 7A:
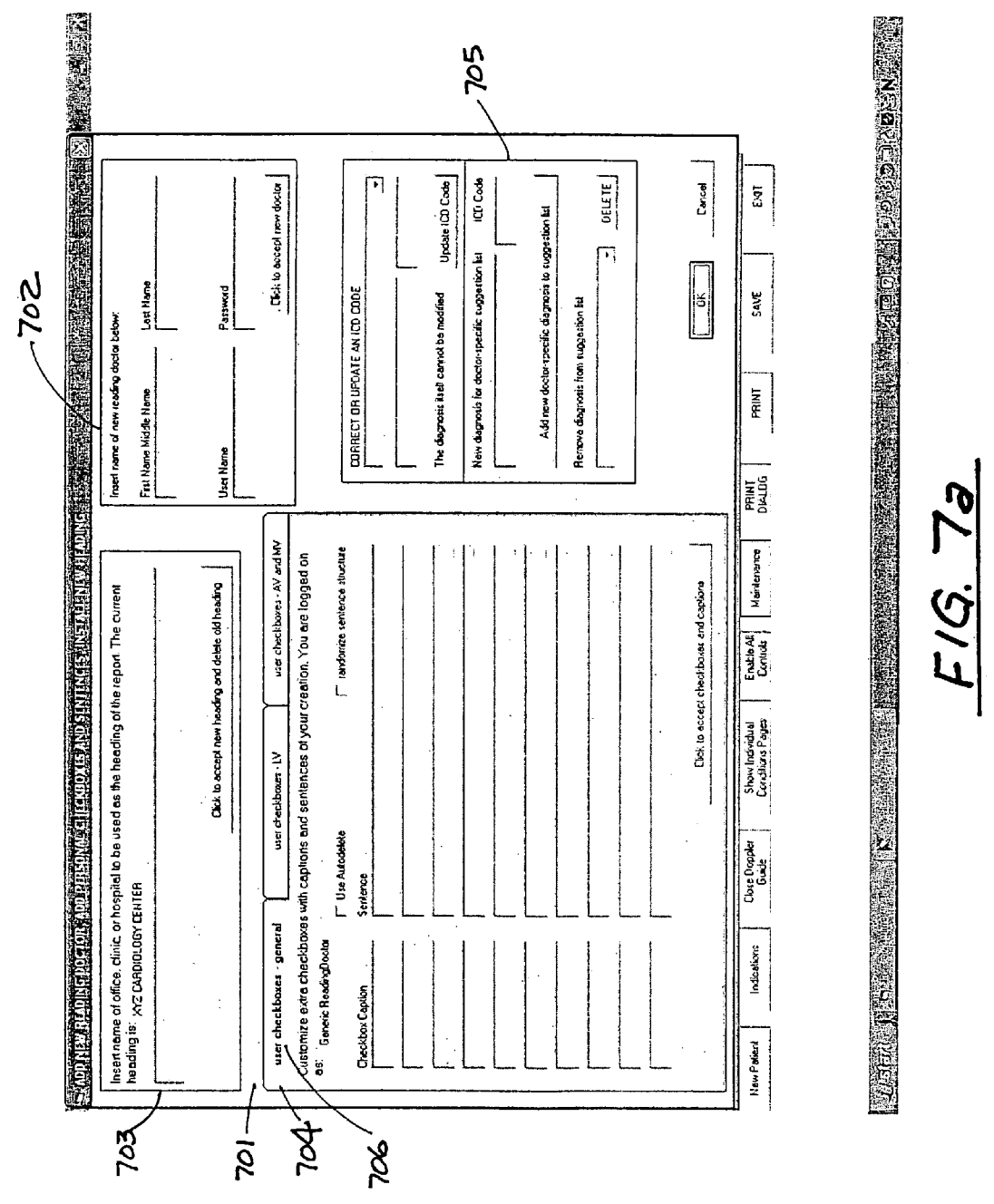
Figure 7B:
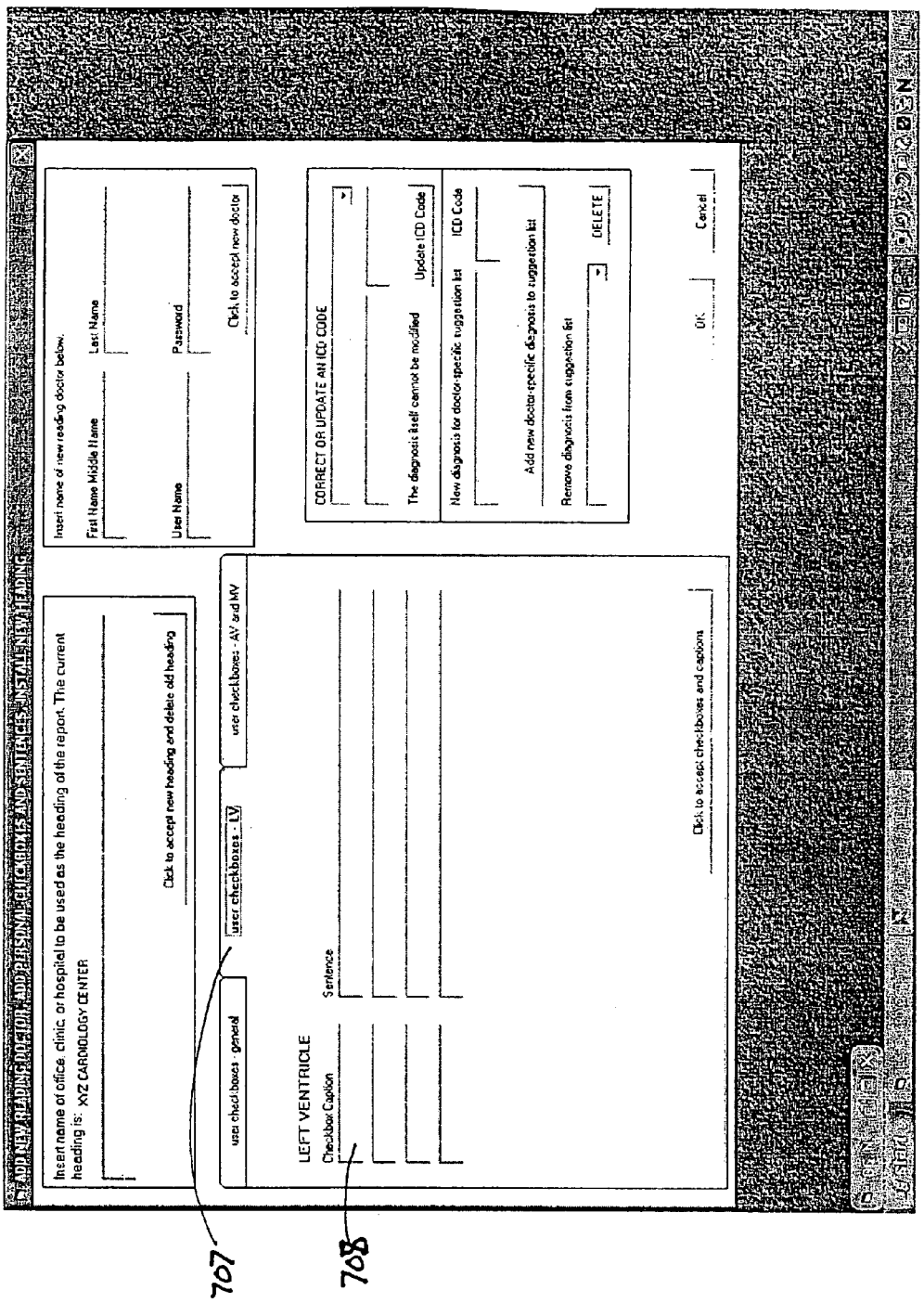
Figure 7C:
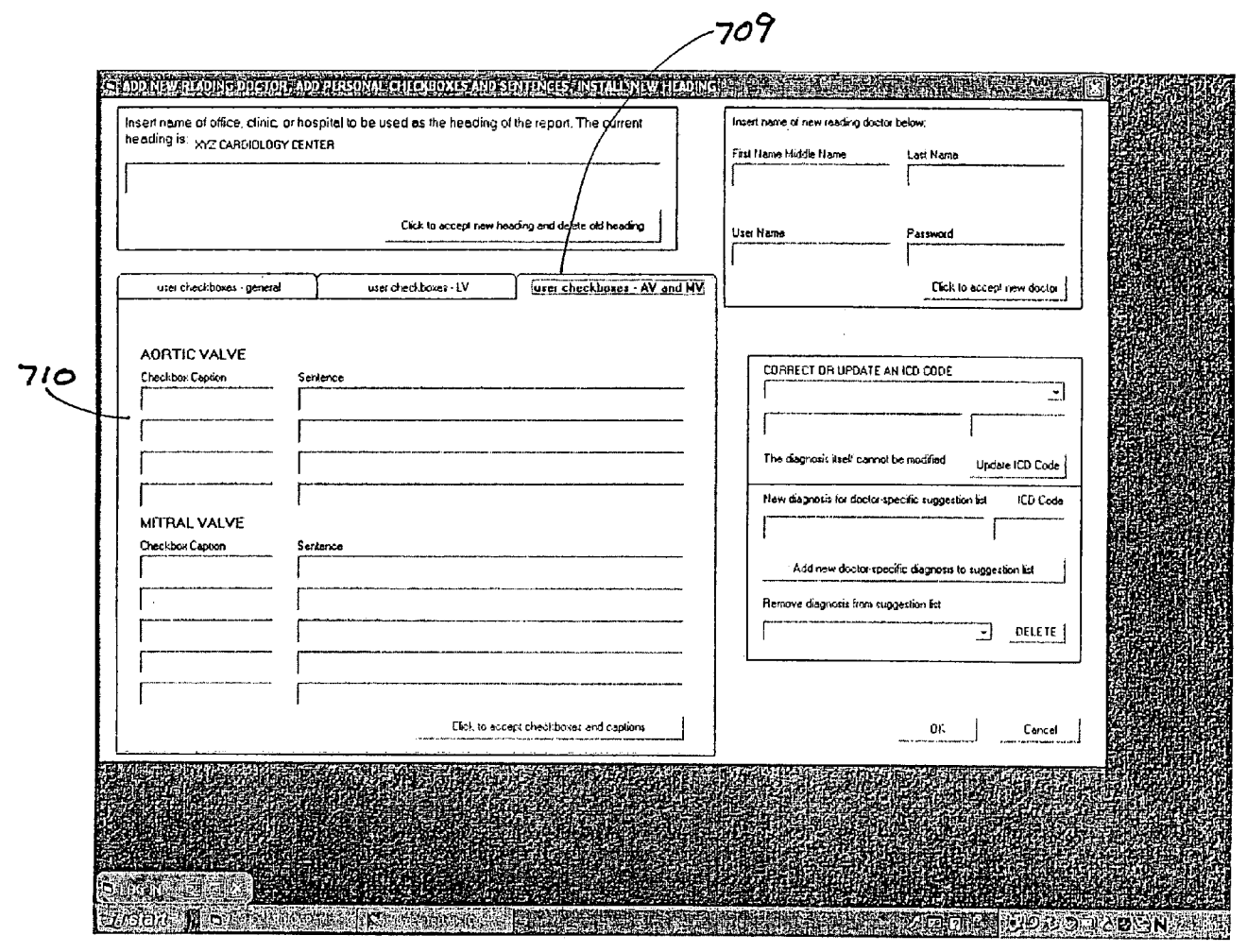

FIG. 7a is a maintenance form screen page 701 which is opened by the Maintenance button 309 on start-up screen page 301, as shown in FIG. 3. Maintenance form screen page 701 is used to register a new reading doctor on boxes 702, add headings in box 703 and add user-specific controls and favorite diagnosis under tabs 704 and boxes 705. FIG. 7a depicts the maintenance form screen page with a "user checkboxes—general" tab 706. FIG. 7b depicts the maintenance form screen page with a "user checkboxes—LV" tab 707 which provides boxes 708 for entry of specific information related to the Left Ventricle. FIG. 7c depicts the maintenance form screen page with a "user checkboxes—AV and MV" tab 709 which provides boxes 710 for entry of specific information related to the Aortic Valve and the Mitral Valve.

Figure 8:
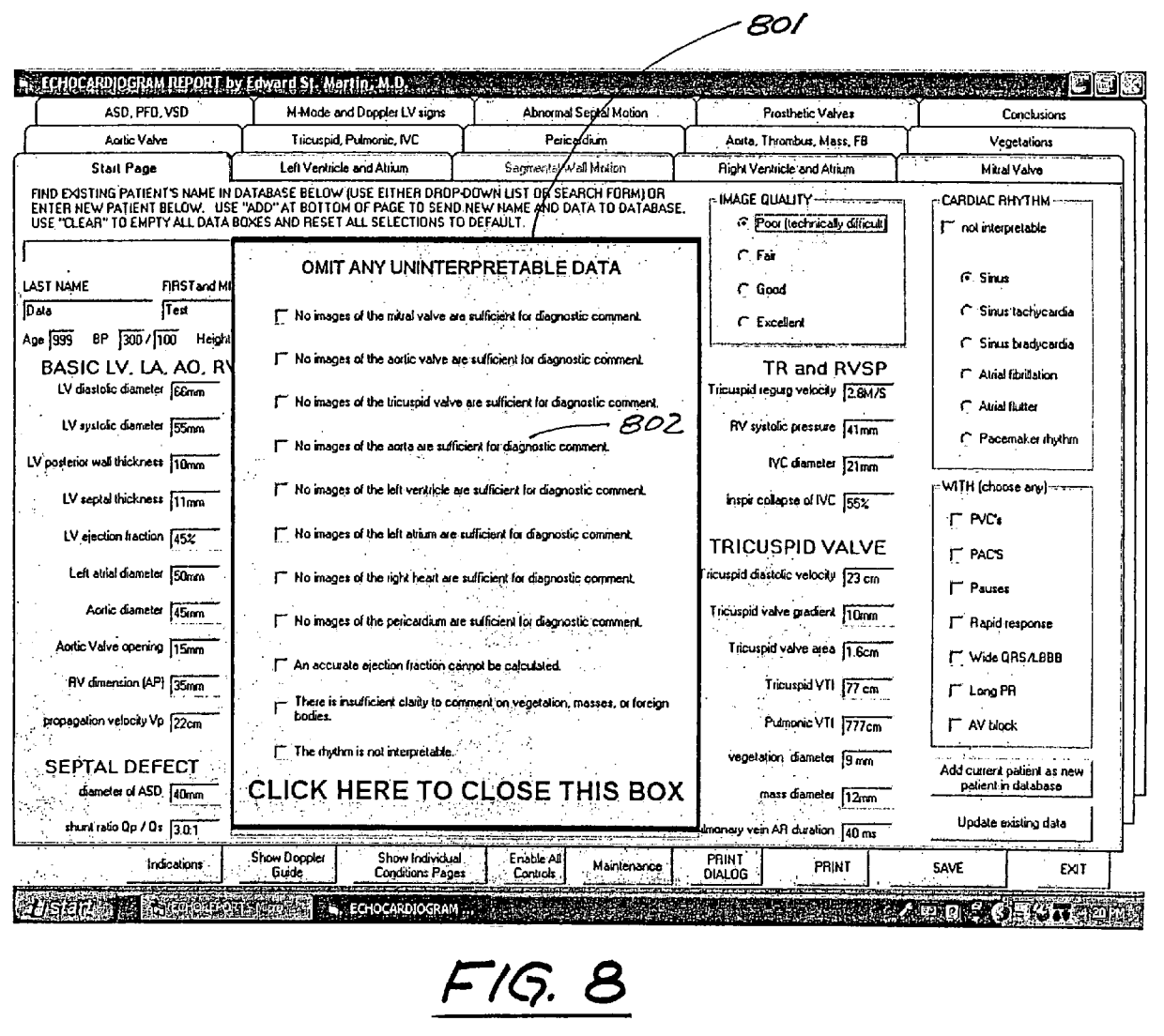

FIG. 8 is an "Omit Any Uninterpretable Data" box 801 displayed on the start-up screen page 301 when the Image Quality box 311 on start-up screen page 301 is checked with a "Poor" image quality selection 312. Box 801 affords the reading doctor several enumerated options relating to specific anatomical structure. For example, if the statement 802 "No images of the aorta are sufficient for diagnostic comment", is selected, then that statement is made in the report and all controls in the inventive method and system related to that anatomical structure are disabled and appear pale grey and do not respond to clicks. However, comments still can be made by clicking the "Enable All Controls" button 313 on the start-up screen page 301 with a warning box that the user must carefully avoid contradictory statements.

FIGS. 9a through 9e are tabbed screen pages opened by clicking on the "Indications" button 314 on the start-up screen page 301. These pages are for ready reference and contain Medicare approved indications for echocardiograms and the ICD-9 codes for each.

Figure 10B:
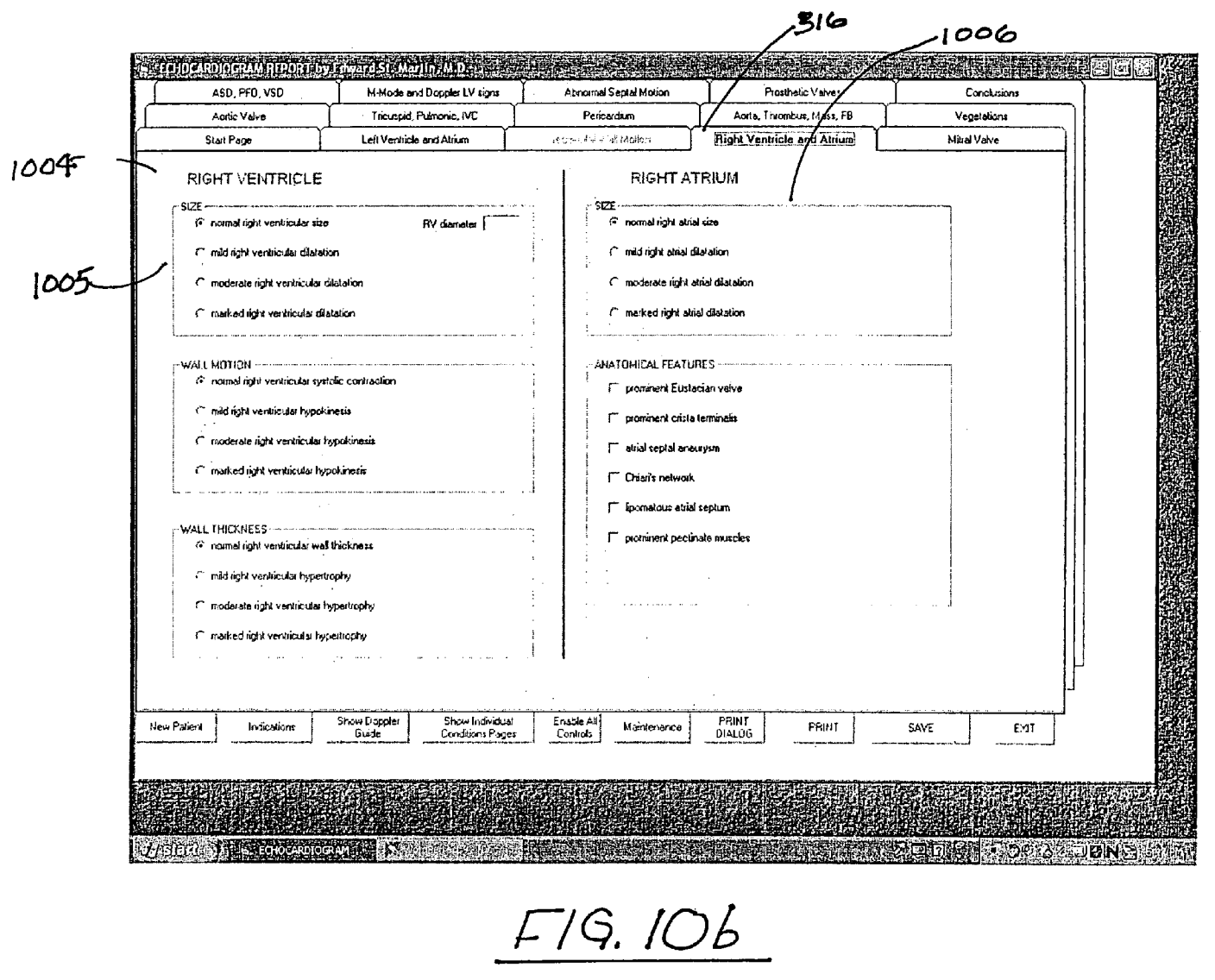
Figure 10C:
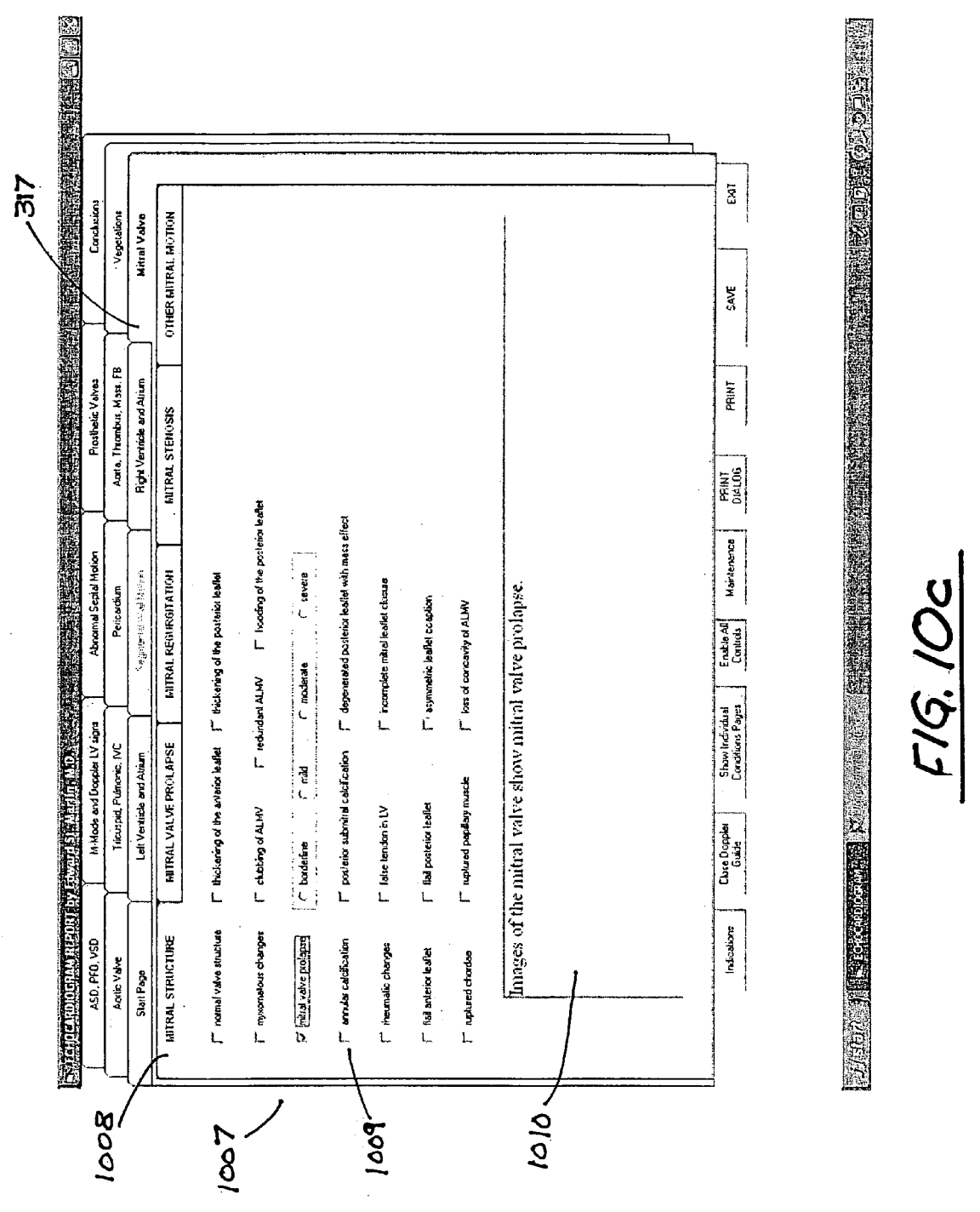
Figure 10D:
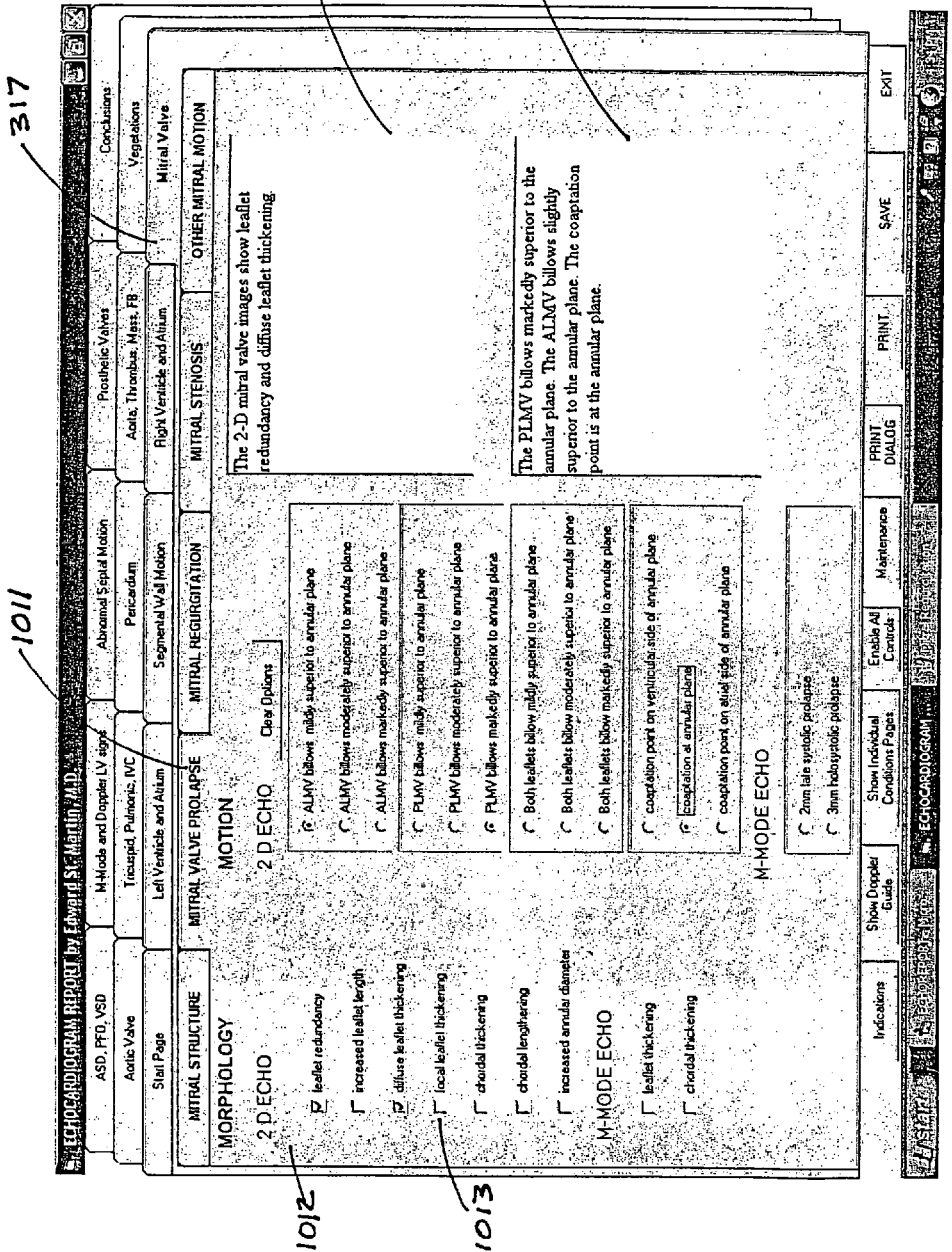
FIGS. 10a through 10z are the tabbed anatomical-based screen pages opened from the start-up page.
Figure 10E:
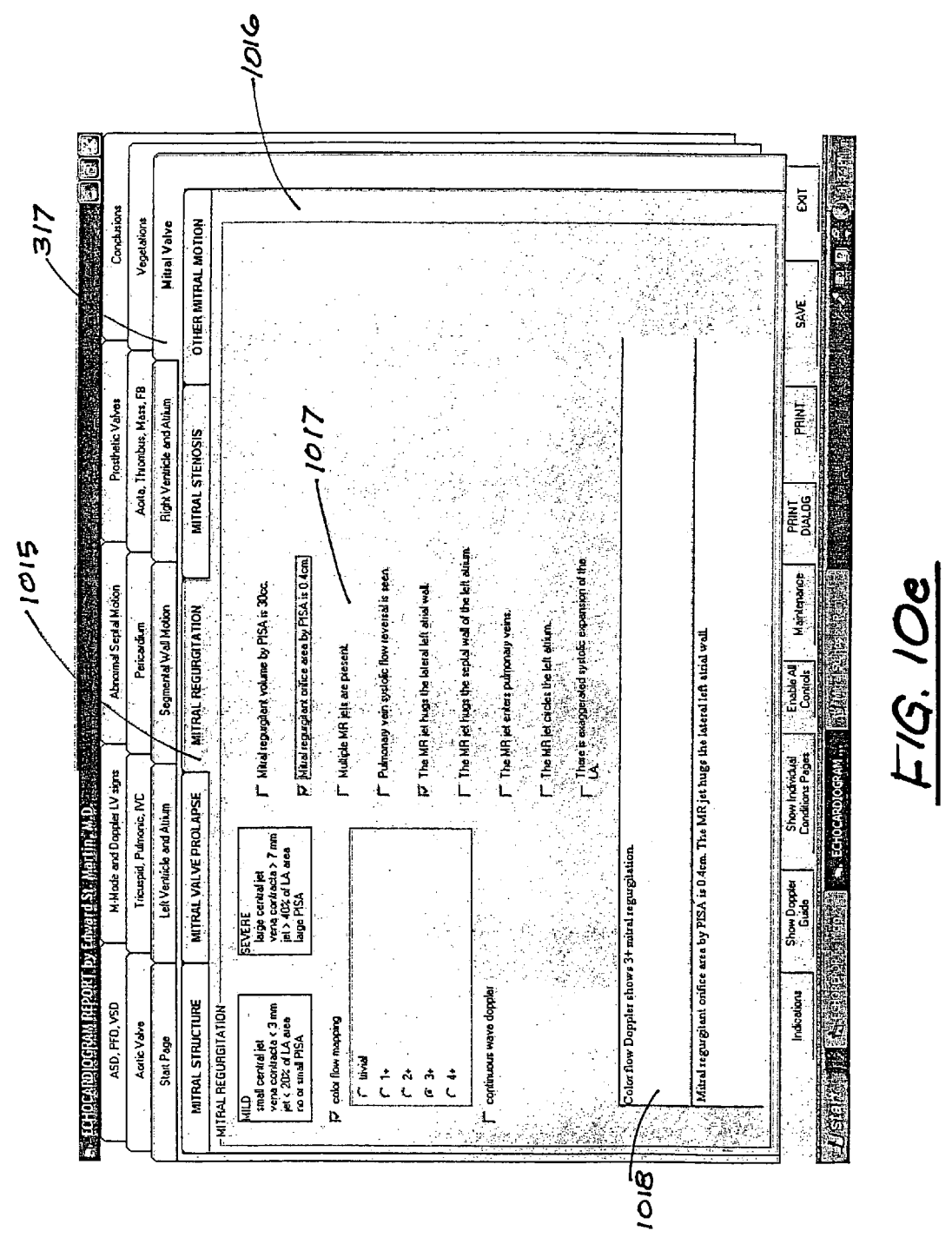
Figure 10F:
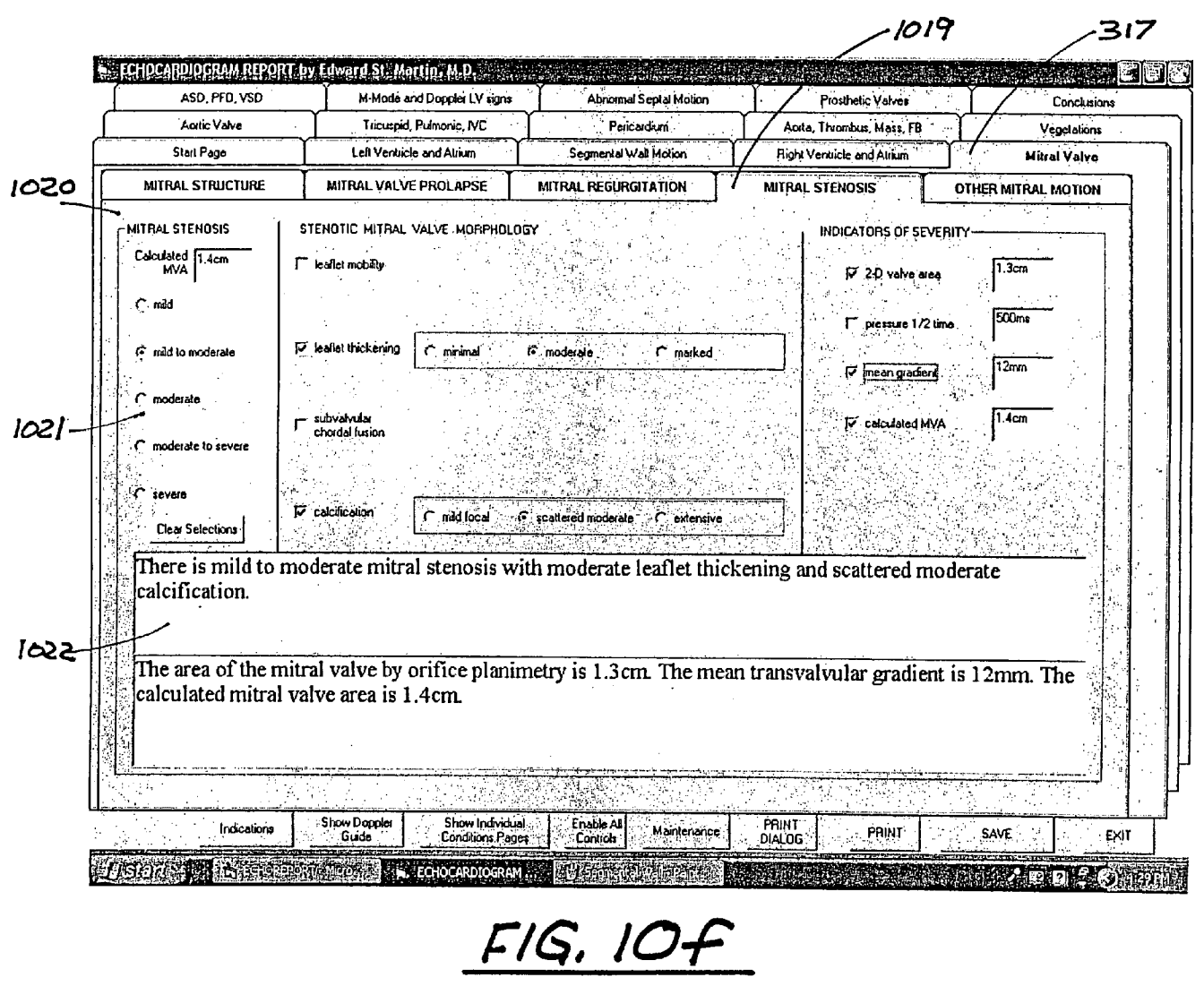
Figure 10G:
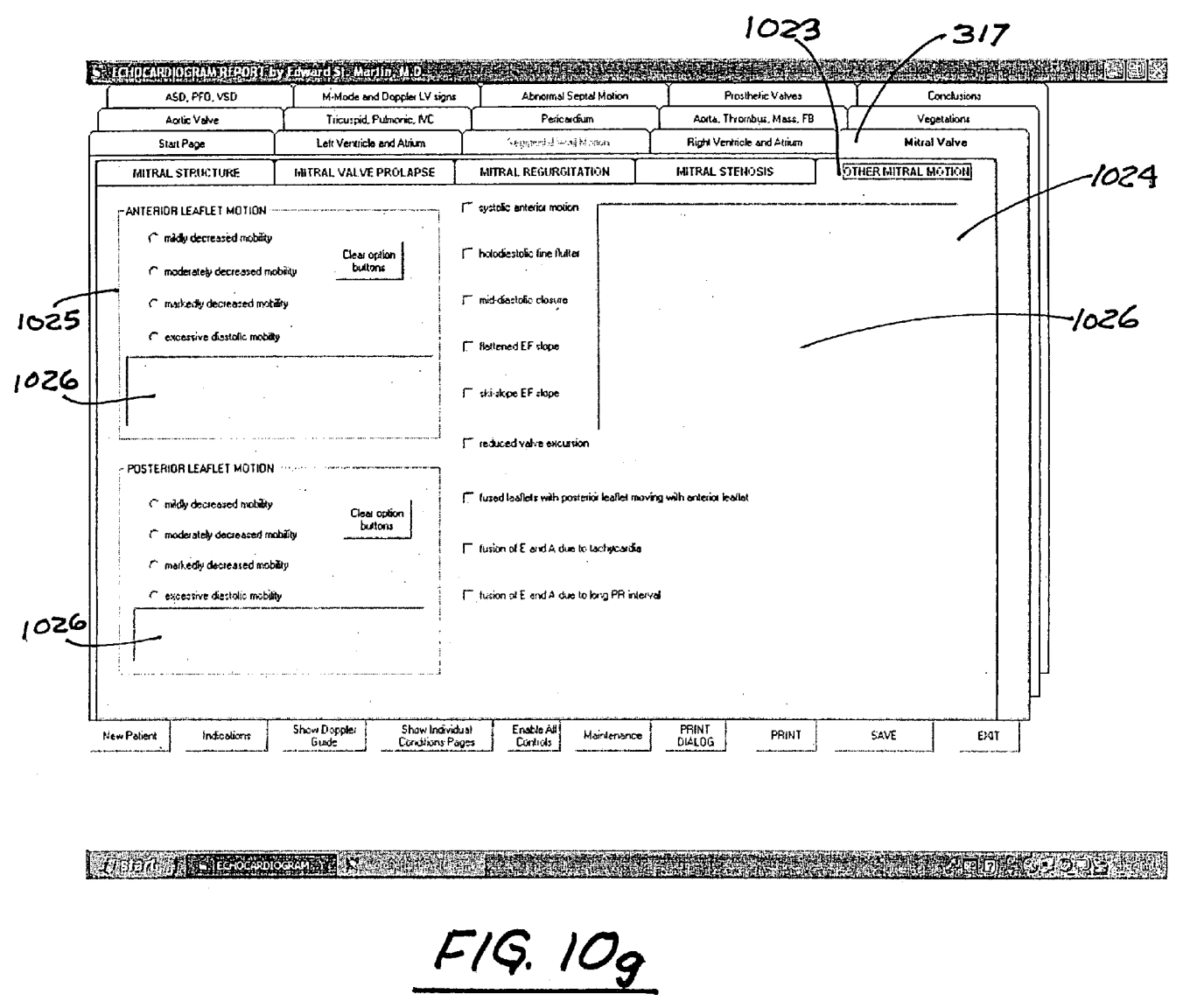
Figure 10H:
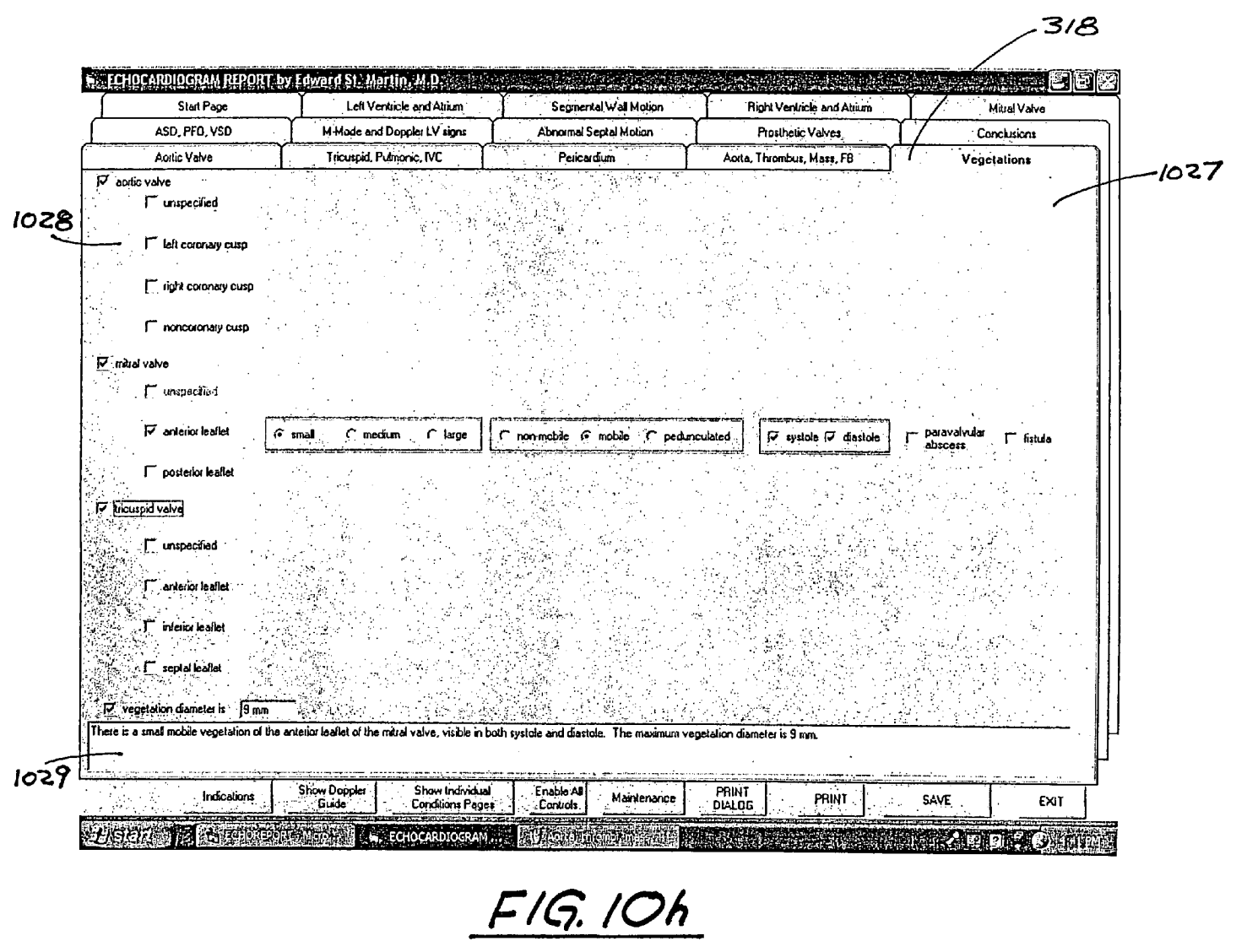
Figure 10I:
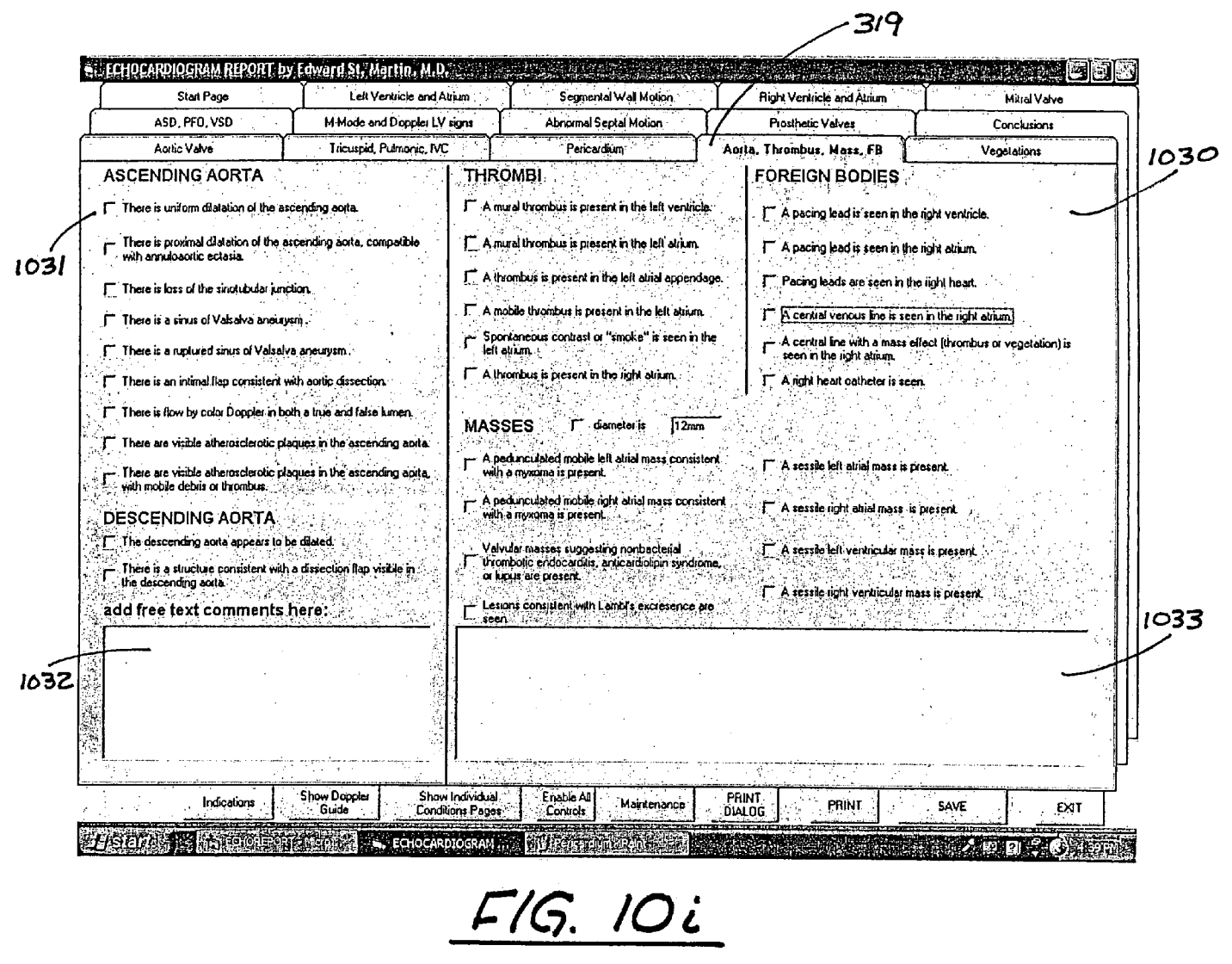
Figure 10J:
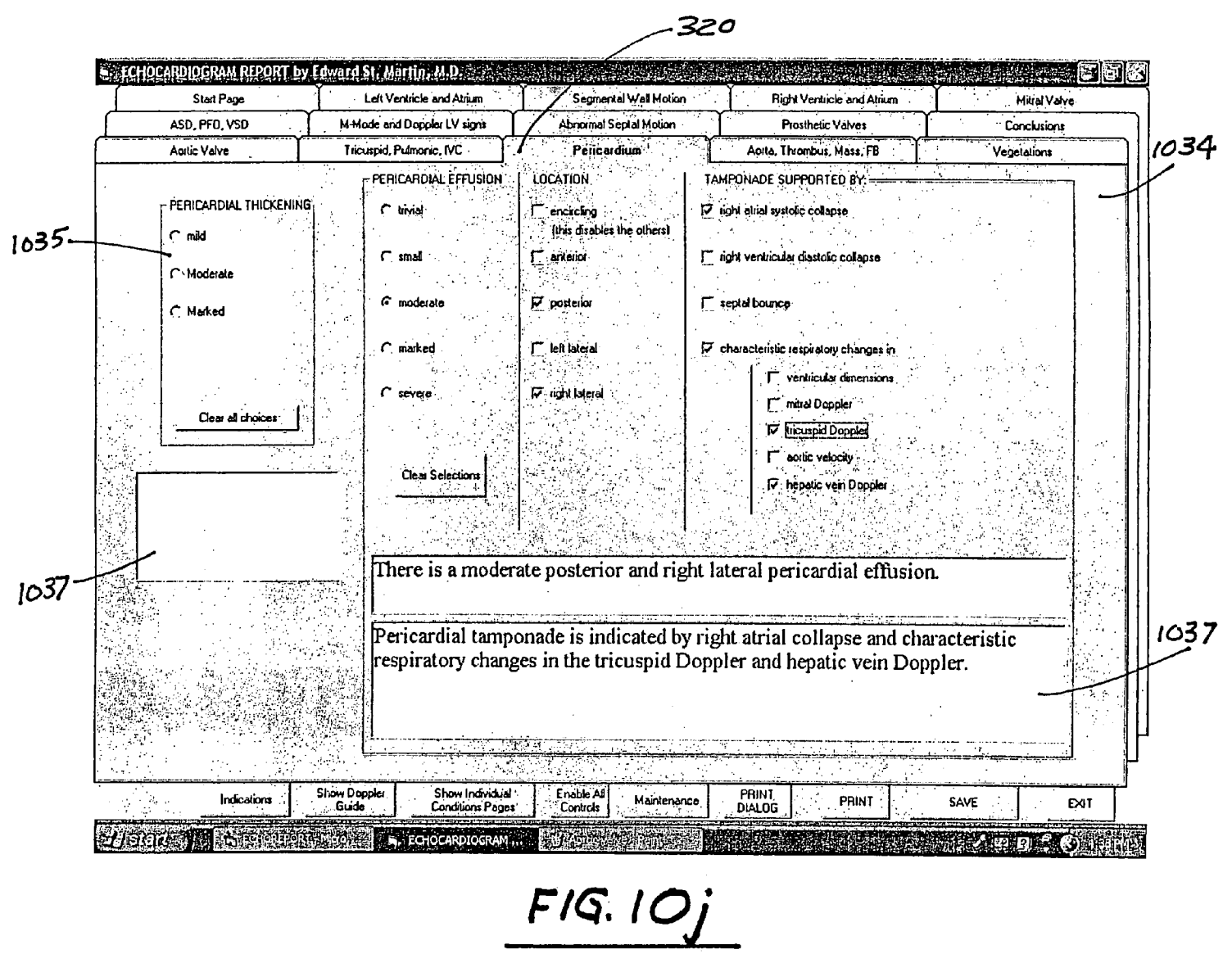
Figure 10K:
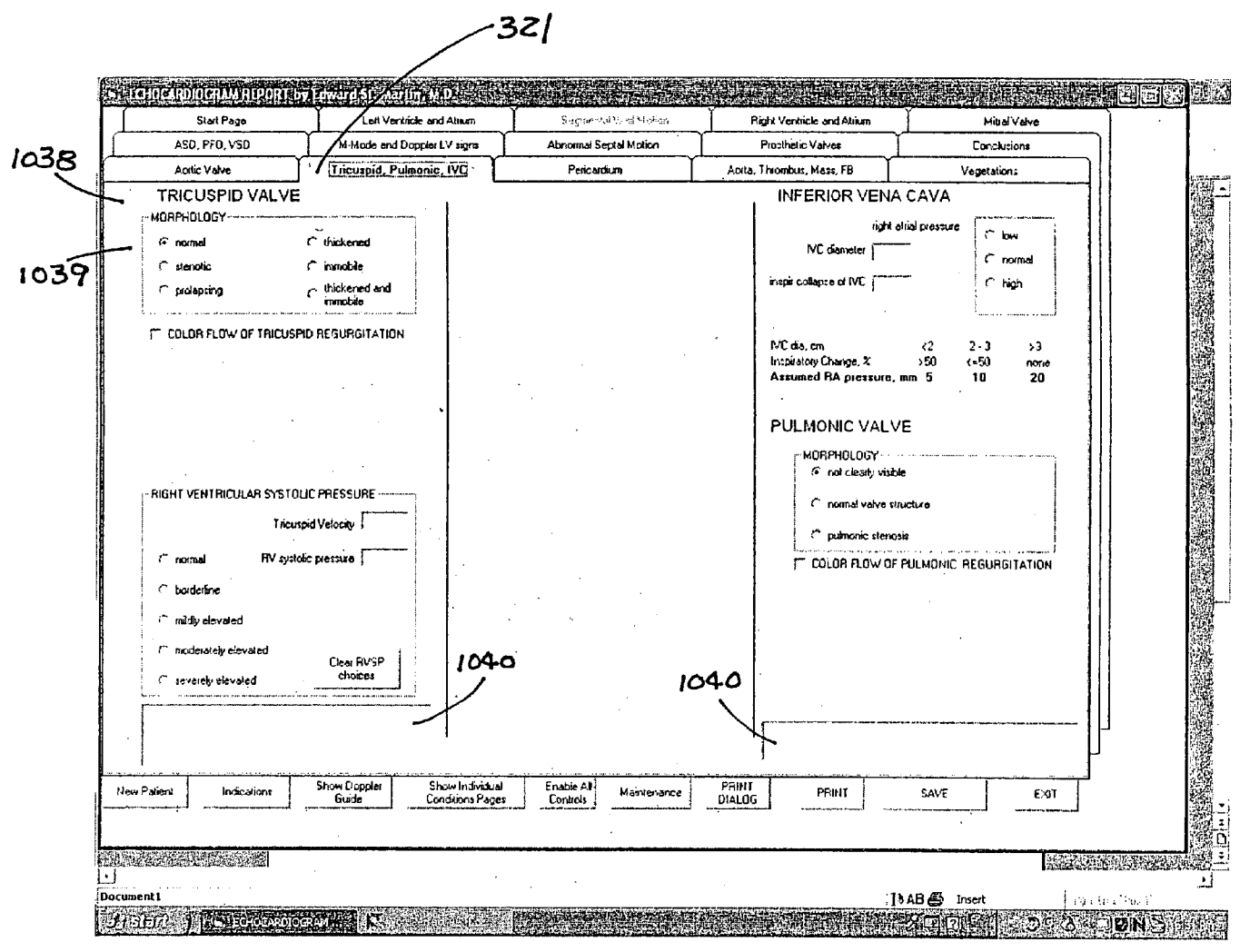
Figure 10L:
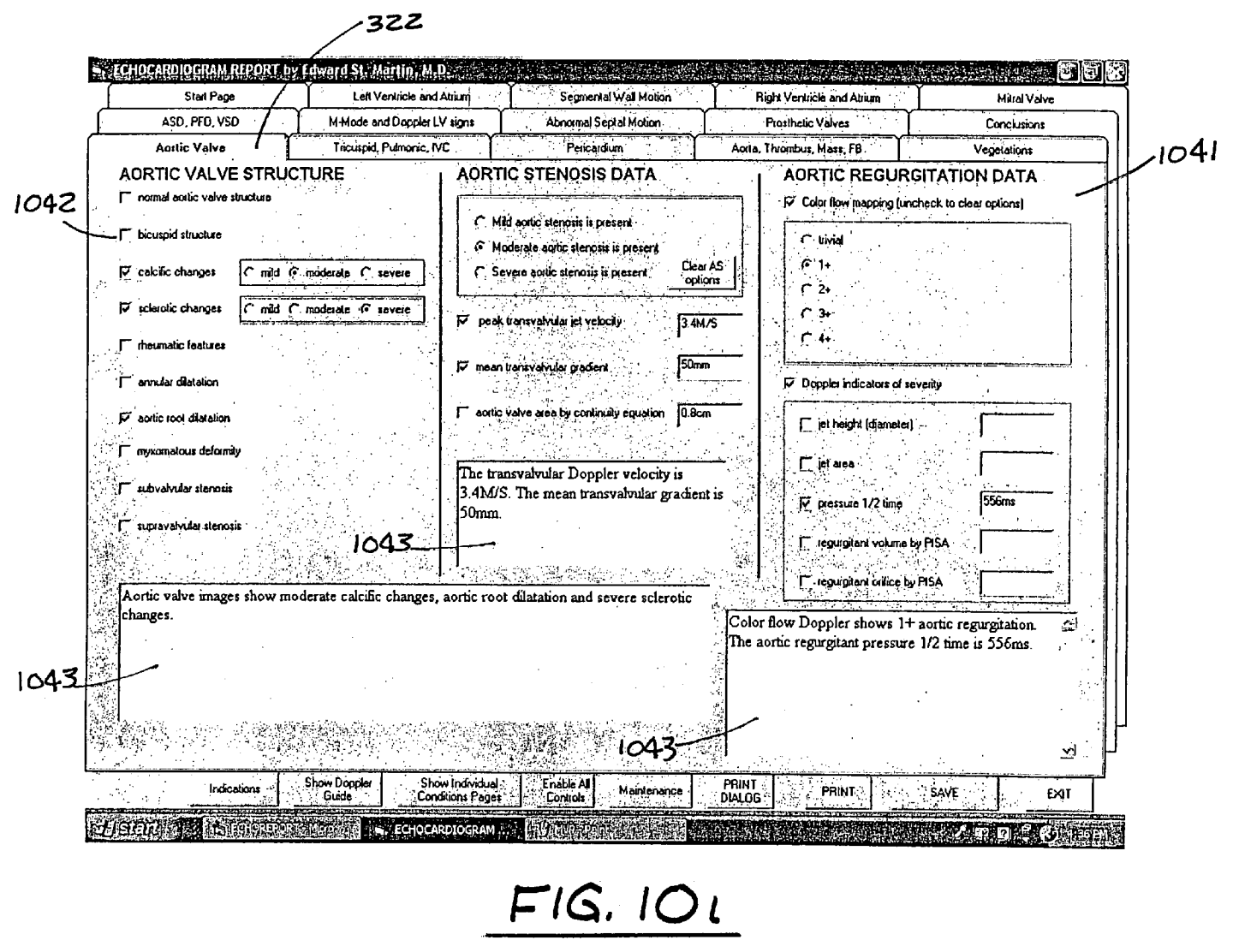
Figure 10M:
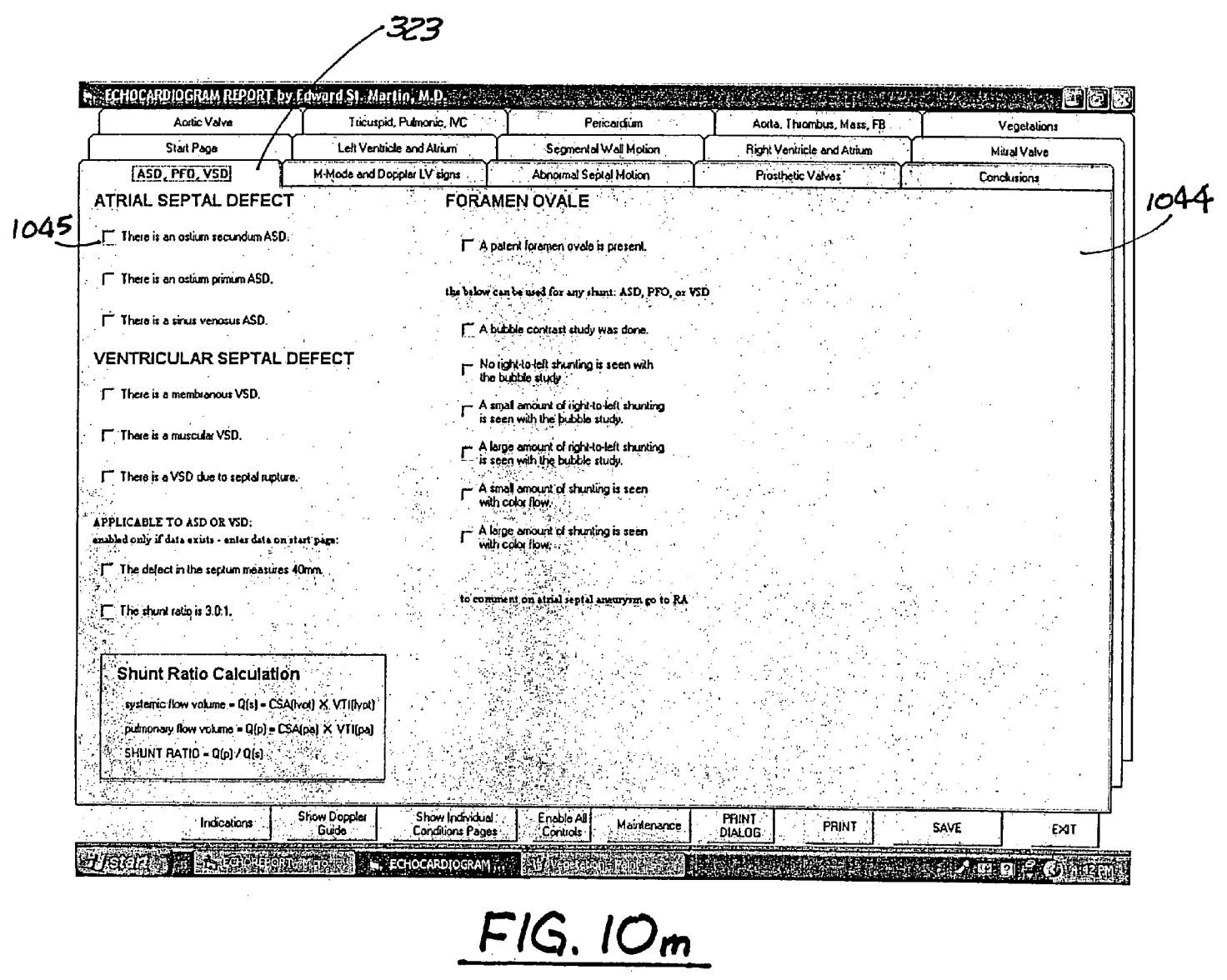
Figure 10N:
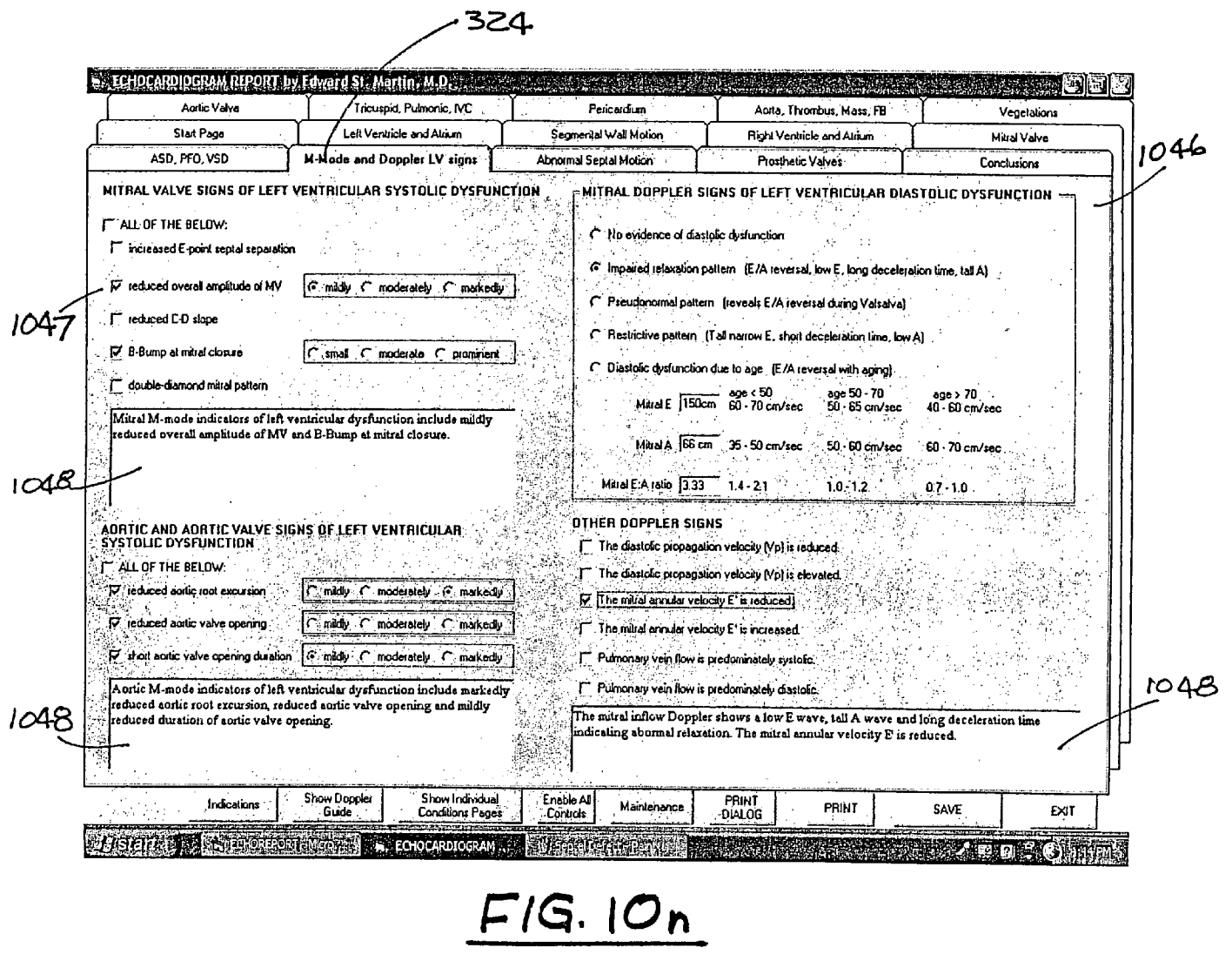
Figure 10O:
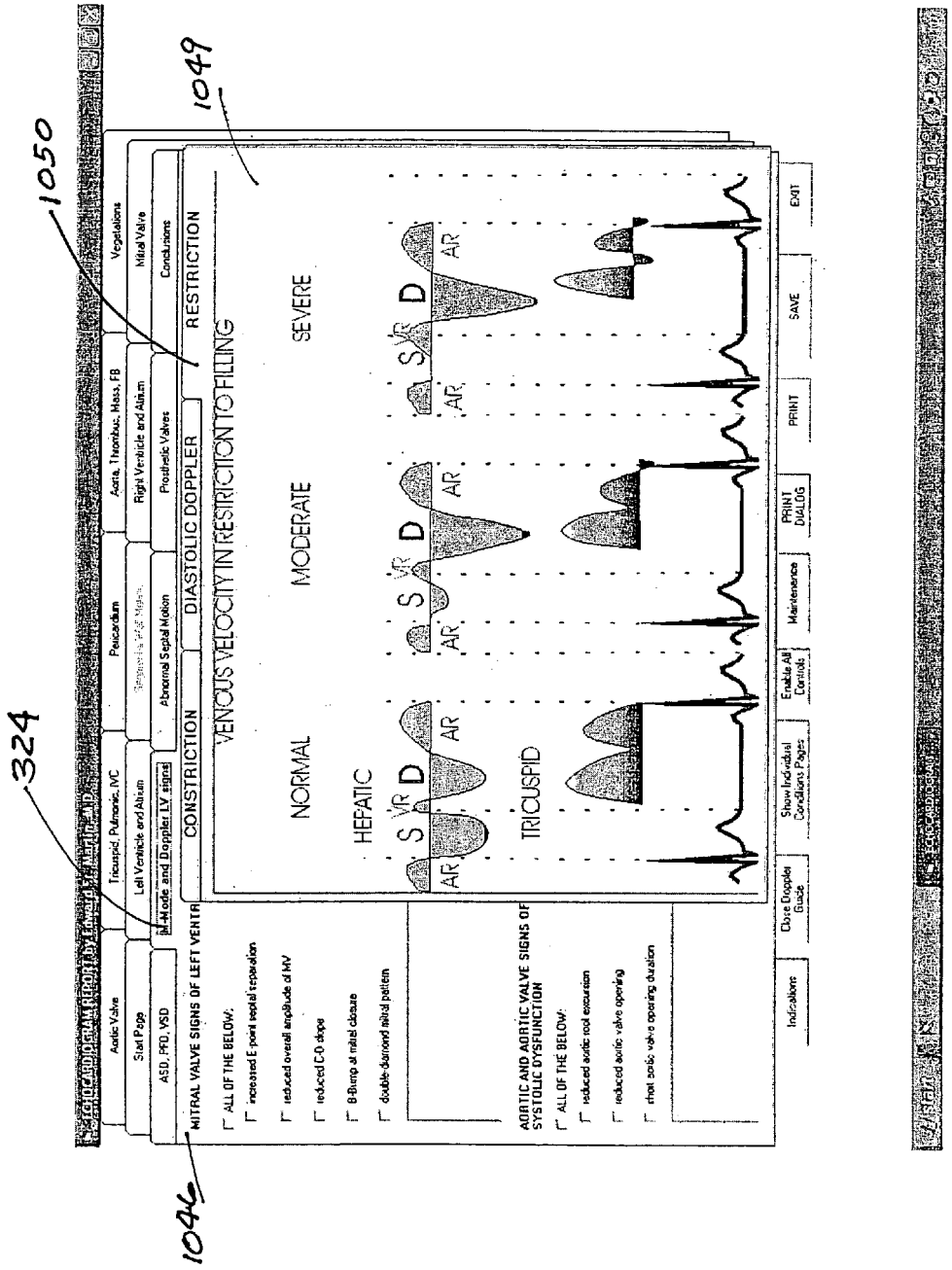
Figure 10P:
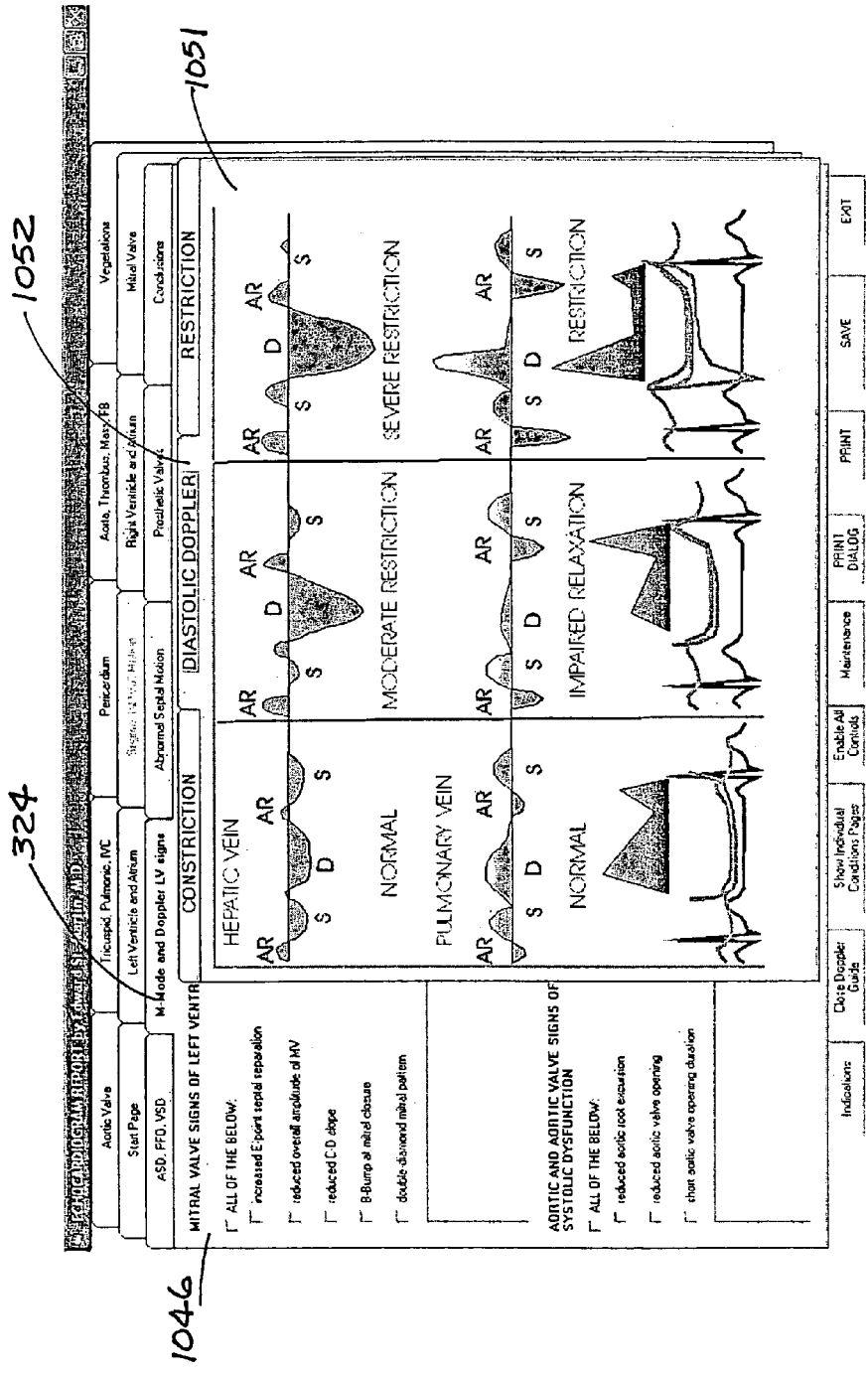
Figure 109:
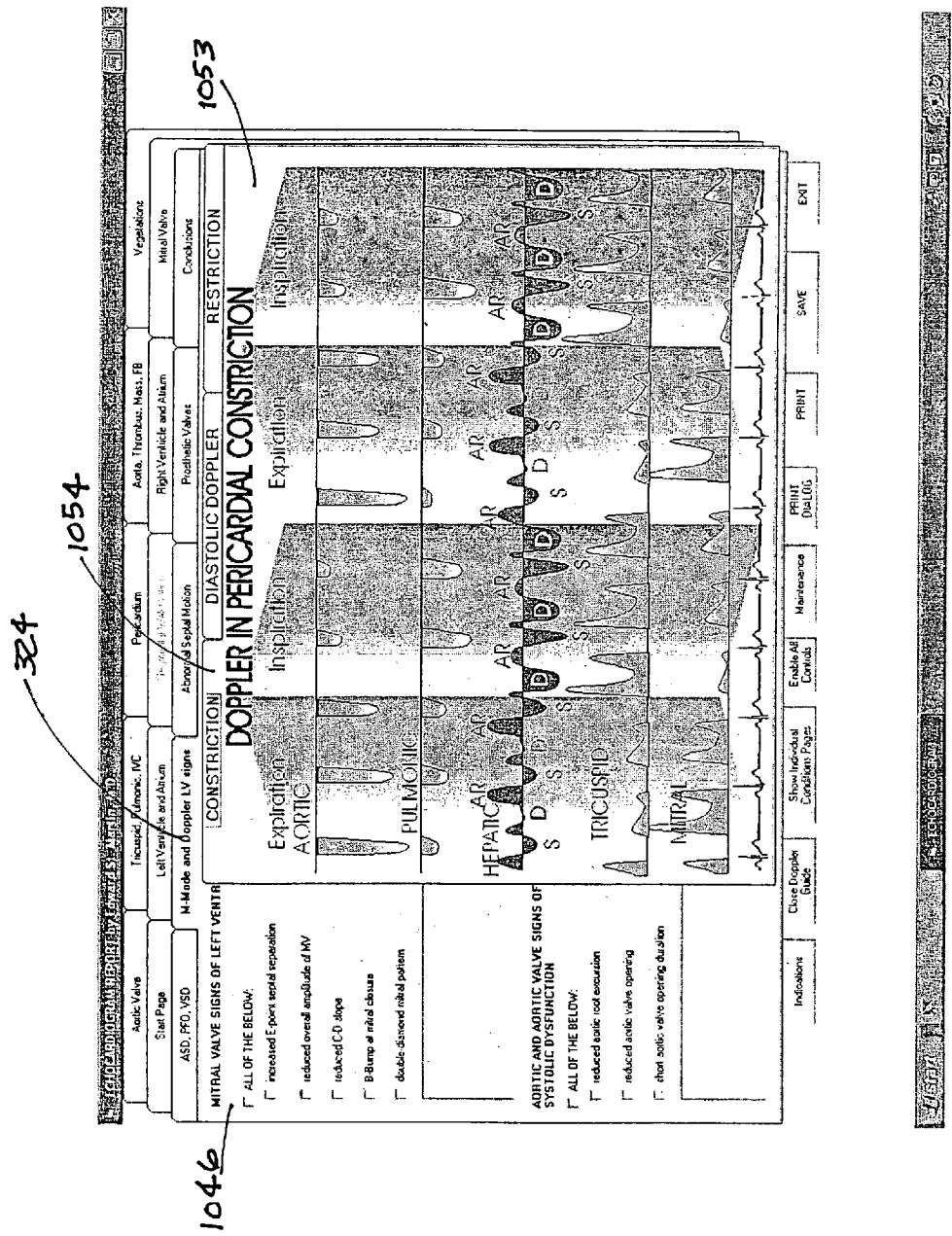
Figure 10R:
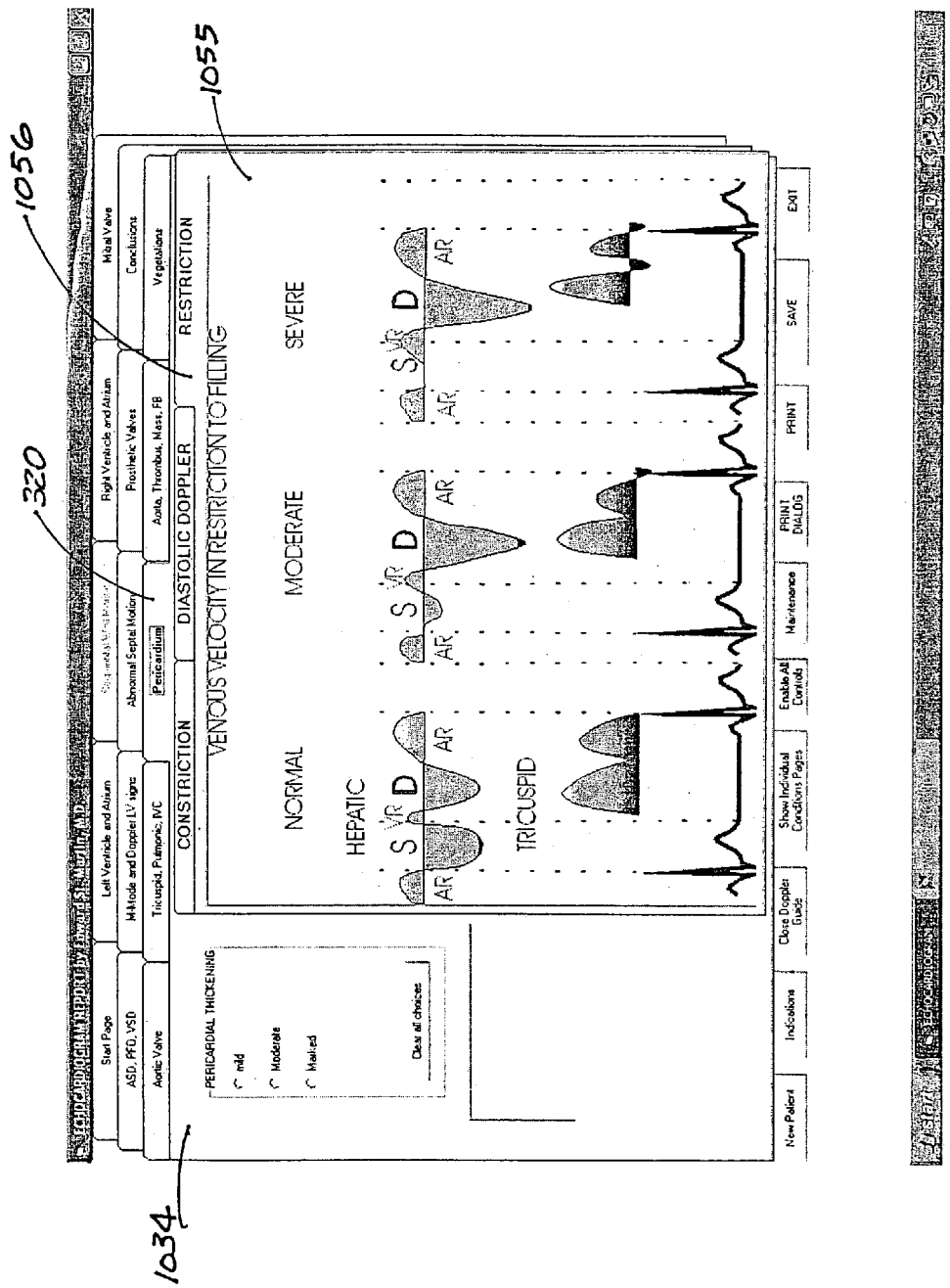
Figure 10S:
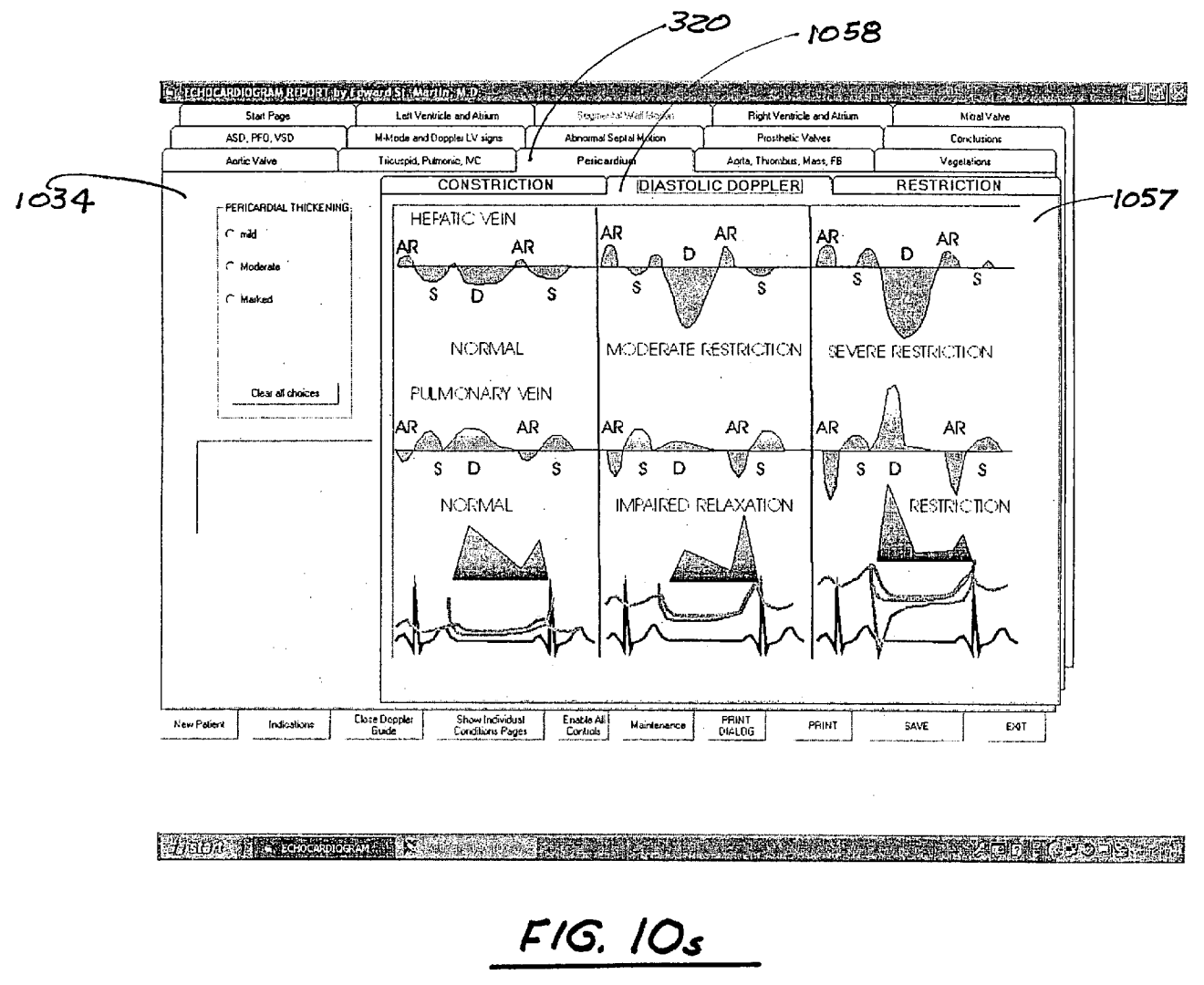
Figure 10T:
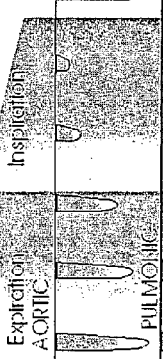
Figure 10V:
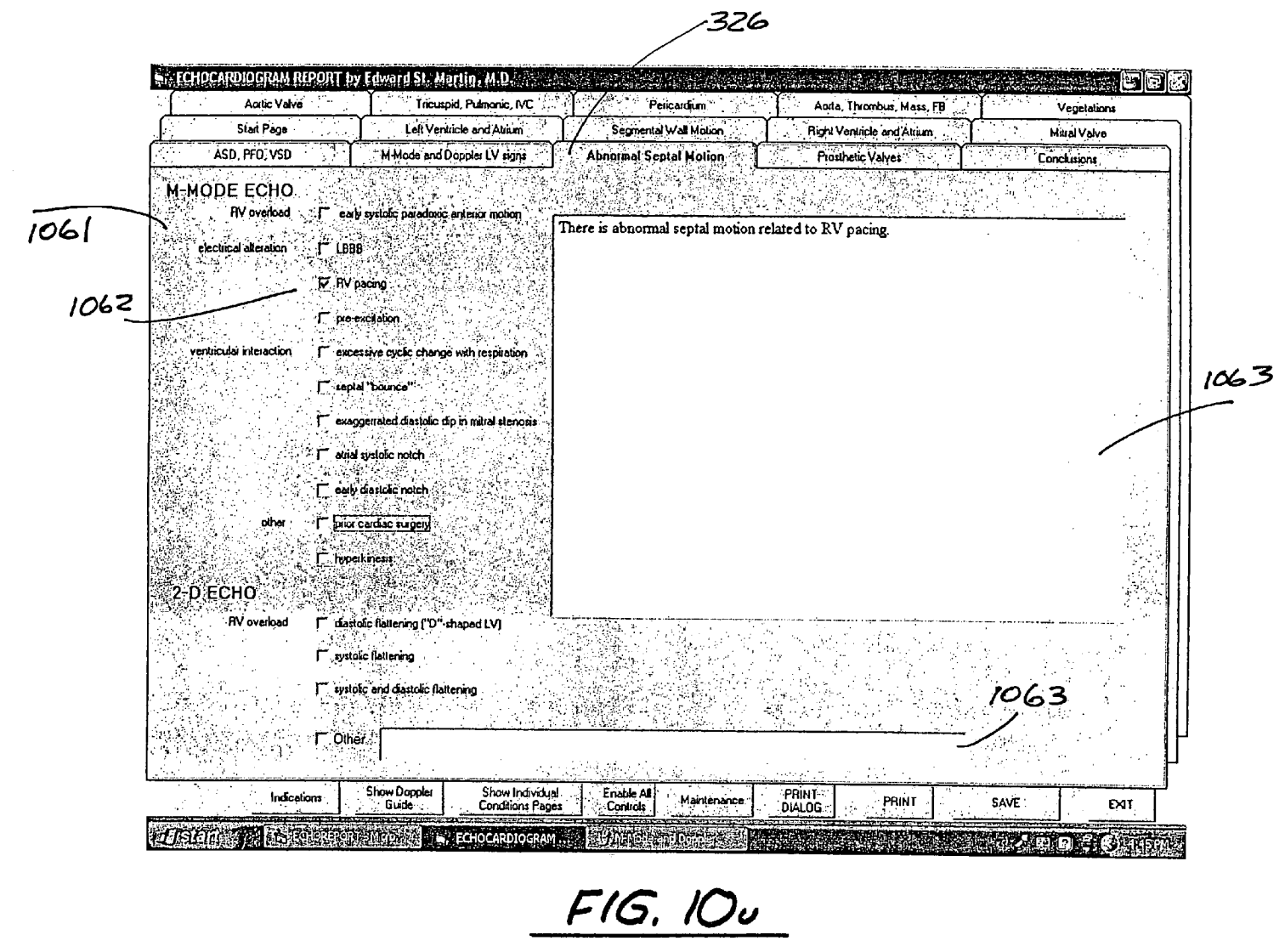
Figure 10V:
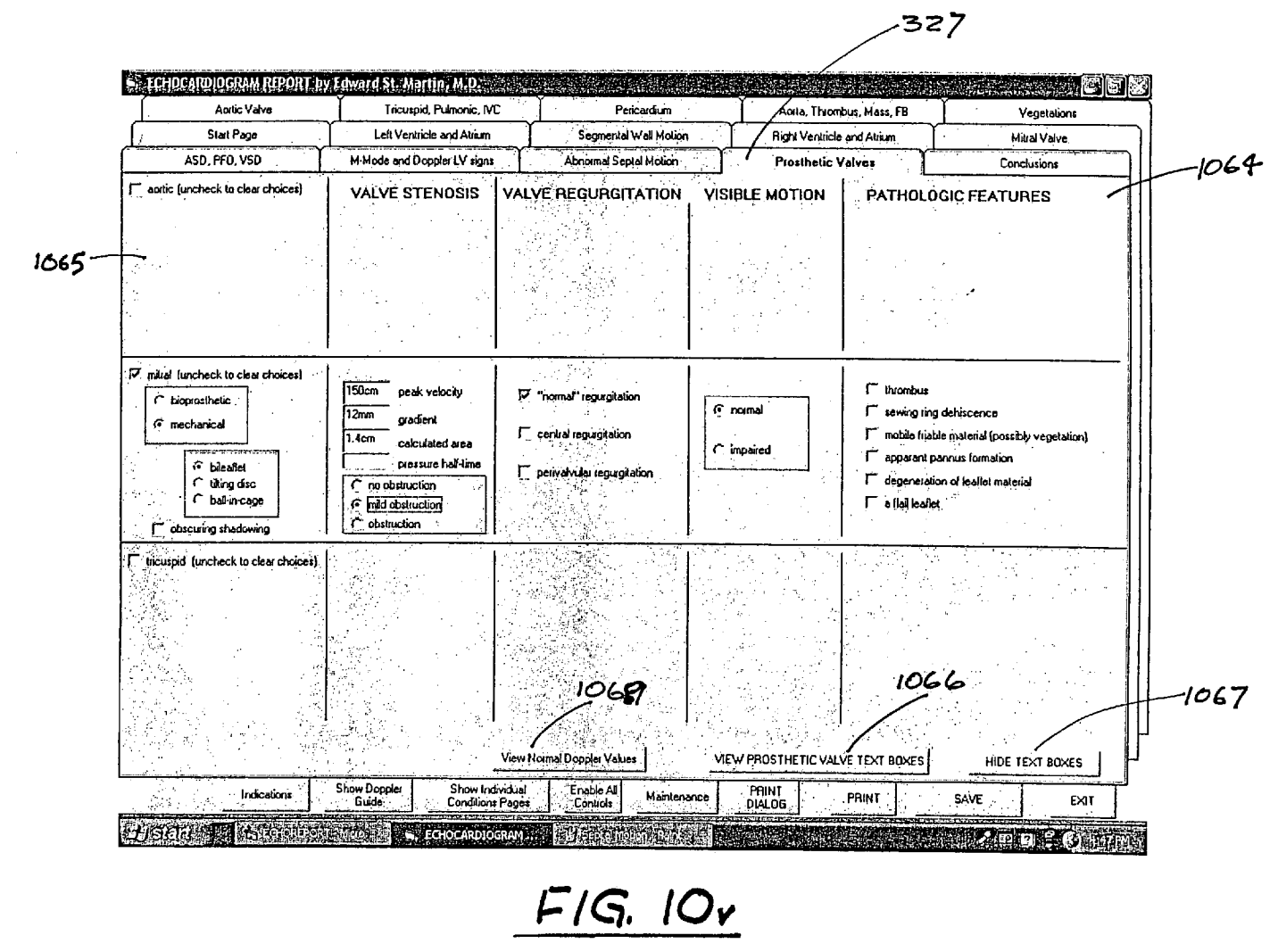
Figure 10:
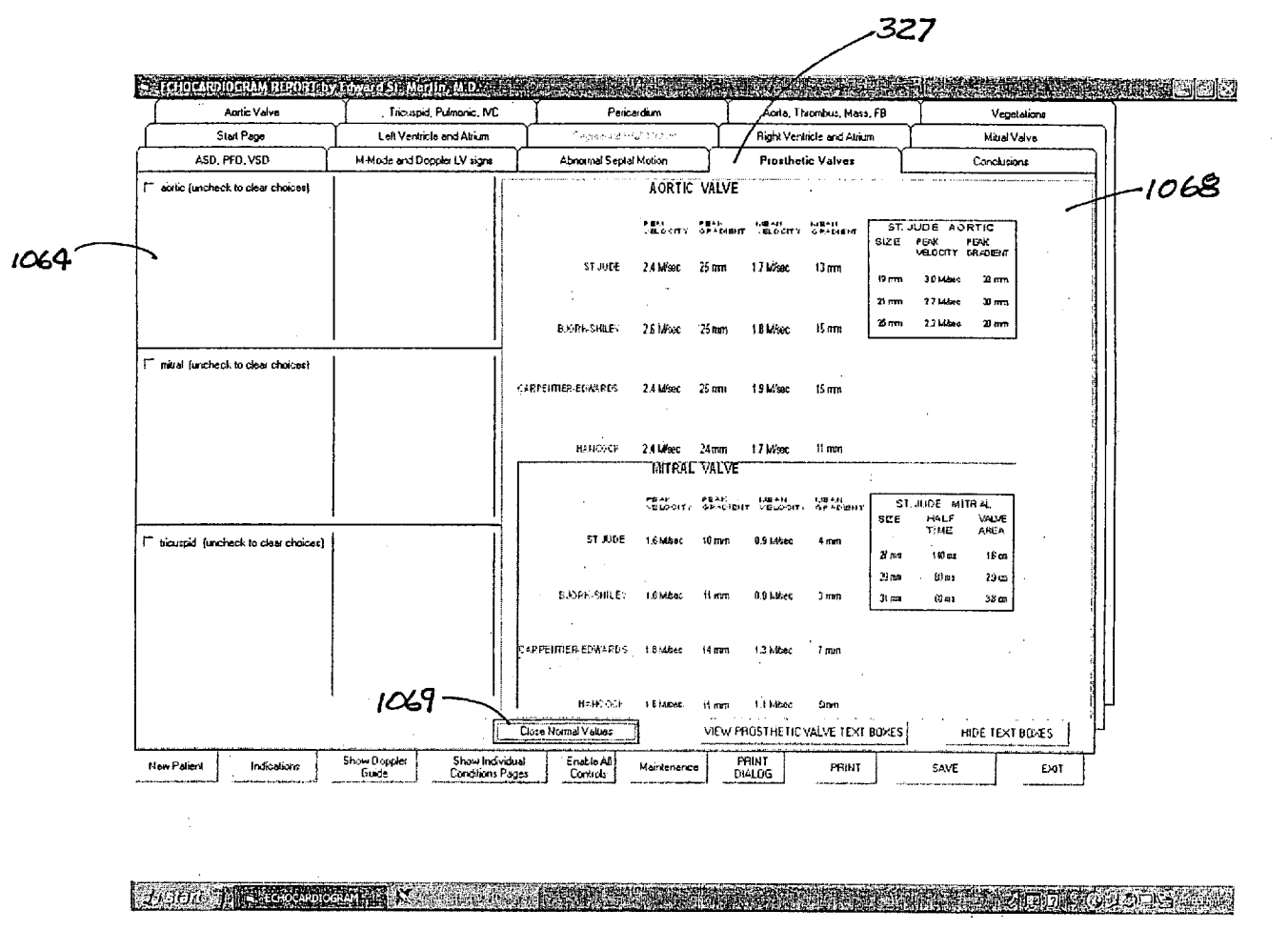
Figure 10X:
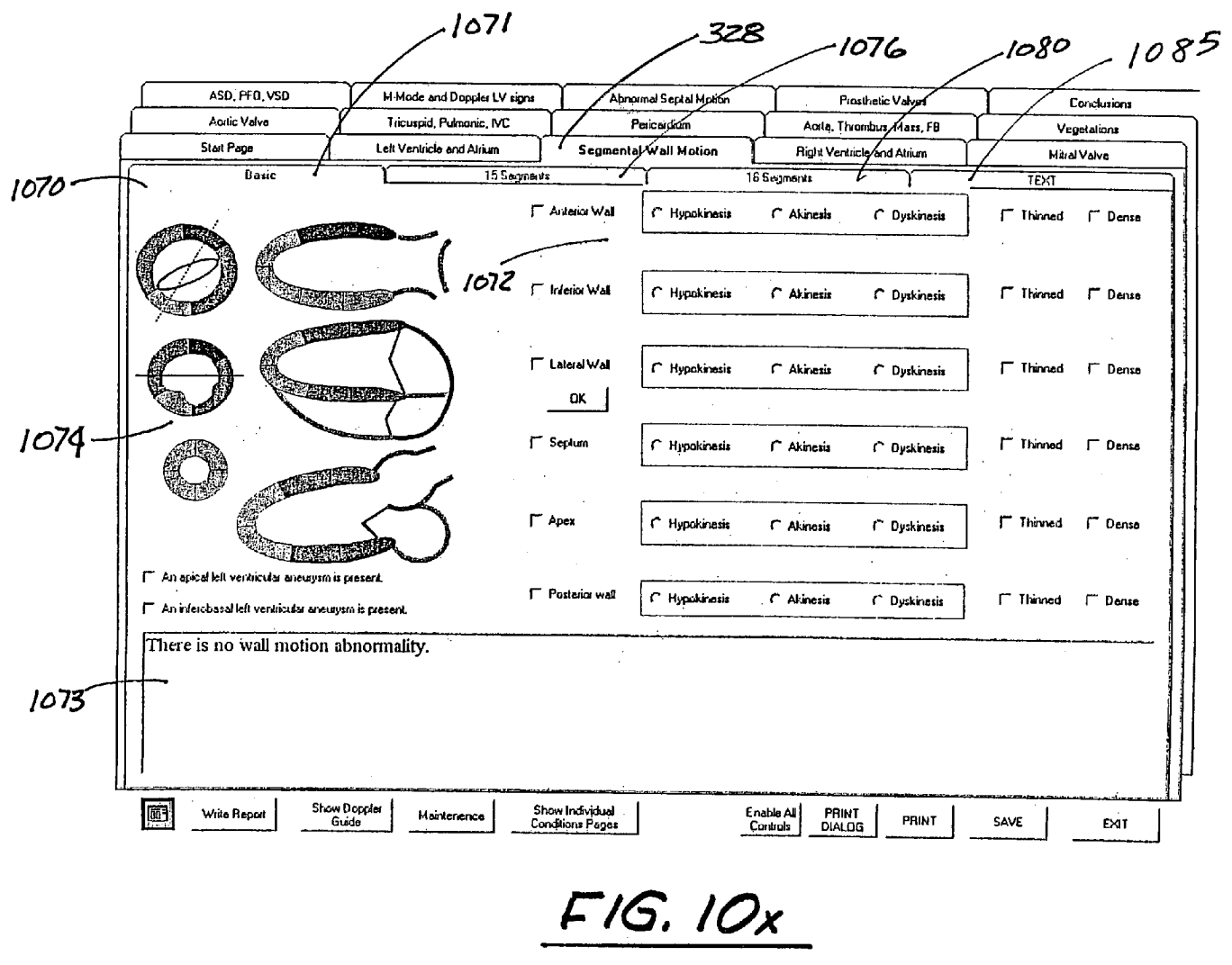
Figure 10Y:
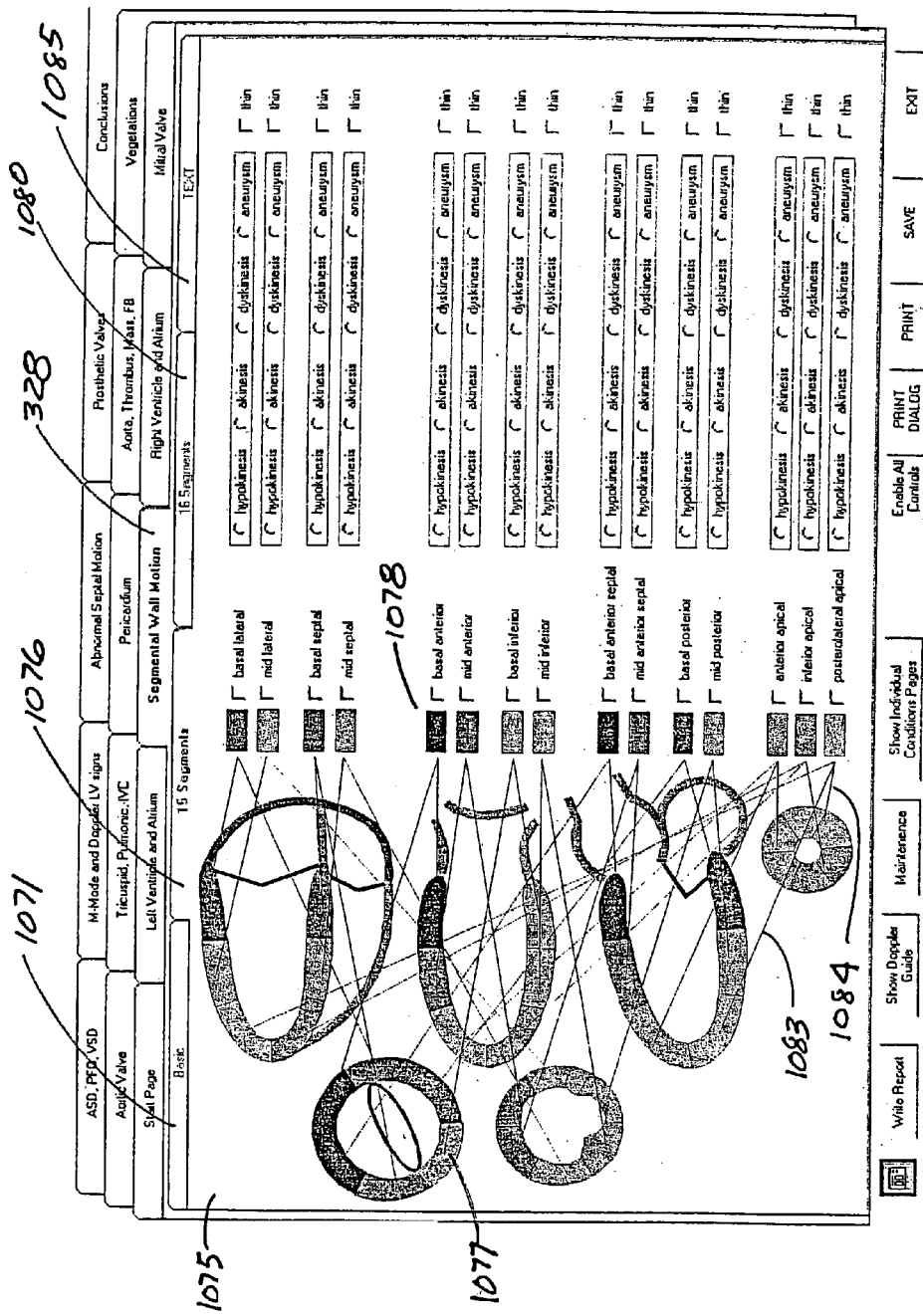
Figure 10Z:
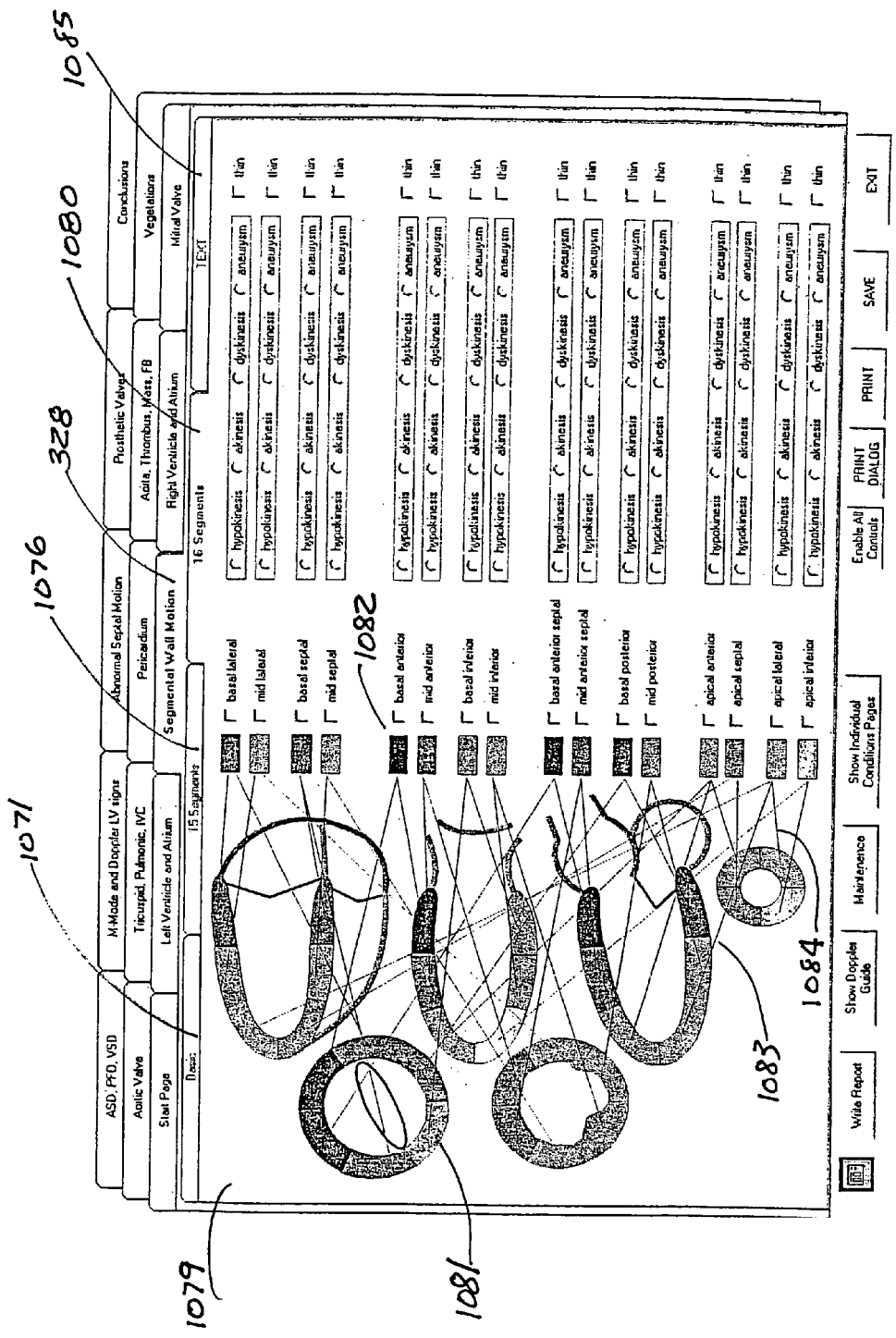
Figure 10A:
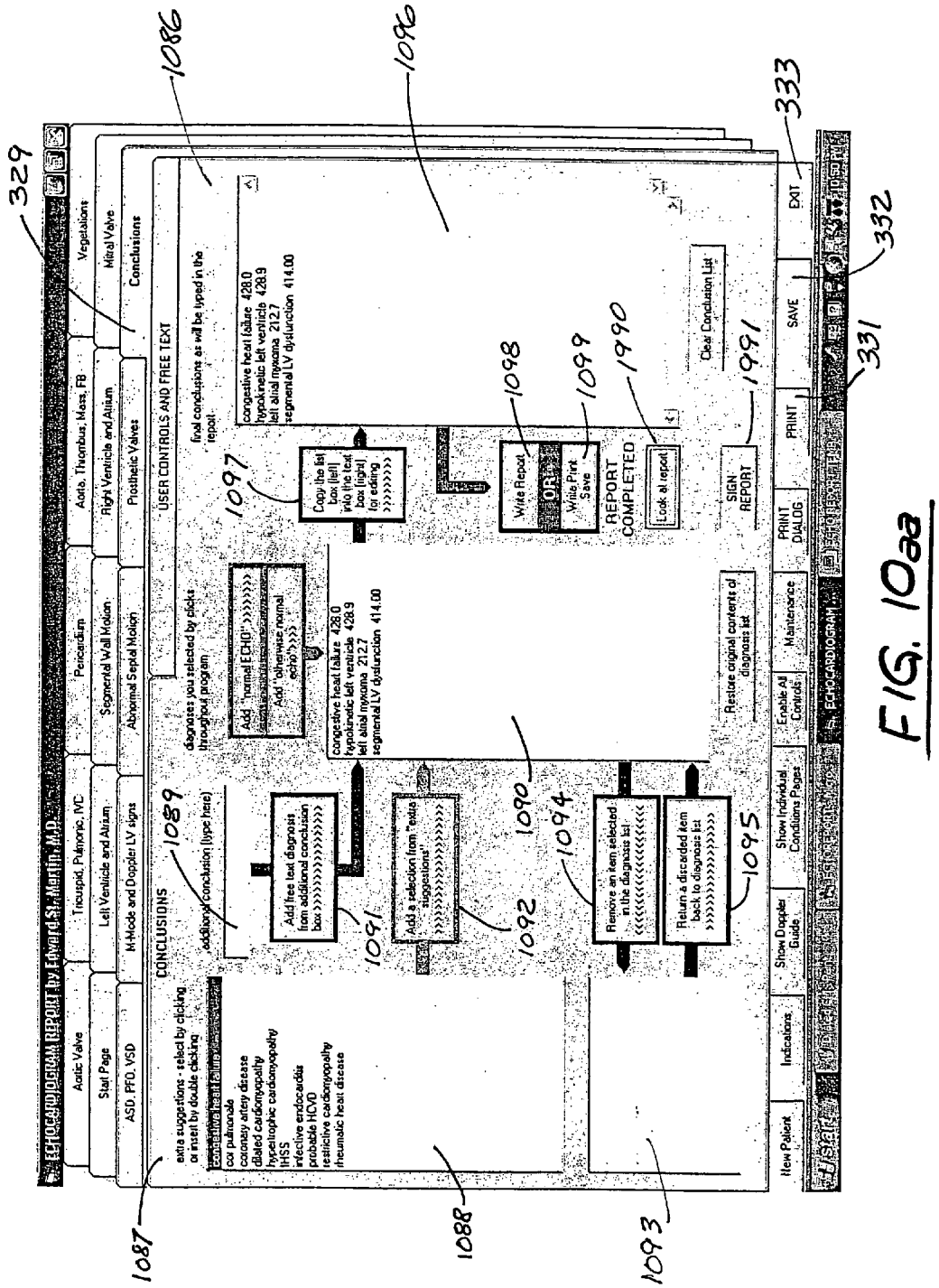
Figure 10A:
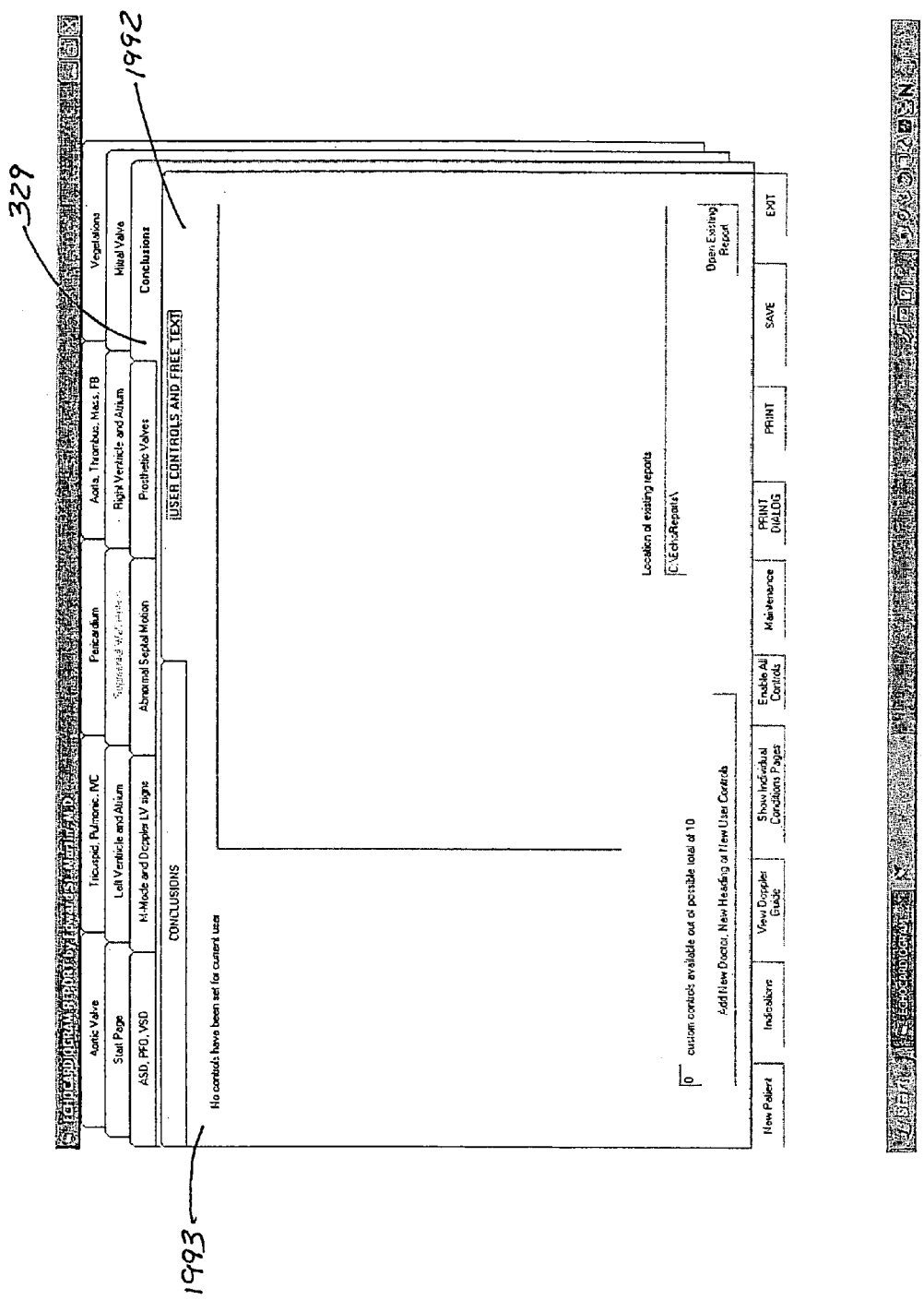
Figure 1I:
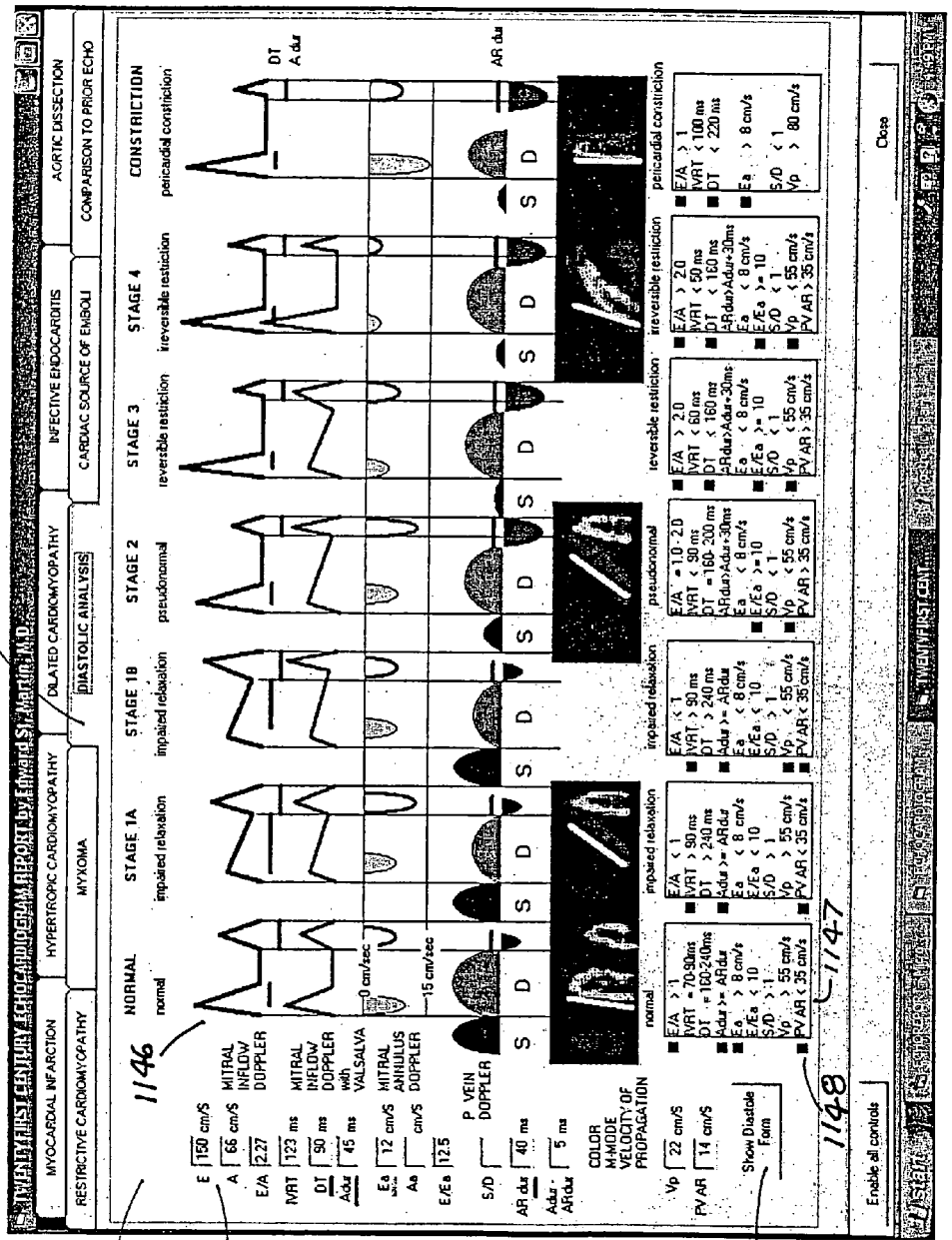

FIGS. 10a through 10z, are the tabbed anatomical-based screen pages opened by clicking on the tabs 303 on the start-up screen page 301 shown in FIG. 3.

FIG. 10a is a screen page 1001 opened by clicking on the "Left Ventricle and Atrium" tab 315 on the start-up screen page 301. This screen page 1001 has option boxes 1002 for entry of comments specific to the left ventricle (LV) and left atrium (LA), and box 1003 for entry of free text comments about the left ventricle and left atrium.

FIG. 10b is a screen page 1004 opened by clicking on the "Right Ventricle and Atrium" tab 316 on the start-up screen page 301. This screen page 1004 has option box 1005 for entry of This screen page 1004 has option box 1005 for entry of comments specific to the right ventricle (RV) and option box 1006 for entry of comments specific to the right atrium (RV).

FIG. 10c is a screen page 1007 opened by clicking on the "Mitral Valve" tab 317 on the start-up screen page 301. This screen page 1007 for the mitral valve has been divided into five sections, each with its own tab and screen page beginning with the "Mitral. Structure" (MS) tab 1008 and screen page 1007 shown in FIG. 10c. On the MS screen page 1007 are provided option boxes 1009 for various comments appropriate to the MS, with a text box 1010 to display grammatically correct sentences reflecting the user's selections from the option boxes 1009. The sentences are constructed in the text box 1010 as the selections are made in the option boxes 1009 and are intended to appear in the final report with minor editing if needed.

Another tabbed section under the "Mitral Valve" tab 317 on the start-up screen page 301 is shown in FIG. 10*d*. FIG. 10*d* shows a "Mitral Valve Prolapse" (MVP) tab 1011 and screen page 1012 with option boxes 1013 for various comments appropriate to MVP, with text boxes 1014 to display grammatically correct sentences reflecting the user's selections from the option boxes 1013. The sentences are constructed in the text boxes 1014 as the selections are made in the option boxes 1013 and are intended to appear in the final report with minor editing if needed.

Another tabbed section under the "Mitral Valve" tab 317 on the start-up screen page 301 is shown in FIG. 10*e*. FIG. 10*e* shows a "Mitral Regurgitation" (MR) tab 1015 and screen page 1016 with option boxes 1017 for various comments appropriate to MR, with text boxes 1018 to display grammatically correct sentences reflecting the user's selections from the option boxes 1017. The sentences are constructed in the text boxes 1018 as the selections are made in the option boxes 1017 and are intended to appear in the final report with minor editing if needed.

Another tabbed section under the "Mitral Valve" tab 317 on the start-up screen page 301 is shown in FIG. 10*f*. FIG. 10*f* shows a "Mitral Stenosis" (MS) tab 1019 and screen page 1020 with option boxes 1021 for various comments appropriate to MS, with text boxes 1022 to display grammatically correct sentences reflecting the user's selections from the option boxes 1021. The sentences are constructed in the text boxes 1022 as-the selections are made in the option boxes 1021 and are intended to appear in the final report with minor editing if needed.

The last tabbed section under the "Mitral Valve" tab 317 on the start-up screen page 301 is shown in FIG. 10*g*. FIG. 10*g* shows an "Other Mitral Motion" tab 1023 and screen page 1024 with option boxes 1025 for various comments appropriate to Other Mitral Motion, with text boxes 1026 to display grammatically correct sentences reflecting the user's selections from the option boxes 1025. The sentences are constructed in the text boxes 1026 as the selections are made in the option boxes 1025 and are intended to appear in the final report with minor editing if needed.

FIG. 10*h* is a screen page 1027 opened by clicking on the "Vegetations" tab 318 on the start-up screen page 301. This screen page 1027 has option boxes 1028 for entry of comments specific to vegetation location and size, and text box 1029 to display grammatically correct sentences reflecting the user's selections from the option boxes 1028. The sentences are constructed in the text boxes 1029 as the selections are made in the option boxes 1028 and are intended to appear in the final report with minor editing if needed.

FIG. 10*i* is a screen page 1030 opened by clicking on the "Aorta, Thrombus, Mass, FB" tab 319 on the start-up screen page 301. This screen page 1030 has option boxes 1031 for entry of comments specific to the ascending aorta, the descending aorta, thrombi, masses and foreign bodies, a free text box 1032 for entry of free text comments about the ascending aorta, the descending aorta, thrombi, masses and foreign bodies, and text box 1033 to display grammatically correct sentences reflecting the user's selections from the option boxes 1031. The sentences are constructed in the text box 1033 as the selections are made in the option boxes 1031 and are intended to appear in the final report with minor editing if needed.

FIG. 10*j* is a screen page 1034 opened by clicking on the "Pericardium" tab 320 on the start-up screen page 301. This screen page 1034 has option boxes 1035 for entry of comments specific to the pericardium, and text boxes 1037 to display grammatically correct sentences reflecting the user's selections from the option boxes 1035. The sentences are constructed in the text boxes 1037 as the selections are made in the option boxes 1035 and are intended to appear in the final report with minor editing if needed.

FIG. 10*k* is a screen page 1038 opened by clicking on the "Tricuspid, Pulmonic, IVC" tab 321 on the start-up screen page 301. This screen page 1038 has option boxes 1039 for entry of comments specific to the tricuspid valve, pulmonic valve and inferior vena cava, and text boxes 1040 to display grammatically correct sentences reflecting the user's selections from the option boxes 1039. The sentences are constructed in the text boxes 1040 as the selections are made in the option boxes 1039 and are intended to appear in the final report with minor editing if needed.

FIG. 10*l* is a screen page 1041 opened by clicking on the "Aortic Valve" tab 322 on the start-up screen page 301. This screen page 1041 has option boxes 1042 for entry of comments specific to aortic valve structure, aortic stenosis data and aortic regurgitation data, and text boxes 1043 to display grammatically correct sentences reflecting the user's selections from the option boxes 1042. The sentences are constructed in the text boxes 1043 as the selections are made in the option boxes 1042 and are intended to appear in the final report with minor editing if needed.

FIG. 10*m* is a screen page 1044 opened by clicking on the "ASD, PFD, VSD" tab 323 on the start-up screen page 301. This screen page 1044 has option boxes 1045 for entry of comments specific to atrial septal defect (ASD), patent foramen ovale (PFO), and ventricular septal defect (VSD). The selection of any of the option boxes 1045 will generate a grammatically correct sentence reflecting the user's selections from the option boxes 1045 and are intended to appear in the final report with minor editing if needed.

FIG. 10*n* is a screen page 1046 opened by clicking on the "M-Mode and Doppler LV signs" tab 324 on the start-up screen page 301. This screen page 1046 has option boxes 1047 for entry of comments specific to mitral valve signs of left ventricular systolic dysfunction, aortic and aortic valve signs of left ventricular systolic dysfunction, mitral Doppler signs of left ventricular diastolic dysfunction and other Doppler signs, and text boxes 1048 to display grammatically correct sentences reflecting the user's selections from the option boxes 1047. The sentences are constructed in the text boxes 1048 as the selections are made in the option boxes 1047 and are intended to appear in the final report with minor editing if needed.

FIG. 10*o* is a screen page 1049 opened from screen page 1046 by clicking on the "Show Doppler Guide" command button 325 on the start-up screen 301 which is shown on the various tabbed screen pages accessed from the start-up screen 301, such as screen page 1046 shown on FIG. 10*n*. The "Show Doppler Guide" command button 325 may also be used when the "Pericardium" screen page 1034 is open. As shown in FIG. 10*o*, there are three sections under the "Show Doppler Guide" command button 325. One of these three is shown as screen page 1049 under the "Restriction" tab 1050. A second is shown as screen page 1051 in FIG. 10*p* under the "Diastolic Doppler" tab 1052. A third is shown as screen page 1053 in FIG. 10*q* under the "Constriction" tab 1054. The three diagrams shown on screen pages 1049, 1051 and 1053 are intended to help the user in his analysis.

FIG. 10r is a screen page 1055 opened from the "Pericardium" screen page 1034 by clicking on the "Show Doppler Guide" command button 325 and illustrates one of the three sections under this command button, namely the screen page 1055 under the "Restriction" tab 1056. A second is shown as screen page 1057 in FIG. 10s under the "Diastolic Doppler" tab 1058. A third is shown as screen page 1059 in FIG. 10t under the "Constriction" tab 1060. The three diagrams shown on screen pages 1055, 1057 and 1059 are intended to help the user in his analysis.

FIG. 10u is a screen page 1061 opened by clicking on the "Abnormal Septal Motion" tab 326 on the start-up screen page 301. This screen page 1061 has option boxes 1062 for entry of comments specific to abnormal septal motion and text boxes 1063 to display grammatically correct sentences reflecting the user's selections from the option boxes 1062. The sentences are constructed in the text boxes 1063 as the selections are made in the option boxes 1062 and are intended to appear in the final report with minor editing if needed.

FIG. 10v is a screen page 1064 opened by clicking on the "Prosthetic Valves" tab 327 on the start-up screen page 301. This screen page 1064 has option boxes 1065 for entry of comments specific to prosthetic valves. Grammatically correct sentences reflecting the user's selections from the option boxes 1065 are accessed by clicking on the "View Prosthetic Valve Text Boxes" command button 1066 and closed by clicking on the "Hide Text Boxes" command button 1067. The sentences are constructed as the selections are made in the option boxes 1065 and can be edited directly by the user and are intended to appear in the final report.

FIG. 10w is a screen page 1068 opened by clicking on the "View Normal Doppler Values" command button 1069 on the "Prosthetic Valves" screen page 1064. This screen page 1068 provides the user with a table of normal values for common prosthetic aortic and mitral valves. Screen page 1068 is closed by clicking on command button 1069, which reverts to "Close Down Values" when the "View Normal Doppler Values" command button is clicked.

FIG. 10x is a screen page 1070 opened by clicking on the "Segmental Wall Motion" tab 328 on the start-up screen page 301 and illustrates one of the sections available under this command button, namely the screen page 1070 under the "Basic" tab 1071 which has option boxes 1072 and a text box 1073. The selection of any of the option boxes 1072 will generate a grammatically correct sentence in the text box 1073 reflecting the user's selections from the option boxes 1072 and are intended to appear in the final report with minor editing if needed. The "Segmental Wall Motion" tab 328 allows the user to select one of three different schemes to describe segmental wall motion abnormalities. The screen page 1070 under the "Basic" tab 1071 allows selection of the regions of the heart by more colloquial terms such as "Inferior Wall" or "Anterior Wall". The segments of the heart are represented by graphic color coded segment images 1074. The other two schemes are available under the "15 Segment" tab 1076 shown as screen page 1075 in FIG. 10y with graphic color coded segment images 1077, keyed to segment name option boxes 1078, or the "16 Segment" tab 1080 shown as screen page 1079 in FIG. 10z with graphic color coded segment images 1081, keyed to segment name option boxes 1082, and allow the selection of either a formal 15-segment or 16-segment classification. Screen page 1075 for the 15-segment selection or screen page 1079 for the 16-segment selection are further enhanced by clicking on any segment in the graphic color coded segment images 1077 or any segment in the graphic color coded segment images 1081 will show a line 1083 connecting the segment to its name in the segment name option boxes 1078 or 1082 respectively and will also show a line 1084 from the respective segment name option box to the corresponding segment representation in the other axis. The final tabbed section under "Segmental Wall Motion" tab 328 is the "Text" tab 1085 is a text page which will display grammatically correct sentences reflecting the user's selections from the-various option boxes as the selections are made and are intended to appear in the final report with minor editing if needed. This text page is not shown but is available to the user at any time.

FIG. 10aa is a screen page 1086 opened by clicking on the "Conclusions" tab 329 on the start-up screen page 301. This screen page 1086 has been divided into two sections, each with its own tab and screen page, beginning with the "CONCLUSIONS" tab 1087 shown on screen page 1086 shown in FIG. 10aa. On this screen page 1086 is text box 1088 labeled as "extra suggestions for favorite diagnoses" which the user entered on the maintenance form screen page 701 in text box 705. A text box 1089 for additional conclusions is provided. Text box 1090 displays all diagnoses (with ICD-9 codes) as suggested by the user's selections throughout the inventive computer-implemented method and system. A control button 1091 is provided to add the additional conclusions from text box 1089 to the text box 1090, and a control button 1092 is provided to add a selection from text box 1088 to the text box 1090. A text box 1093 is provided for discarding or reinserting diagnoses in text box 1090 by control buttons 1094 and 1095. Once the user is satisfied with the list in text box 1090, the list can be copied into a final conclusion text box 1096 by the control button 1097. The list in text box 1096 can be edited if desired. The "Write Report" button 1098 writes a final report in a computer software system such as Microsoft Word®. The "Write Print Save" button 1099 can be used in place of "Write Report" button 1098, and this button 1099 writes the report, prints it to a default printer and saves it. These functions can also be performed with the "Print" bottom 331 and the "Save" button 332. The user can view the report by clicking on the "Look at Report" button 1990. A "Sign Report" button 1991 is provided for electronic signature. The "Exit" button 333 closes the program.

The second section under the "Conclusions" tab 329 on the start-up screen page 301 is opened by clicking on the "User Controls and Free Text" tab 1992 and is shown in FIG. 10ab as screen page 1993. This screen page 1993 contains any entries from boxes 706 on the maintenance form screen page 701 and also allows the entry of any free text that the user may desire.

FIGS. 11a through 11k are the individual conditions screens opened by clicking on the "Show Individual Conditions Pages" control button 330 on the start-up screen page 301. These individual condition screen pages are devoted to a specific disease entity and allow the user, having identified the presence of a certain condition by a standard anatomical-based approach through the use of anatomical-based screen pages illustrated in FIGS. 10a through 10z, to shift to a disease-oriented screen page and be presented with options reminding the user of all the various possible echo findings in that disease. This allows the user to amplify the description of the echo in specific areas and give a more meaningful echo report.

Figure 11A:
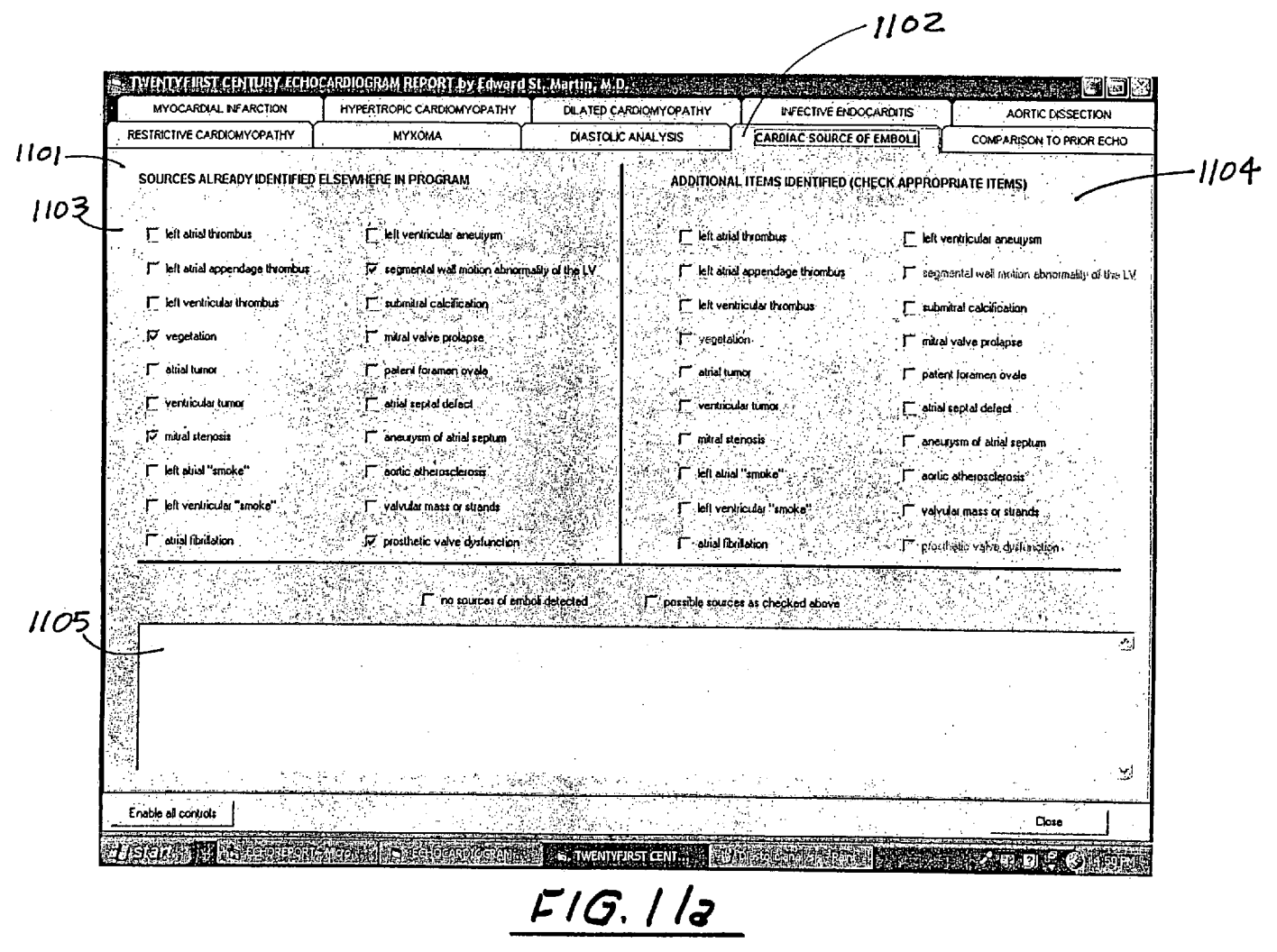

FIG. 11a is a screen page 1101 opened by clicking on the "CARDIAC SOURCE OF EMBOLI" tab 1102. This screen 1101 has an option box 1103 with an extensive list for entry of comments related to sources already identified elsewhere in program, and an option box 1104 for entry of additional items identified. The listings in these option boxes 1103 and 1104 serve as a tutorial for the user to consider many details. A text box 1105 is provided to display grammatically correct sentences reflecting the user's selections from the option boxes 1103 and 1104. The sentences are constructed in the text box 1105 as the selections are made in the option boxes 1103 and 1104 and are intended to appear in the final report with minor editing if needed.

FIG. 11*b* is a screen page 1106 opened by clicking on the "AORTIC DISSECTION" tab 1107. This screen 1106 has an option box 1108 for entry of comments related to Underlying Pathology, Anatomic Features, Functional Features and Complications and an option box 1109 for entry of comments related to Debakey Classification. A text box 1110 is provided to display grammatically correct sentences reflecting the user's selections from the option boxes 1108 and 1109. The sentences are constructed in the text box 1110 as the selections are made in the option boxes 1108 and 1109 and are intended to appear in the final report with minor editing if needed.

Figure 11C:
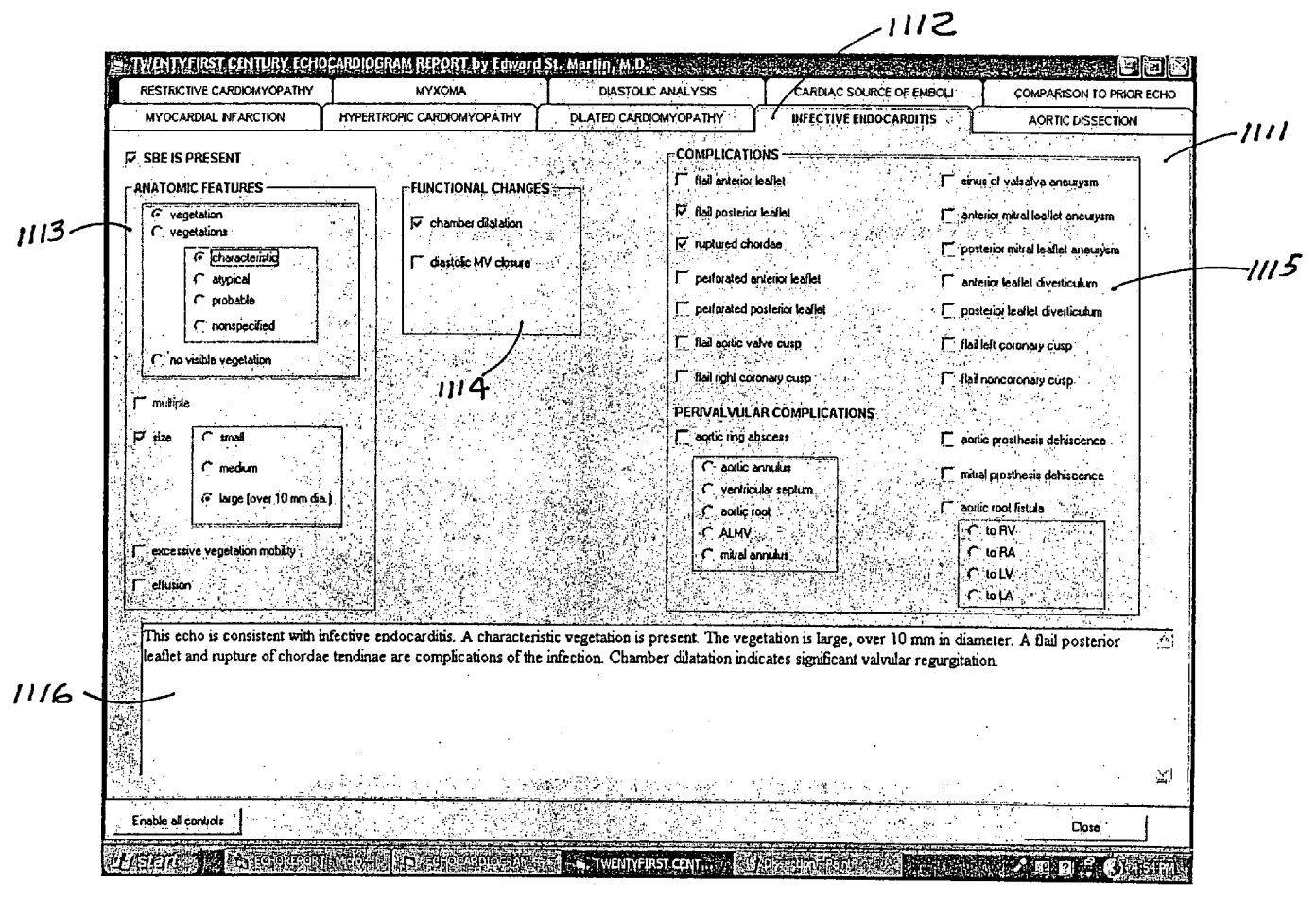

FIG. 11*c* is a screen page 1111 opened by clicking on the "INFECTIVE ENDOCARDITIS" tab 1112. This screen 1111 has an option box 1113 for entry of comments related to Anatomic Features, an option box 1114 for entry of comments related to Functional Changes, and an option box 1115 for entry of comments related to Complications. A text box 1116 is provided to display grammatically correct sentences reflecting the user's selections from the option boxes 1113, 1114 and 1115. The sentences are constructed in the text box 1116 as the selections are made in the option boxes 1113, 1114 and 1115 and are intended to appear in the final report with minor editing if needed.

Figure 11D:
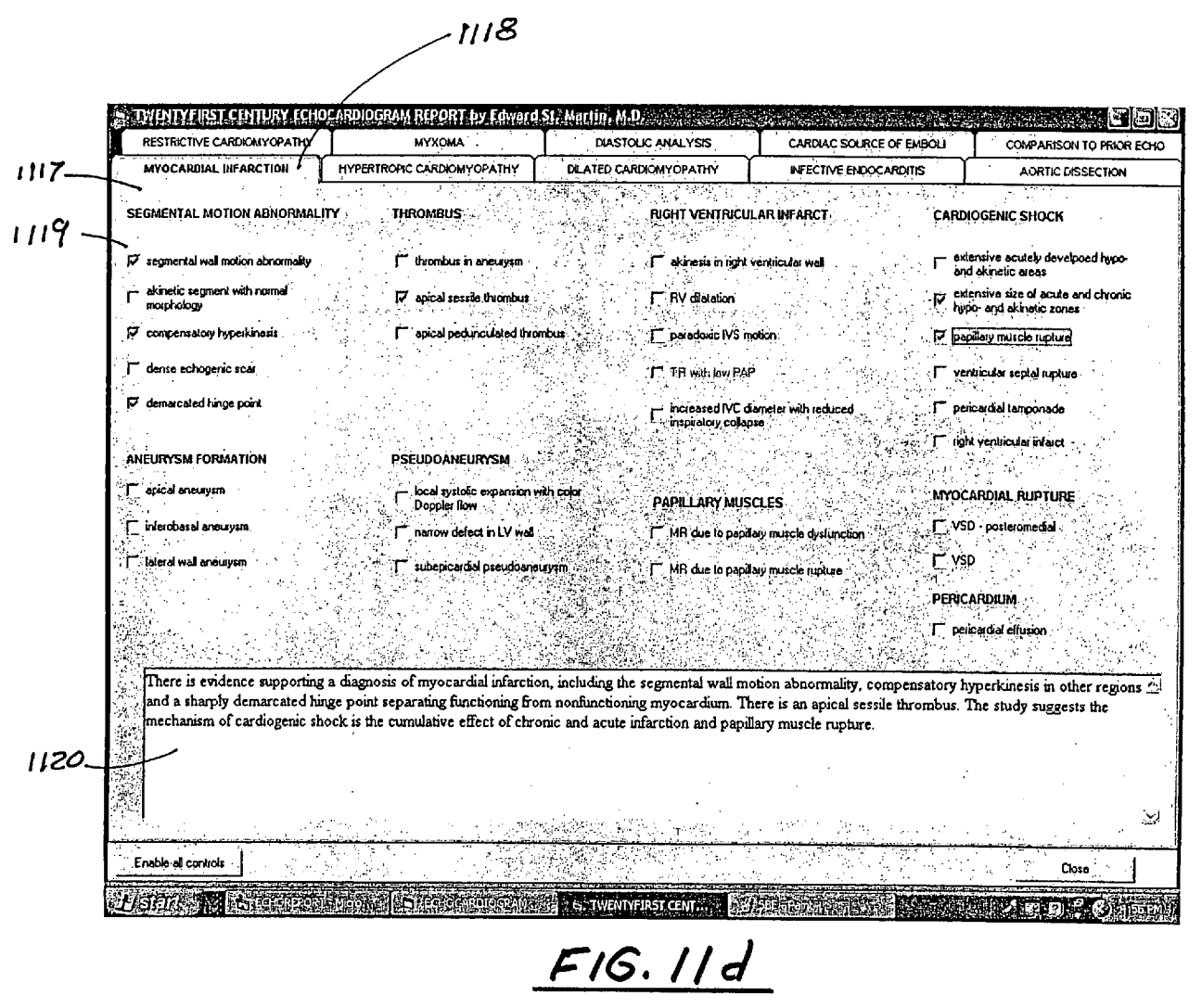

FIG. 11*d* is a screen page 1117 opened by clicking on the "MYOCARDIAL INFARCTION" tab 1118. This screen 1117 has an option box 1119 for entry of comments related to Segmental Motion Abnormality, Aneurysm Formation, Thrombus, Pseudoaneurysm, Right Ventricular Infarct, Papillary Muscles, Cardiogenic Shock, Myocardial Rupture and Pericardium. A text box 1120 is provided to display grammatically correct sentences reflecting the user's selections from the option box 1119. The sentences are constructed in the text box 1120 as the selections are made in the option box 1119 and are intended to appear in the final report with minor editing if needed.

Figure 11E:
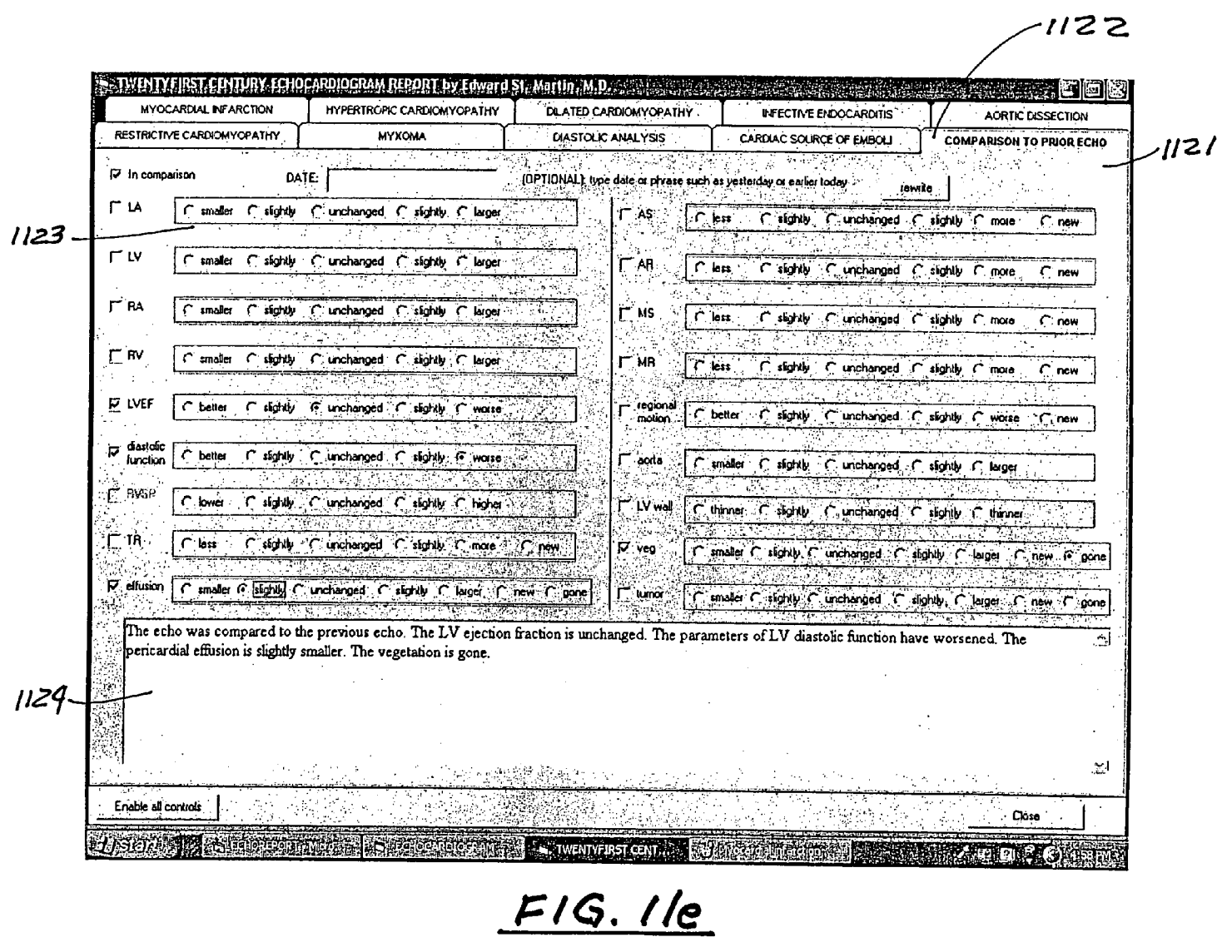

FIG. 11*e* is a screen page 1121 opened by clicking on the "COMPARISON TO PRIOR ECHO" tab 1122. The screen page 1121 lists core aspects of the heart and provides comparison selection boxes 1123 for each. For each, the user can indicate whether a certain feature is new, has gone away, is unchanged, or slightly or greatly changed for either the better or the worse. A text box 1124 is provided to display grammatically correct sentences reflecting the user's selections from the comparison selection boxes 1123. The sentences are constructed in the text box 1124 as the selections are made in the comparison selection boxes 1123 and are intended to appear in the final report with minor editing if needed.

Figure 11F:
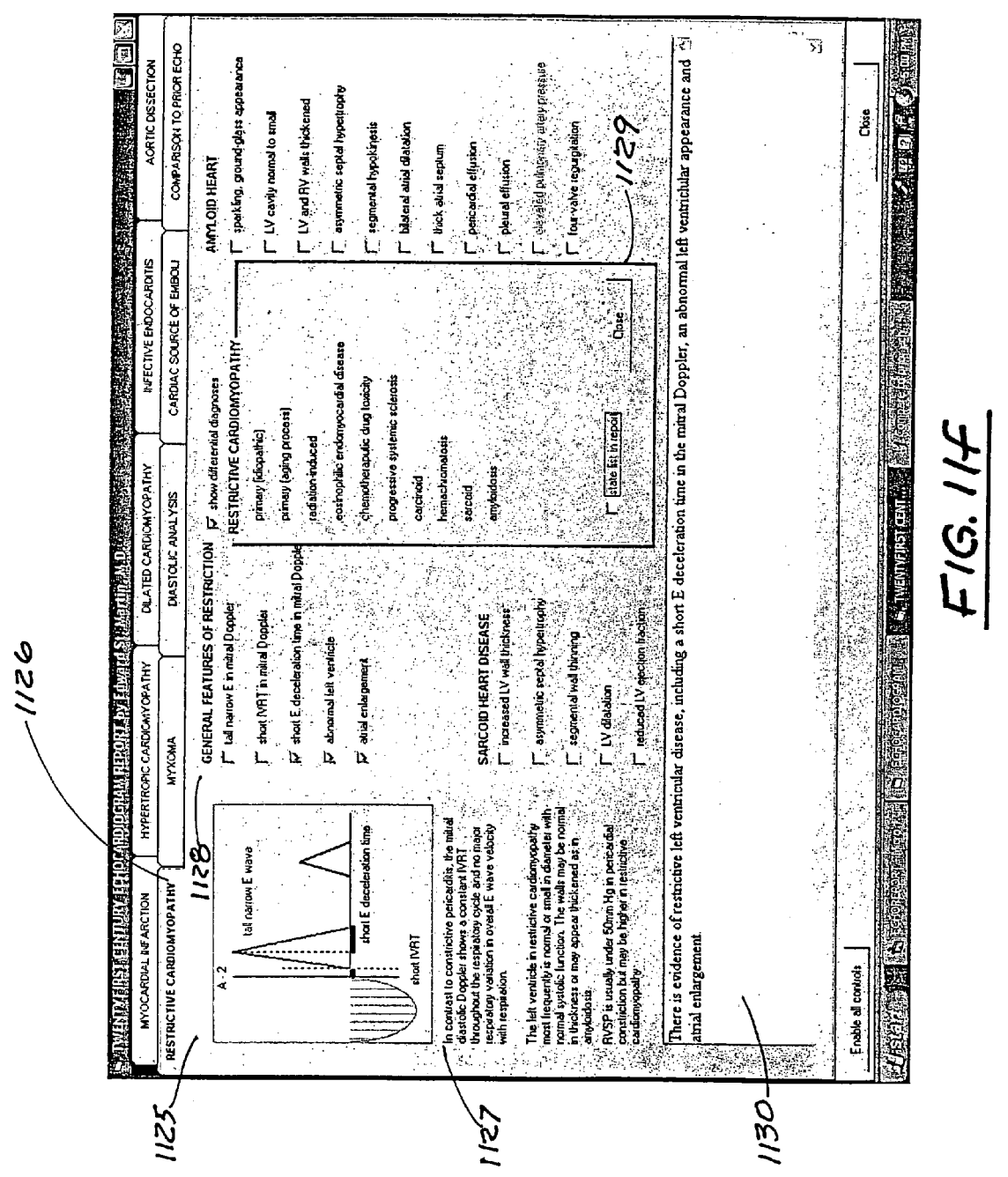

FIG. 11*f* is a screen page 1125 opened by clicking on the "RESTRICTIVE CARDIOMYOPATHY" tab 1126. This screen page 1125 provides a reference Doppler graphic and comments 1127 specific to restrictive cardiomyopathy. This screen page 1125 provides option boxes 1128 for entry of comments related to General Features of Restriction, Sarcoid Heart Disease and Amyloid Heart, and an option box 1129 for comments specific to Restrictive Cardiomyopathy. A text box 1130 is provided to display grammatically correct sentences reflecting the user's selections from the option boxes 1128 and 1129. The sentences are constructed in the text box 1130 as the selections are made in the comparison selection boxes 1128 and 1129 and are intended to appear in the final report with minor editing if needed.

FIG. 11*g* is a screen page 1131 opened by clicking on the "MYXOMA" tab 1132. This screen 1131 has an option box 1133 for entry of comments related to Left Atrium, Bilateral Atrial Myxomas, Right Atrium, Left Ventricle and Right Ventricle. A text box 1134 is provided to display grammatically correct sentences reflecting the user's selections from the option box 1133. The sentences are constructed in the text box 1134 as the selections are made in the option box 1133 and are intended to appear in the final report with minor editing if needed.

FIG. 11*h* is a screen page 1135 opened by clicking on the "HYPERTROPIC CARDIOMYOPATHY" tab 1136. This screen 1135 has an option box 1137 for entry of comments related to Anatomic, Functional and IHSS categories. A text box 1138 is provided to display grammatically correct sentences reflecting the user's selections from the option box 1137. The sentences are constructed in the text box 1138 as the selections are made in the option box 1137 and are intended to appear in the final report with minor editing if needed.

FIG. 11*i* is a screen page 1139 opened by clicking on the "DILATED CARDIOMYOPATHY" tab 1140. This screen 1139 has an option box 1141 for entry of comments related to Anatomic, Functional and Other Feature categories. A text box 1142 is provided to display grammatically correct sentences reflecting the user's selections from the option box 1141. The sentences are constructed in the text box 1142 as the selections are made in the option box 1141 and are intended to appear in the final report with minor editing if needed.

Figure 11K:
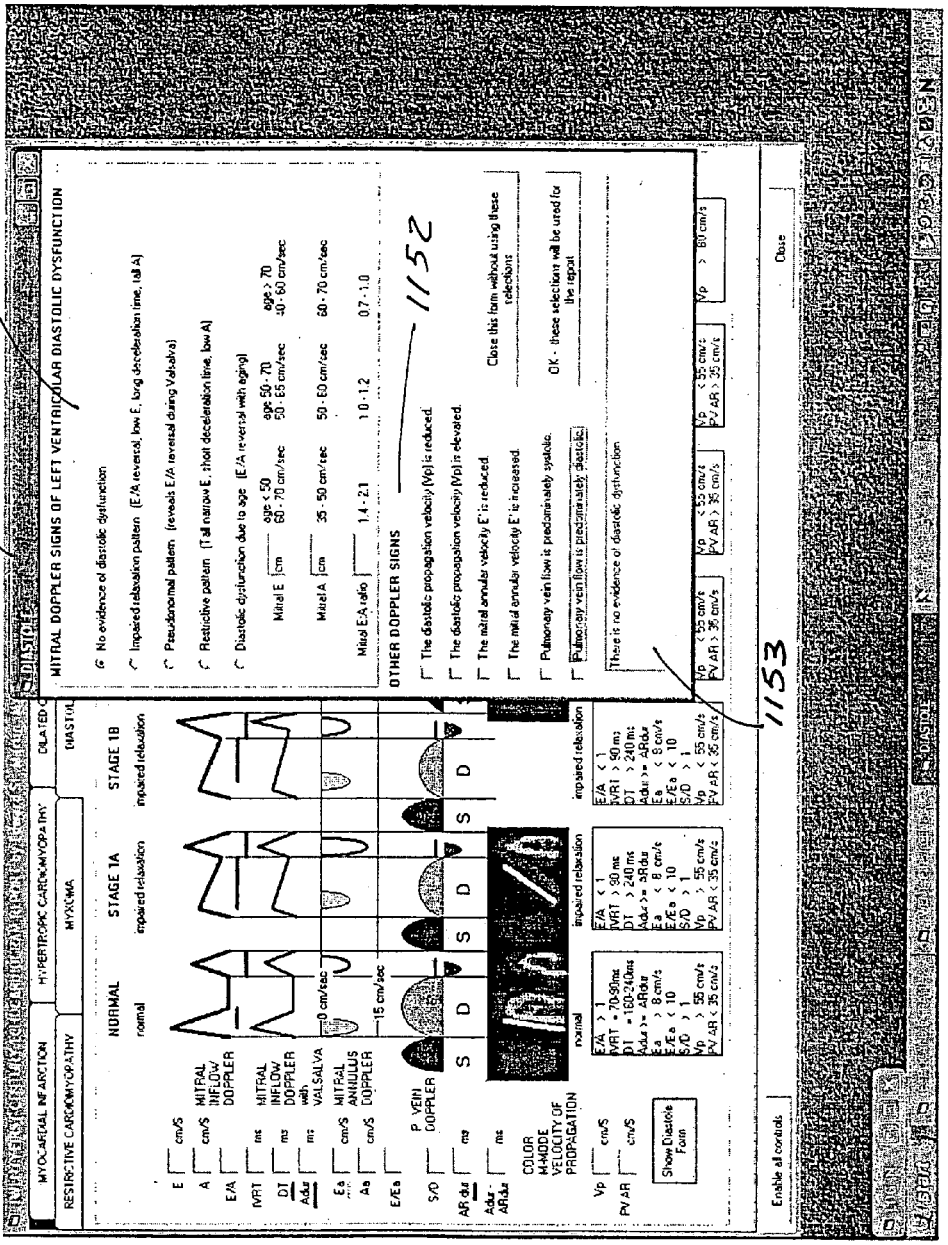

FIG. 11*j* is a screen page 1143 opened by clicking on the "DIASTOLIC ANALYSIS" tab 1144. This screen page 1143 provides the user with a column 1145 of patient specific data taken from the new patient database form 501 and/or the technician's form screen page 601. In order to assist the user in making a meaningful analysis of the patient specific data, graphic Doppler illustrations 1146 and a corresponding table 1147 of data parameters are provided for various degrees of disease state beginning with Normal, and continuing with Stage 1A (impaired relaxation), Stage 1B (impaired relaxation), Stage 2 (pseudonormal), Stage 3 (reversible restriction), Stage 4 (irreversible restriction) and Constriction (pericardial constriction). Where the patient specific data illustrated in column 1145 exceeds or surpasses the data parameters shown in the table 1147, that data point is highlighted with a marker 1148 to assist the user. There is also a "Show Diastole Form" control button 1149 on screen page 1143 which opens a "Diastole" screen page 1150 as shown in FIG. 11*k*. On "Diastole" screen page 1150 is an option box 1151 titled "Mitral Doppler Signs of Left Ventricular Diastolic Dysfunction" and an option box 1152 for Other Doppler Signs. A text box 1153 is also provided to display grammatically correct sentences reflecting the user's selections from the option boxes 1151 and 1152. The sentences are constructed in the text box 1153 as the selections are made in the option boxes 1151 and 1152 and are intended to appear in the final report with minor editing if needed.

FIG. 12 illustrates an Echocardiogram Report 1201 generated by the inventive computer-implemented method and computer-readable storage medium by clicking the "Write Print Save" button 1099 on the "Conclusions" screen page 1086 shown in FIG. 10*aa*. The report is in final form with grammatically correct sentences and the report also contains a table of measurements and calculations in compact form, omitting any data fields not used.

Figure 13:
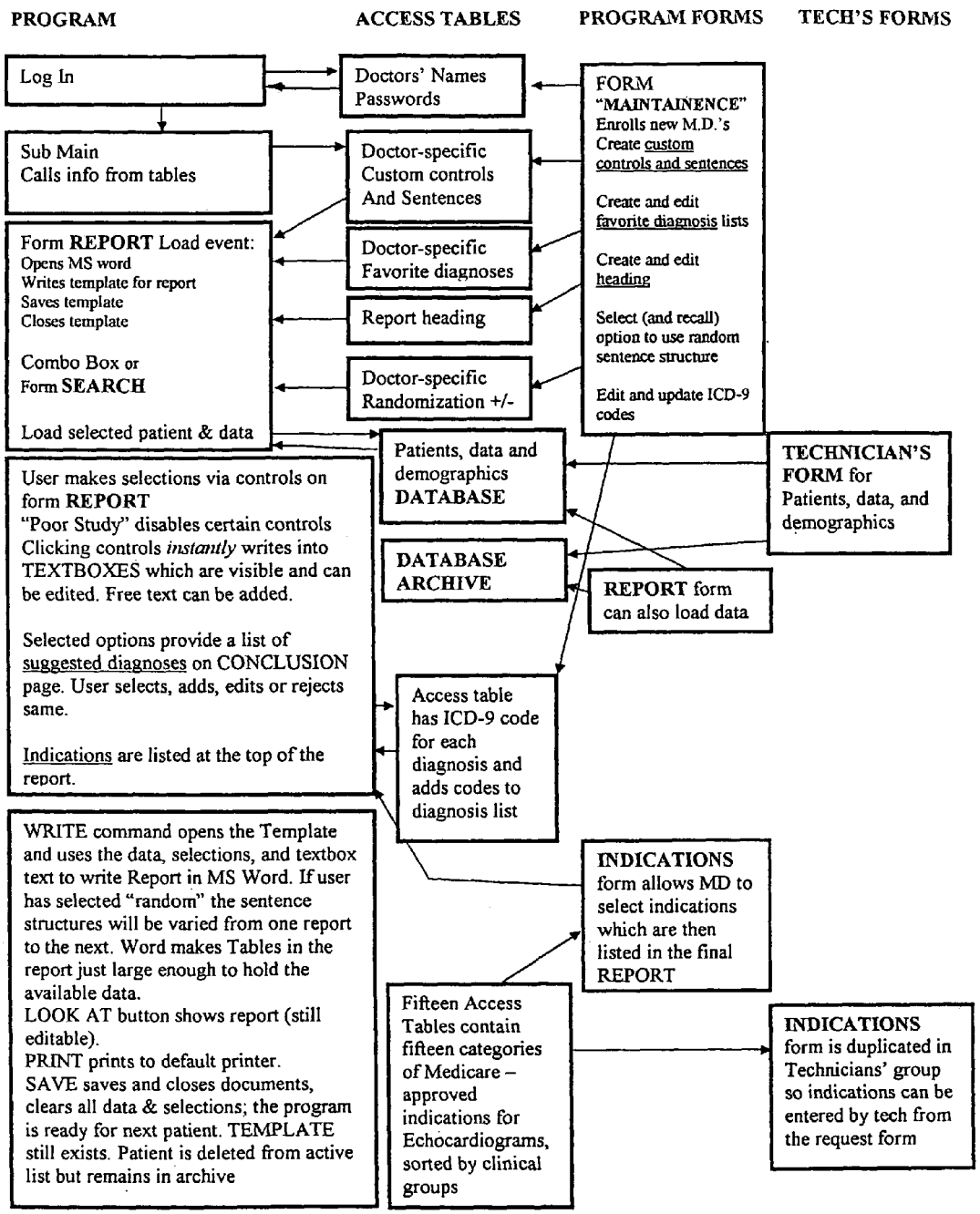
FIG. 13 is a flow diagram of the inventive computer-implemented method and computer-readable Storage medium for generating a medical report for a patient from an echocardiogram.

FIG. 13, a flow diagram of the inventive computer-implemented method and computer-readable storage medium for generating a medical report for a patient from an echocardiogram, illustrates the various steps and possibilities available to a user of the inventive computer-readable storage medium and the method performed by a computer under the instructions provided by the inventive computable readable storage medium.

As defined herein, a computer-readable storage medium is any article of manufacture that contains data that can be read by a computer or a carrier wave signal carrying data that can be read by a computer. For example, the inventive computer-readable storage medium for generating a medical report for a patient from an echocardiogram may be distributed on magnetic media, such as a floppy disk, flexible disk, hard disk, reel-to-reel tape, cartridge tape and cassette tape; optical media, such as a CD-ROM and writable compact disk; and paper media, such as punched cards and paper tape; or on a carrier wave signal received through a network, wireless network, or modem, including radio-frequency signals and infrared signals.

Figure 14A:
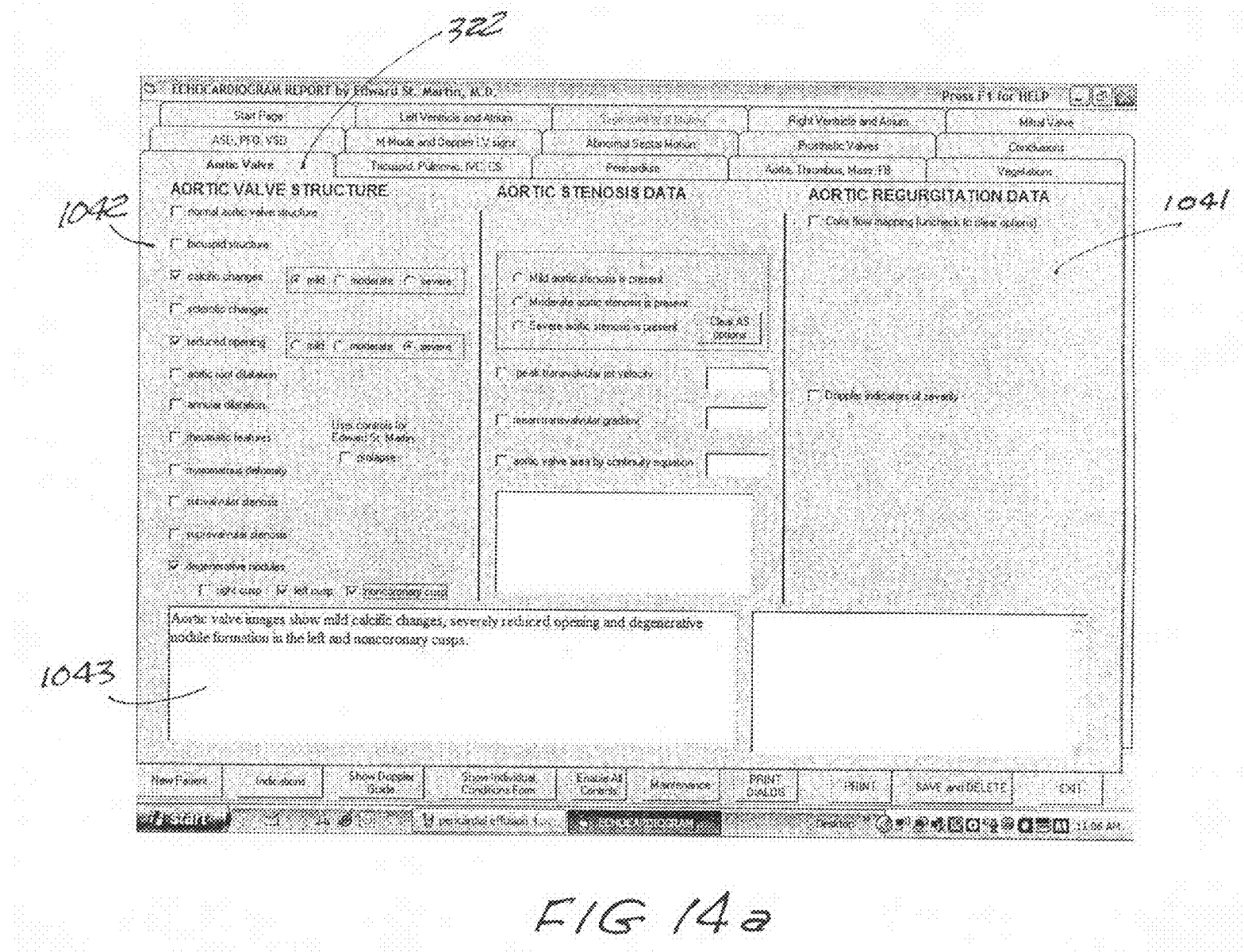
Figure 14B:
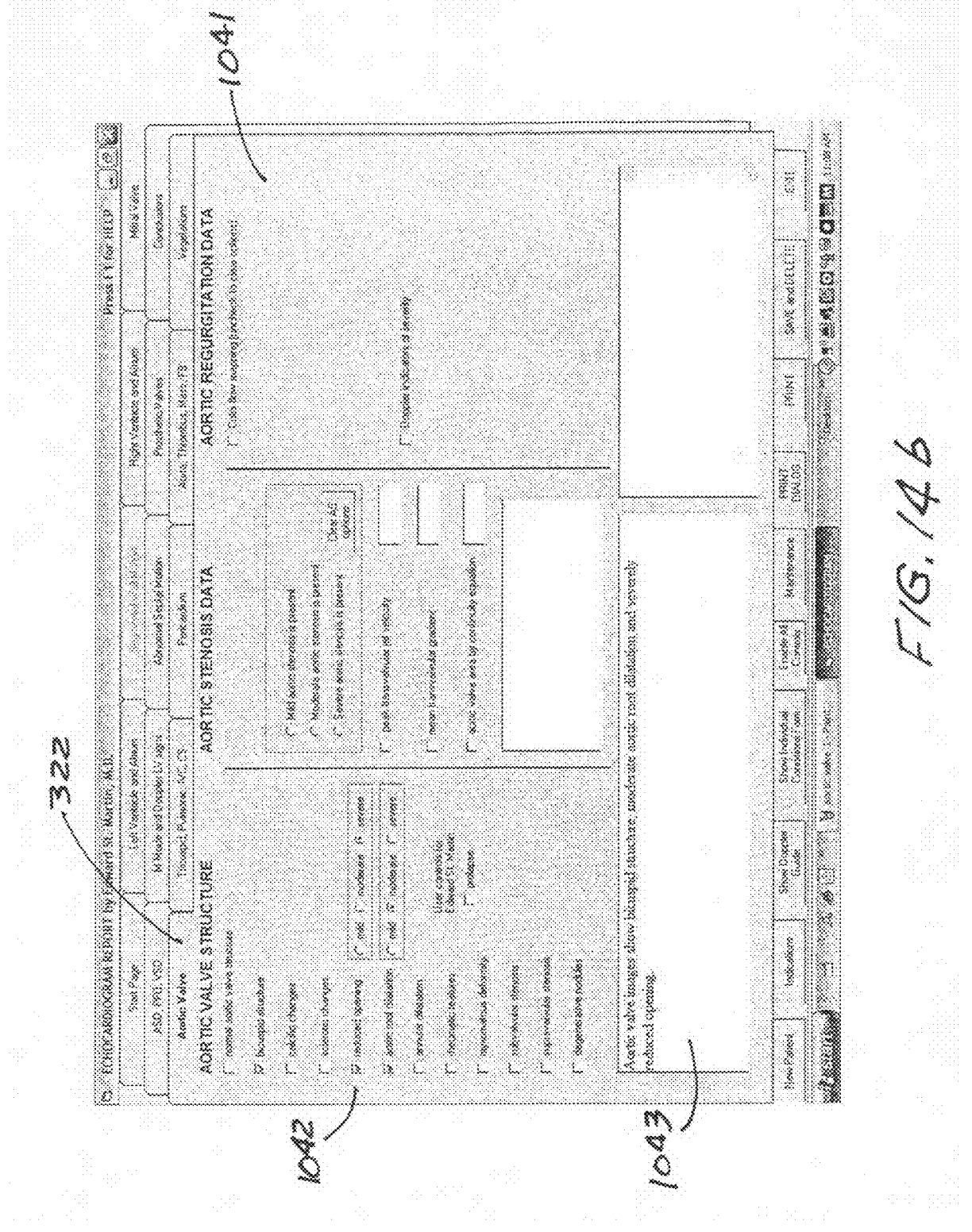

FIGS. 14a and 14b are both screen pages 1041 opened by clicking on the "Aortic Valve" tab 322 on the start-up screen page 301, and as also shown in FIG. 10l. In FIG. 14a, several option boxes 1042 have been selected and the text box 1043 shows the generation of complete grammatically complex sentences in response to the option boxes selected. In this example, the text box 1043 reads, "Aortic valve images show mild calcific changes, severely reduced opening and degenerative nodule formation in the left and noncoronary cusps." In FIG. 14b, alternative option boxes 1042 have been selected and the text box 1043 reads, "Aortic valve images show bicuspid structure, moderate aortic root dilatation and severely reduced opening."

Figure 15A:
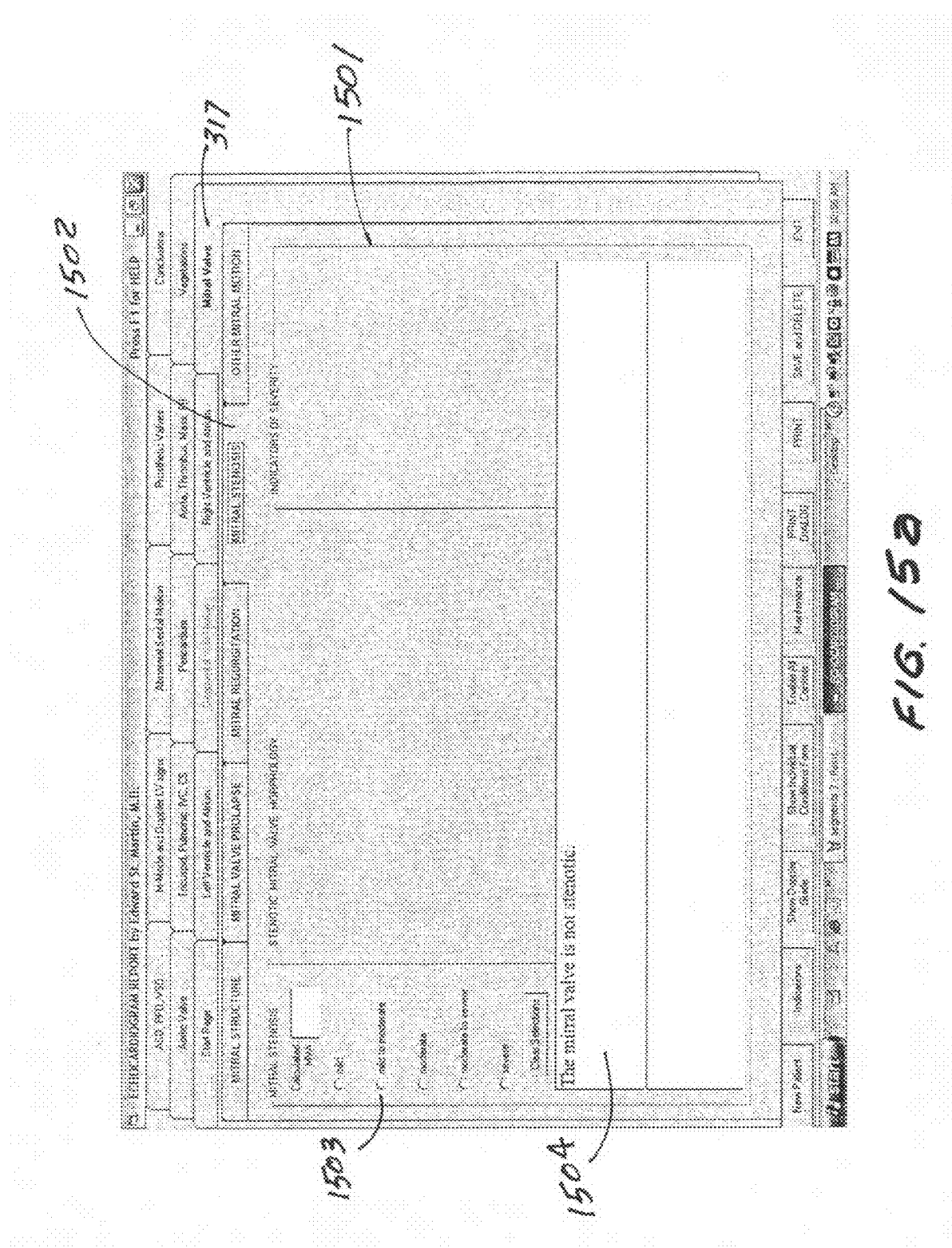
Figure 15B:
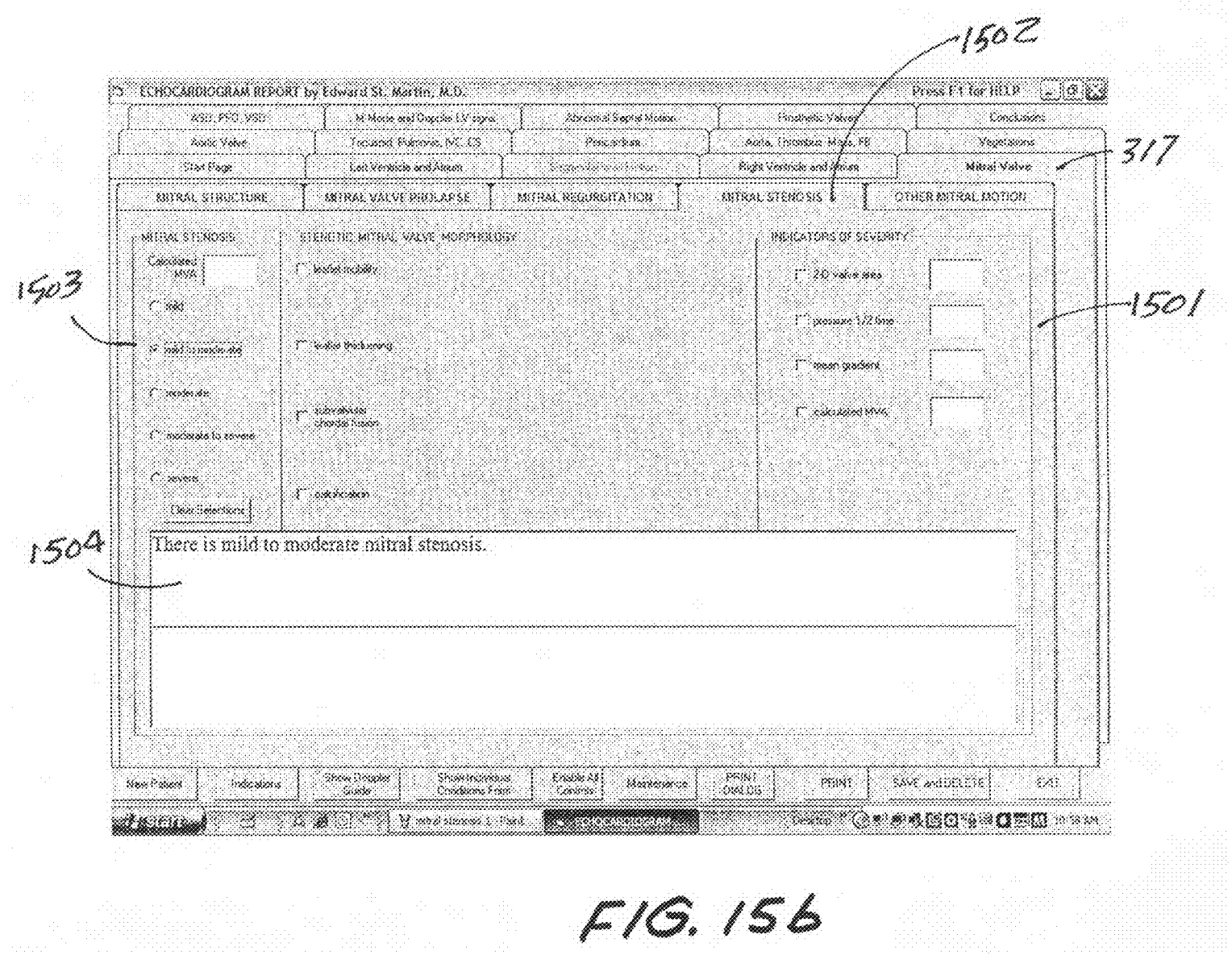
Figure 15C:
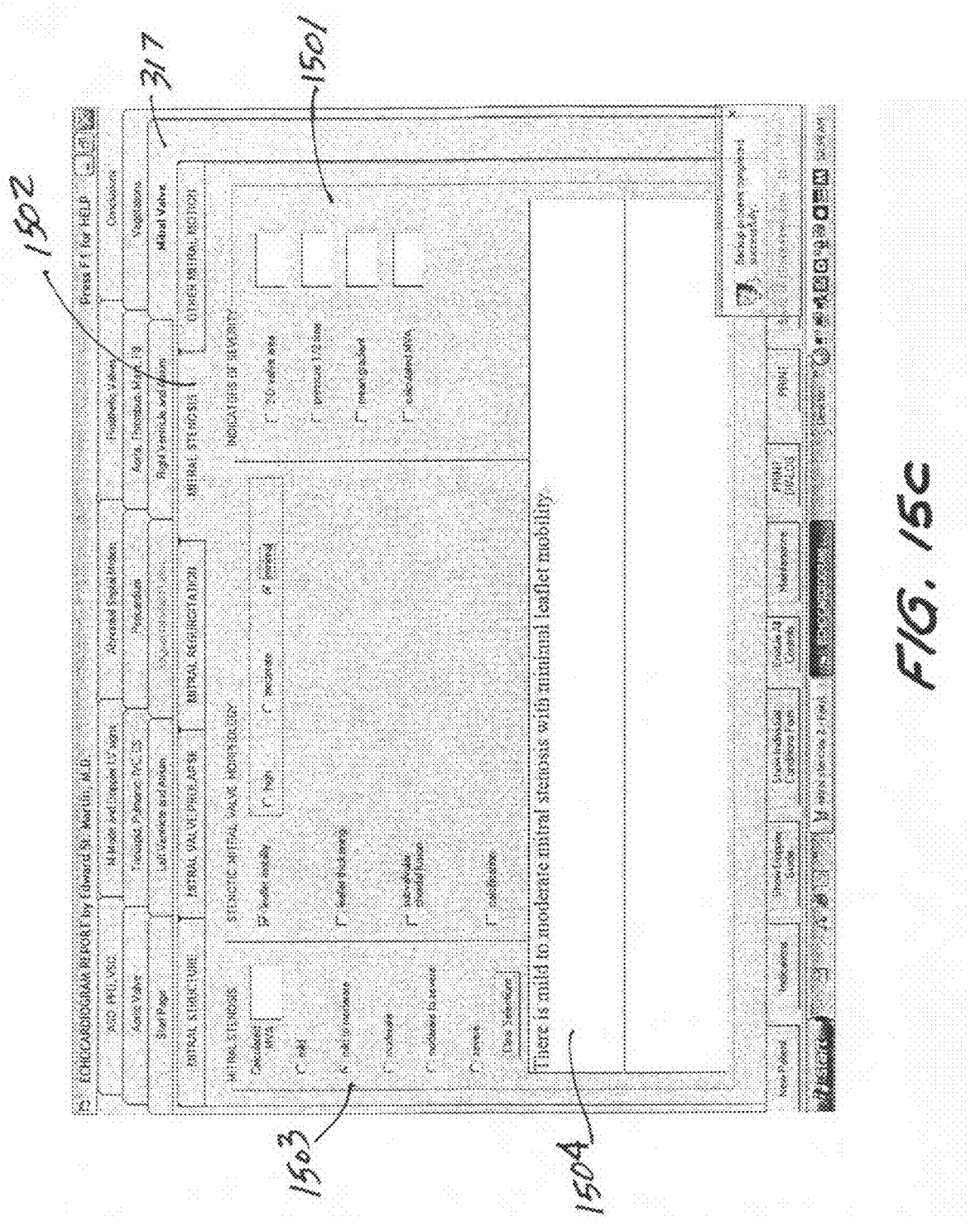
Figure 15D:
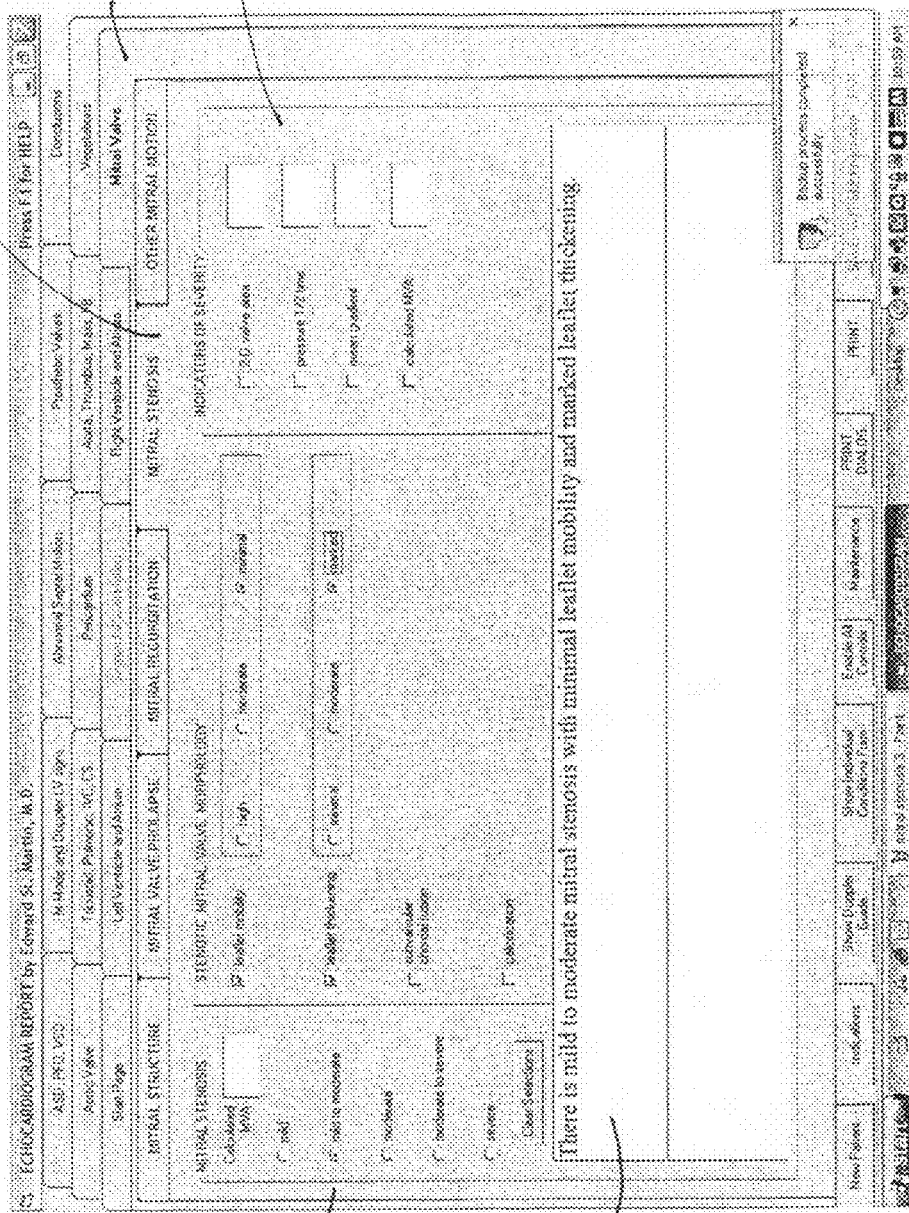
Figure 15E:
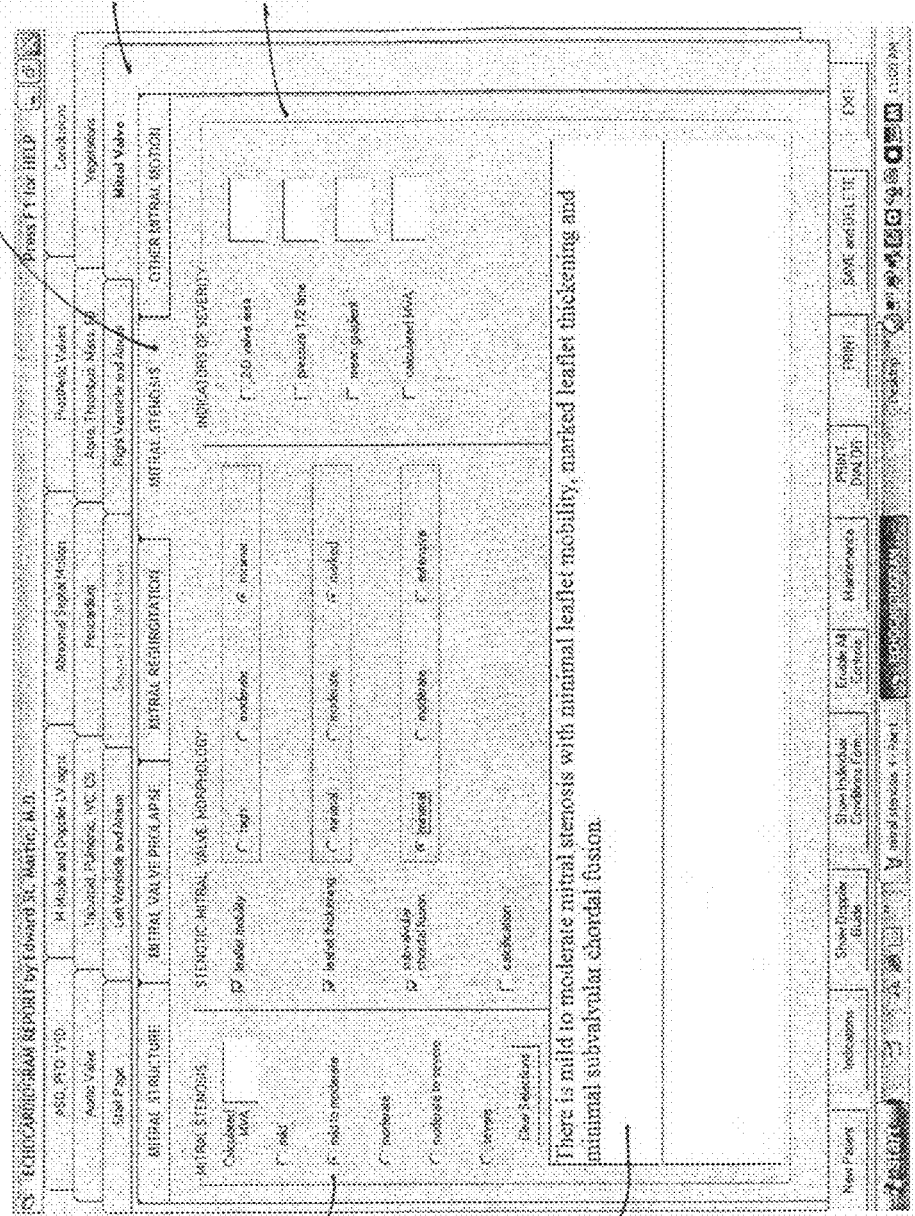

FIGS. 15a through 15e are all screen pages 1501 opened by clicking on the "Mitral Stenosis" tab 1502 after clicking on the "Mitral Valve" tab 317 and making selections on the option boxes 1503. The text box 1504 shows the generation of complete grammatically complex sentences in response to the option boxes selected. In FIG. 15a, no option boxes 1503 were selected and the text box 1504 reads simply, "The mitral valve is not stenotic." However, on FIG. 15b, several option boxes 1503 were selected and the text box 1504 now reads, "There is mild to moderate mitral stenosis." Going further, on FIG. 15c, additional option boxes 1503 were selected and the text box 1504, now reads, "There is mild to moderate mitral stenosis with minimal leaflet mobility." Additional option box 1503 selections shown on FIG. 15d causes the text box 1504 to read, "There is mild to moderate mitral stenosis with minimal leaflet mobility and marked leaflet thickening." An alternative option box 1503 selection shown on FIG. 15e, automatically changes the text box 1504 to read, There is mild to moderate mitral stenosis with minimal leaflet mobility and marked leaflet thickening and minimal subvalvular chordal fusion."

Figure 16:
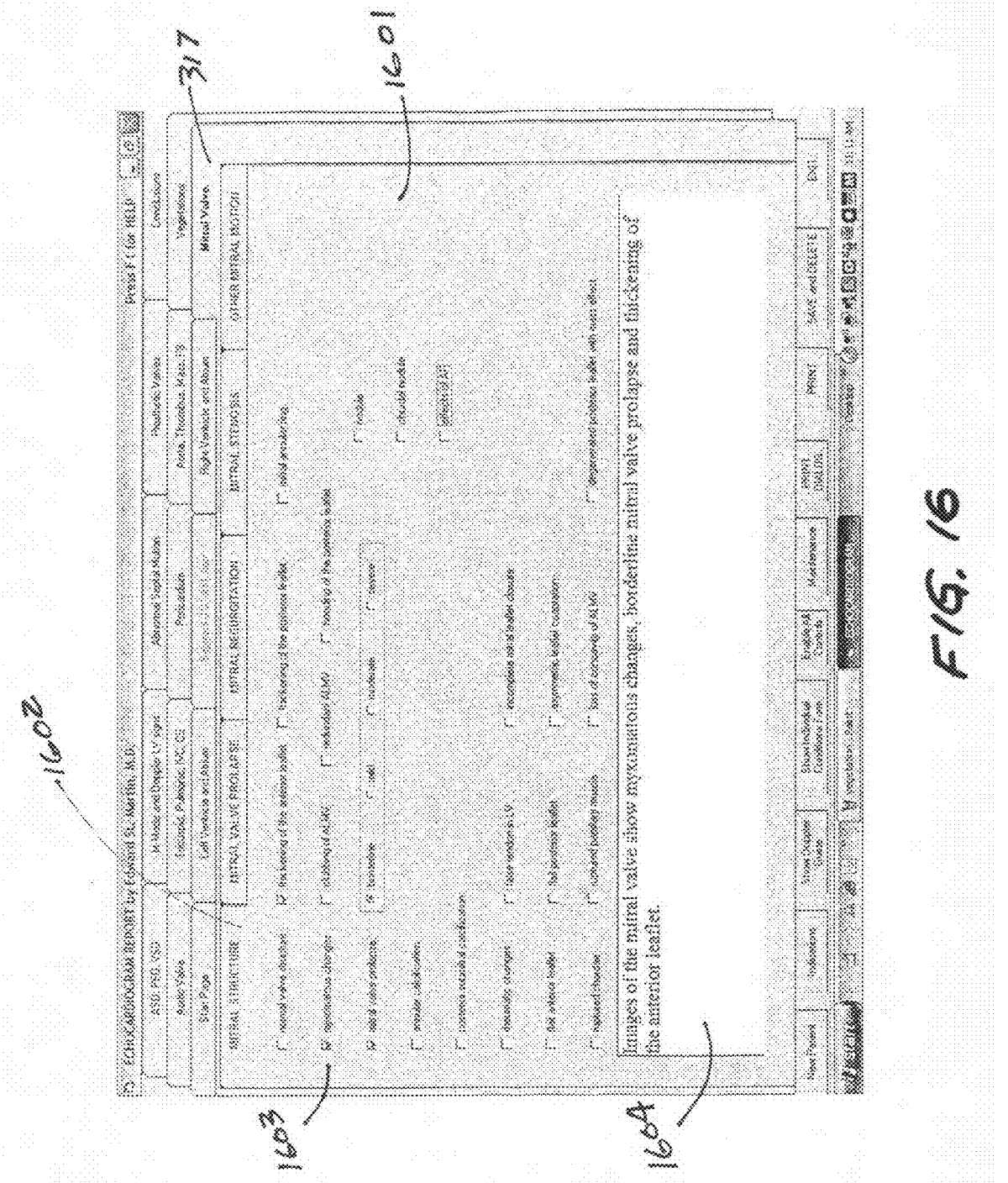

FIG. 16 is a screen page 1601 opened by clicking on the "Mitral Structure" tab 1602 after clicking on the "Mitral Valve" tab 317 and making selections on the option boxes 1603. The text box 1604 shows the generation of a complete grammatically complex sentence in response to the option boxes selected.

Figure 17B:
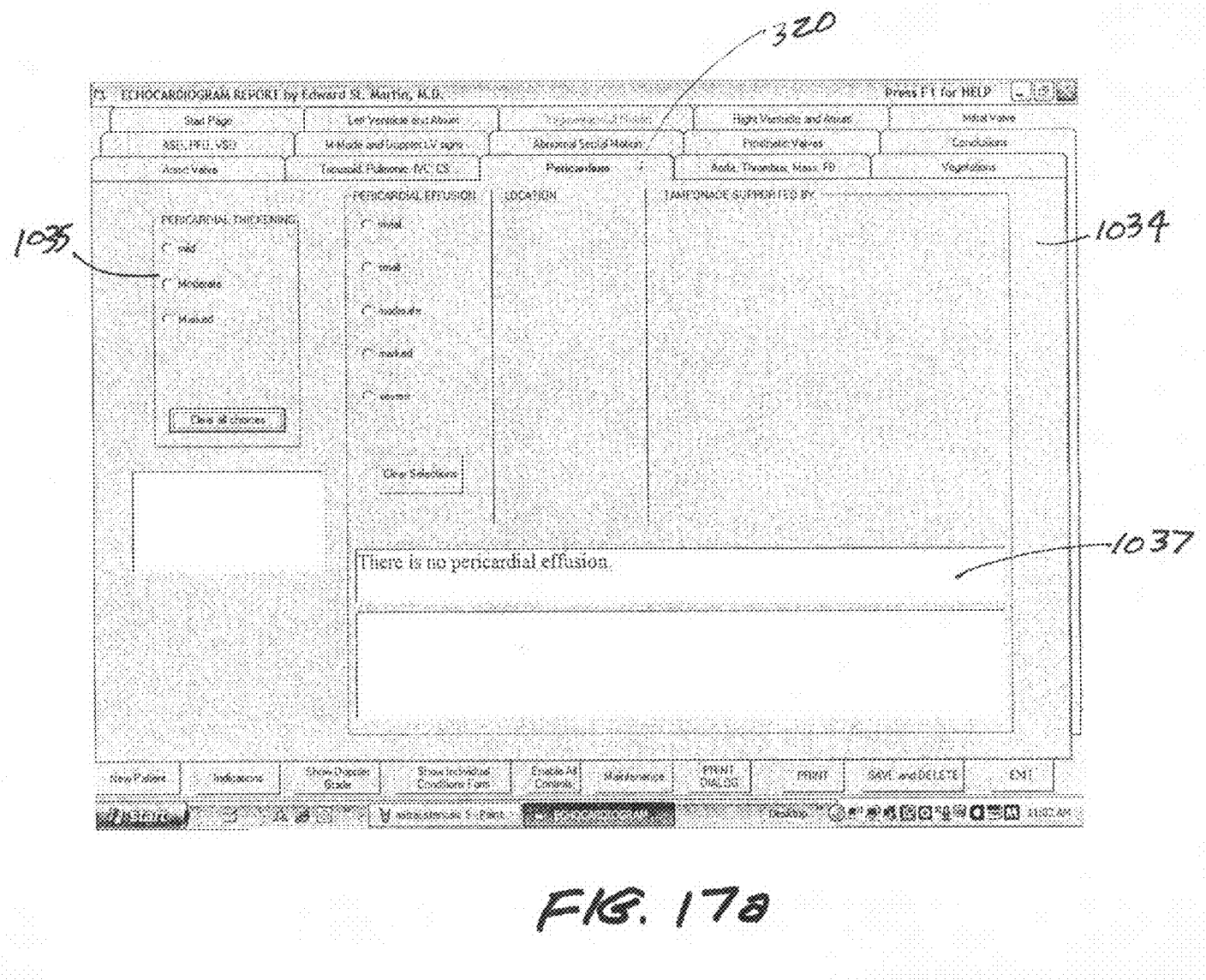
Figure 17B:
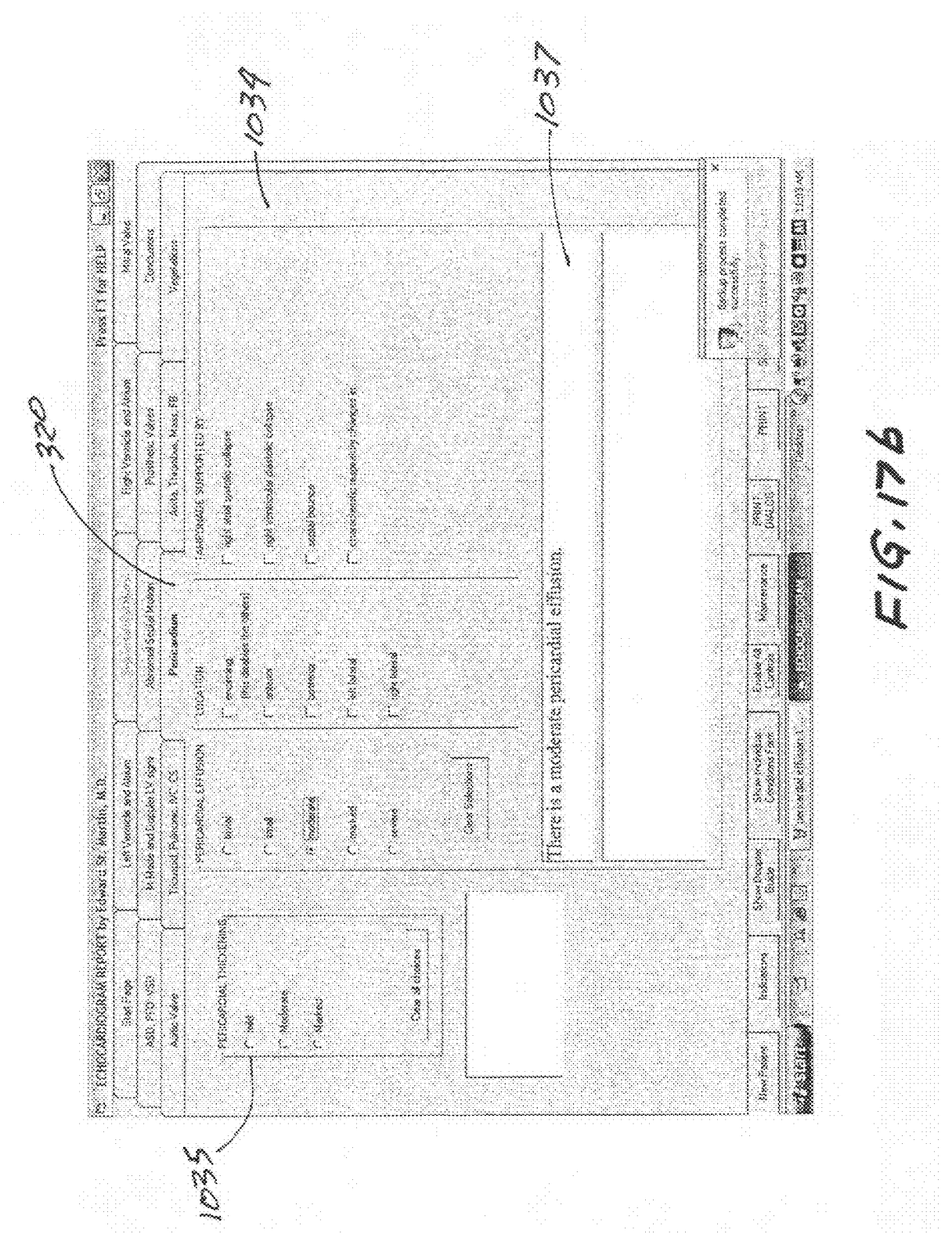
Figure 17C:
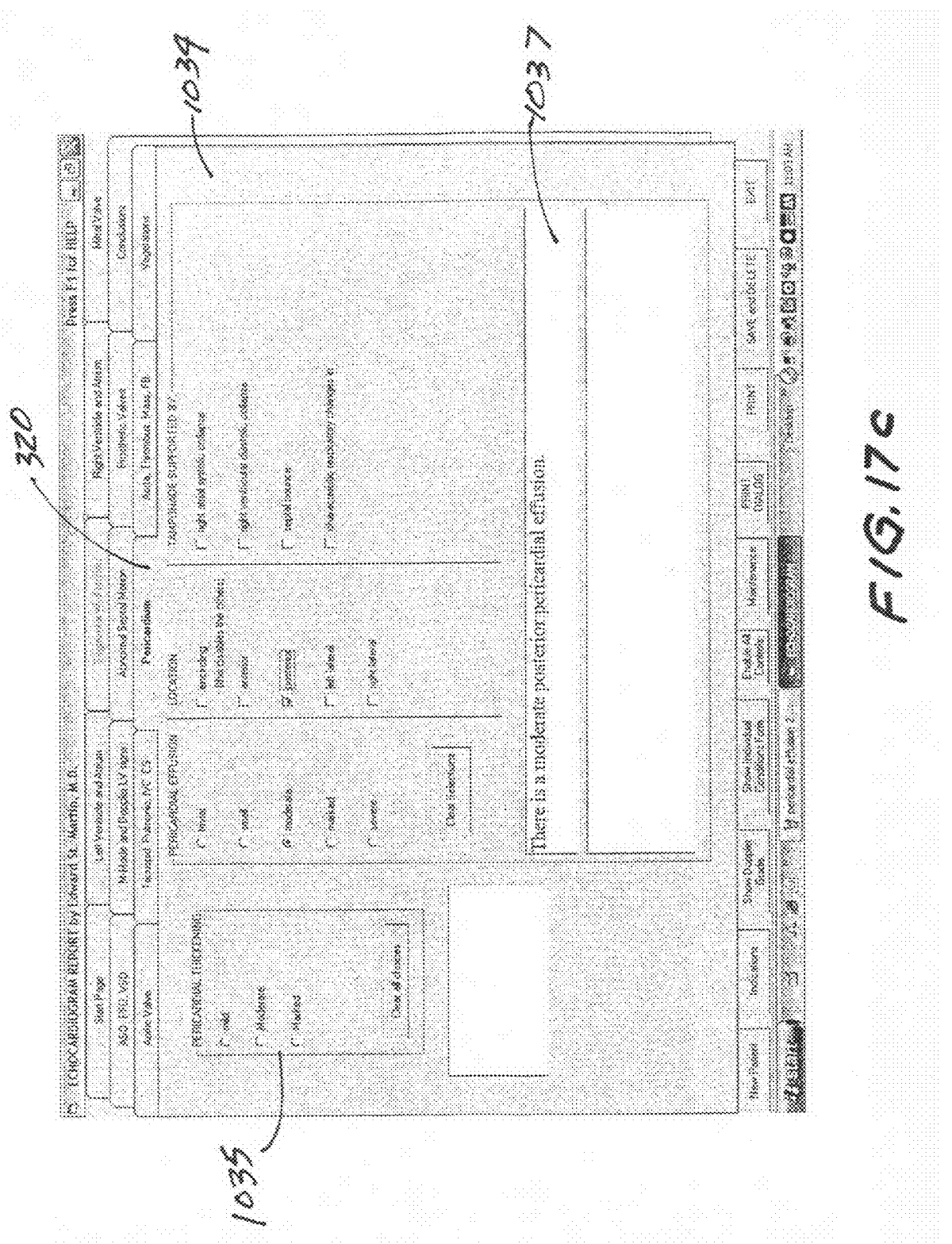
Figure 17D:
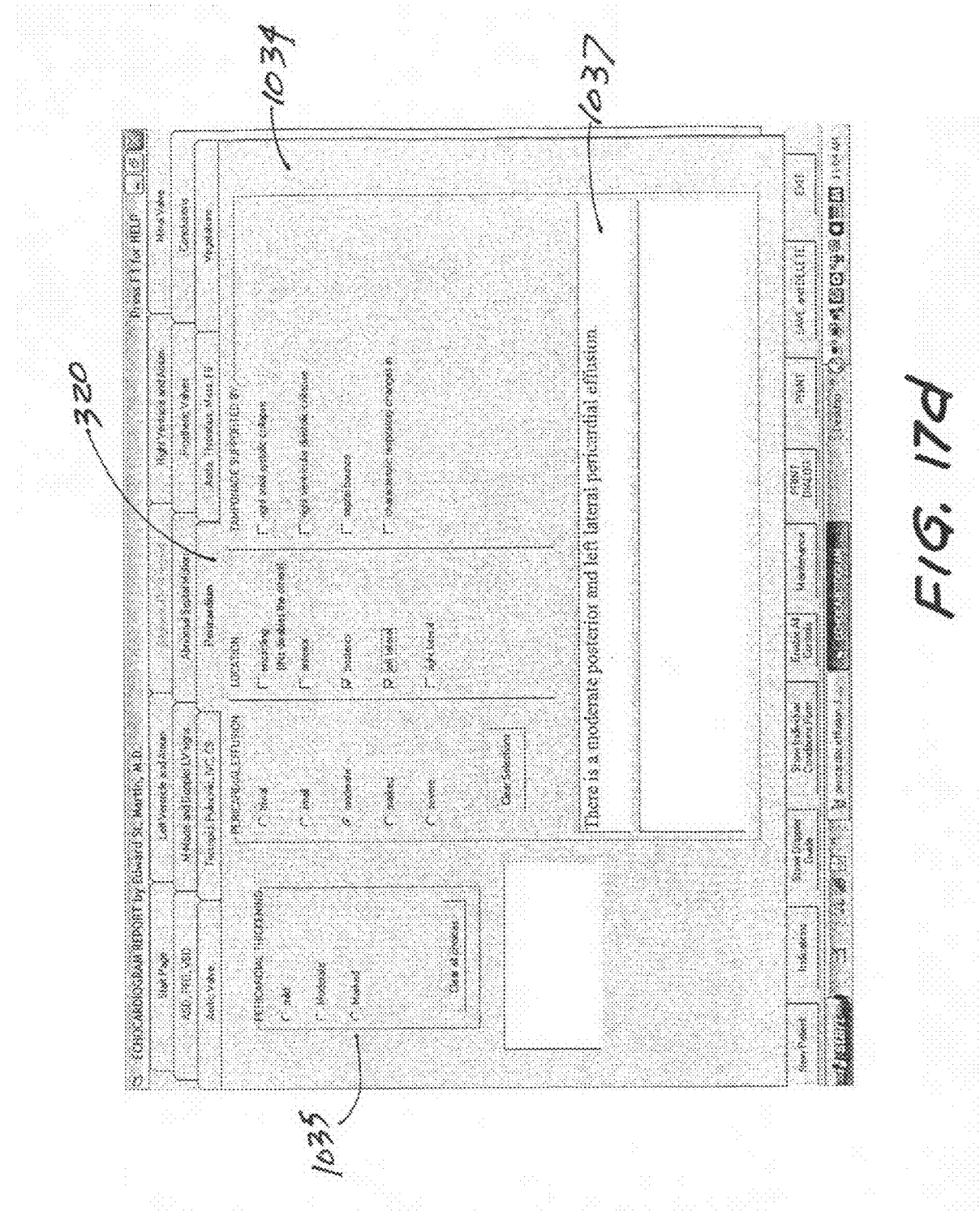

FIGS. 17a through 17d are all screen pages 1034 opened by clicking on the "Pericardium" tab 320 on the start-up screen page 301, and as also shown in FIG. 10j. In FIG. 17a, no option boxes 1035 were selected and the text box 1037 says simply, "There is no pericardial effusion." As illustrated further in FIGS. 17b through 17d, the selection of various option boxes 1035 automatically changes the text box 1037 with the generation of a complete grammatically complex sentence in response to the option boxes selected.

Figure 18A:
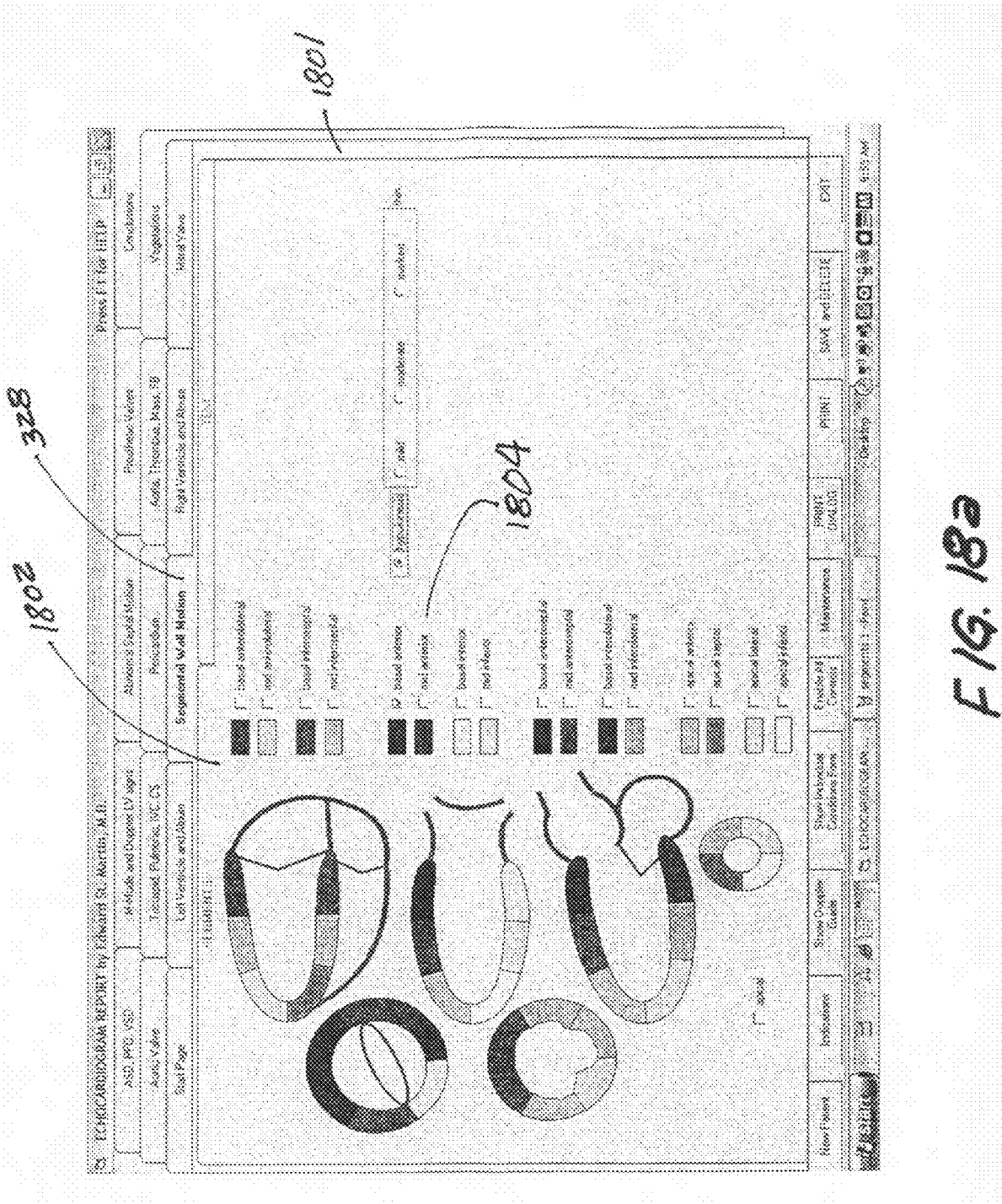
Figure 18B:
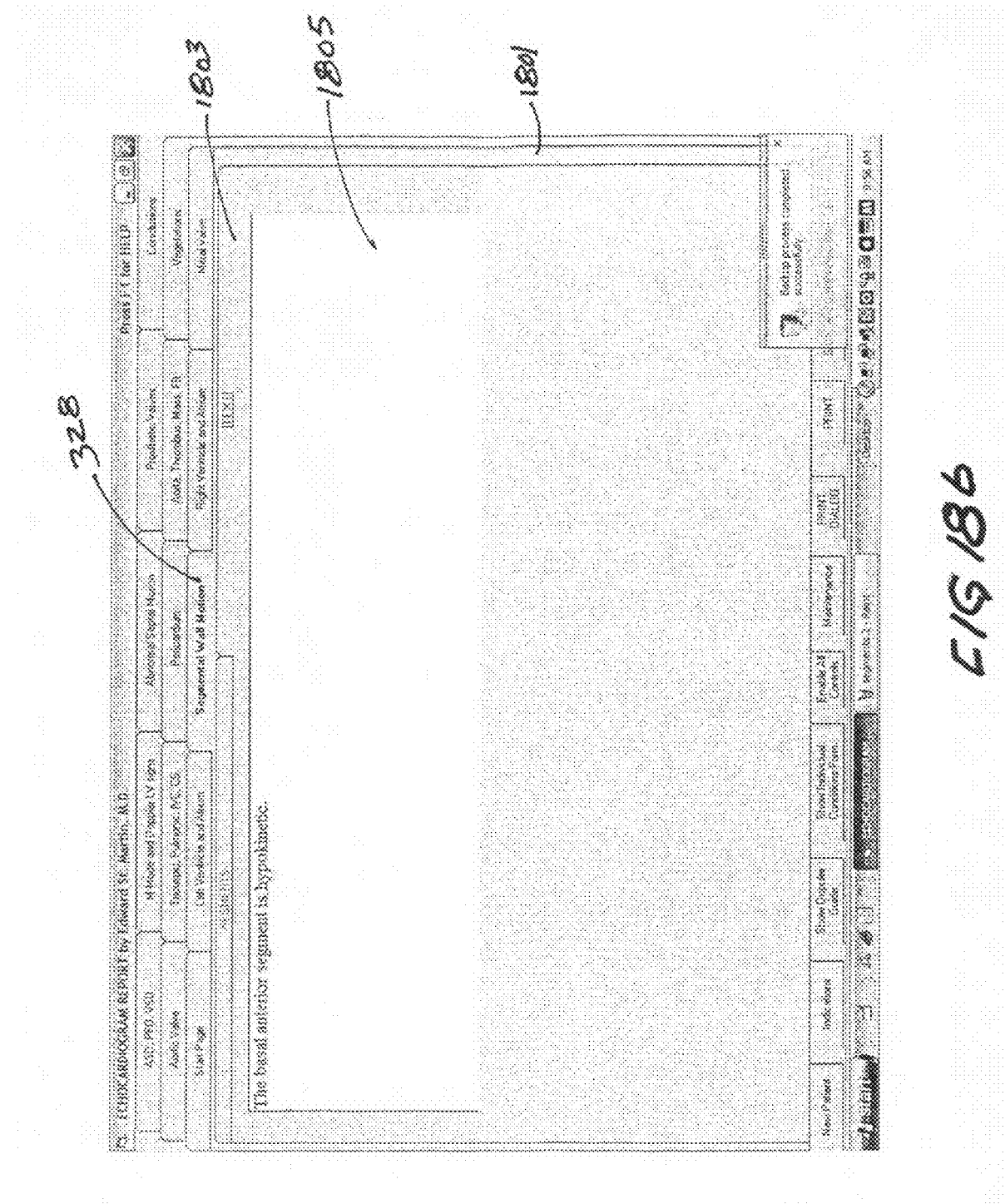
Figure 18C:
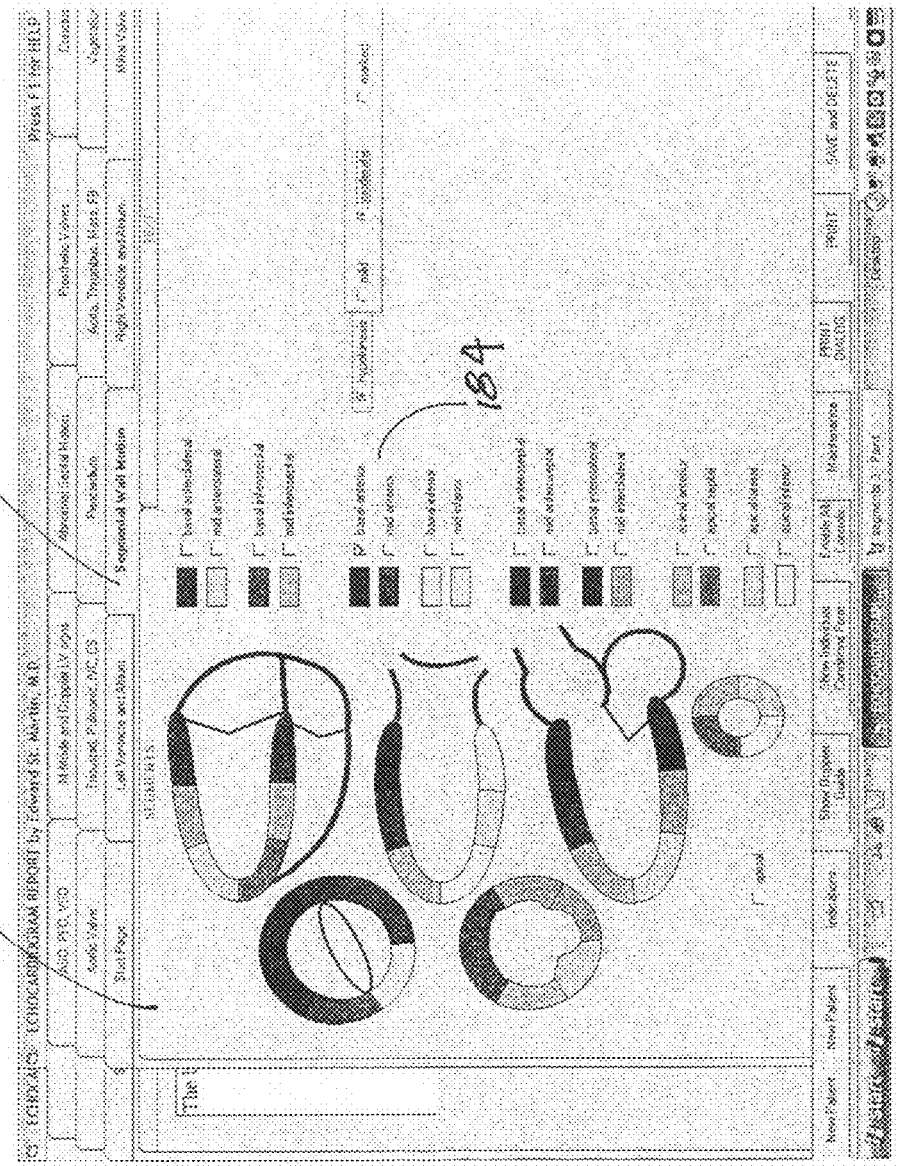
Figure 18D:
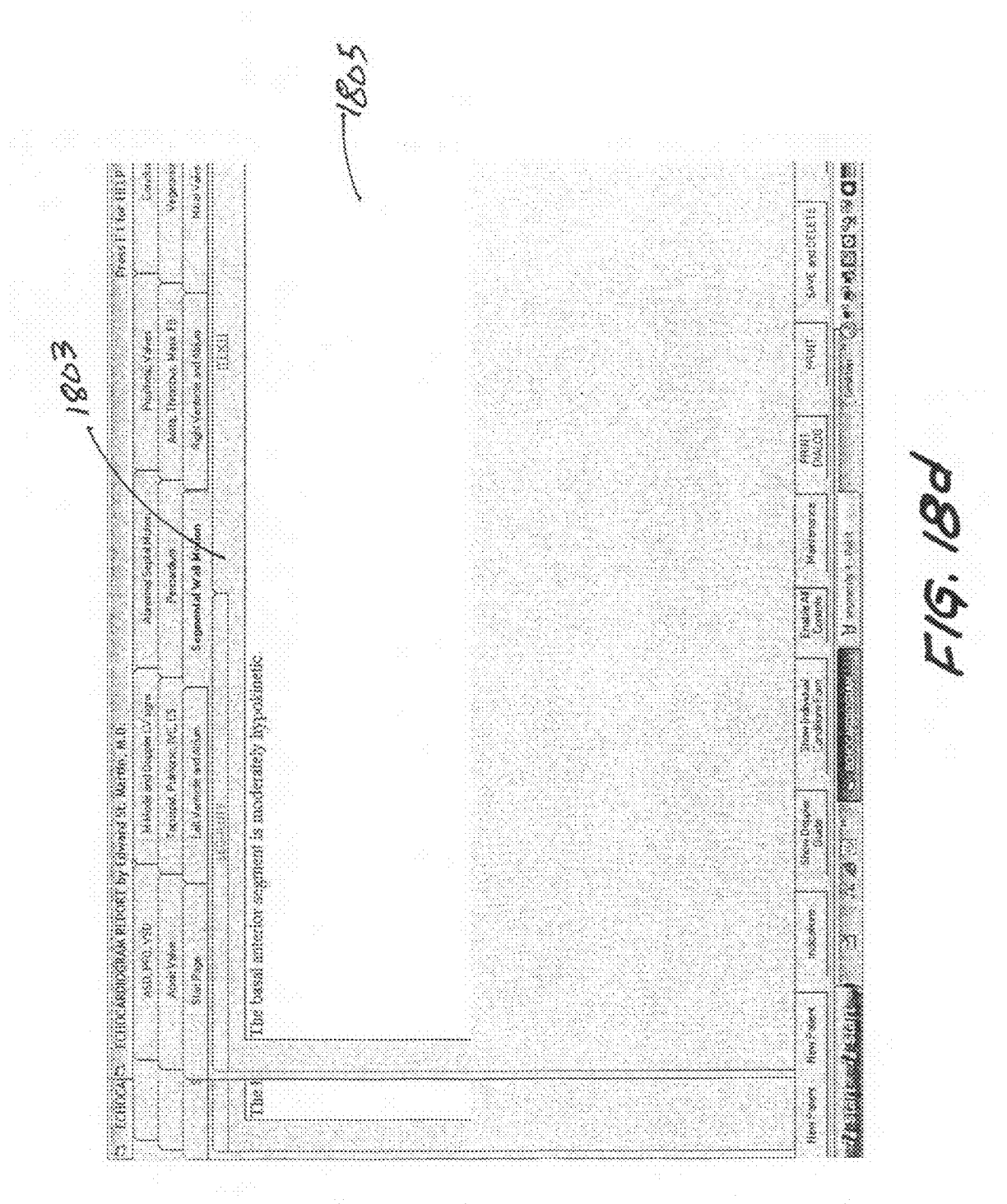
Figure 18E:
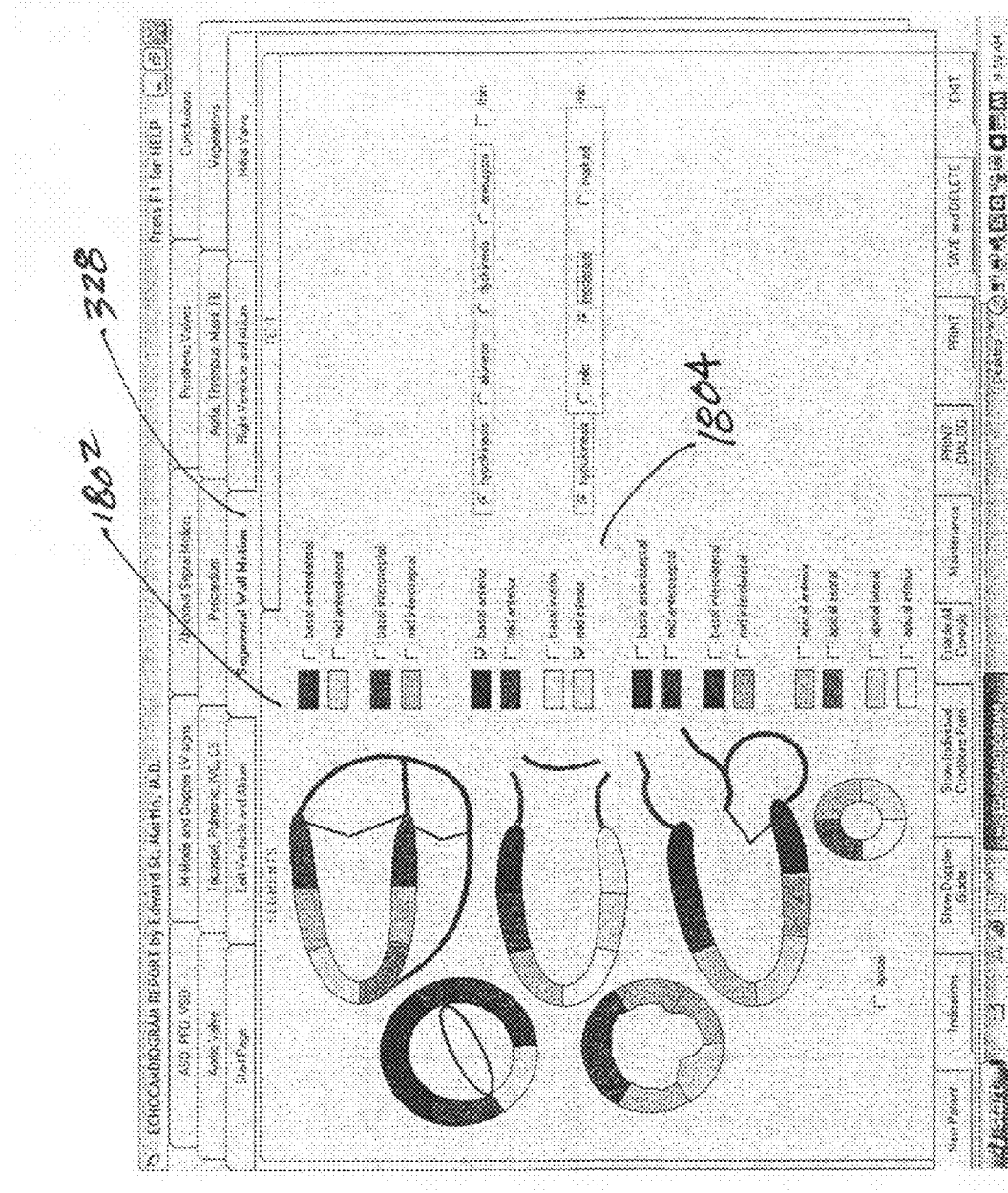
Figure 18F:
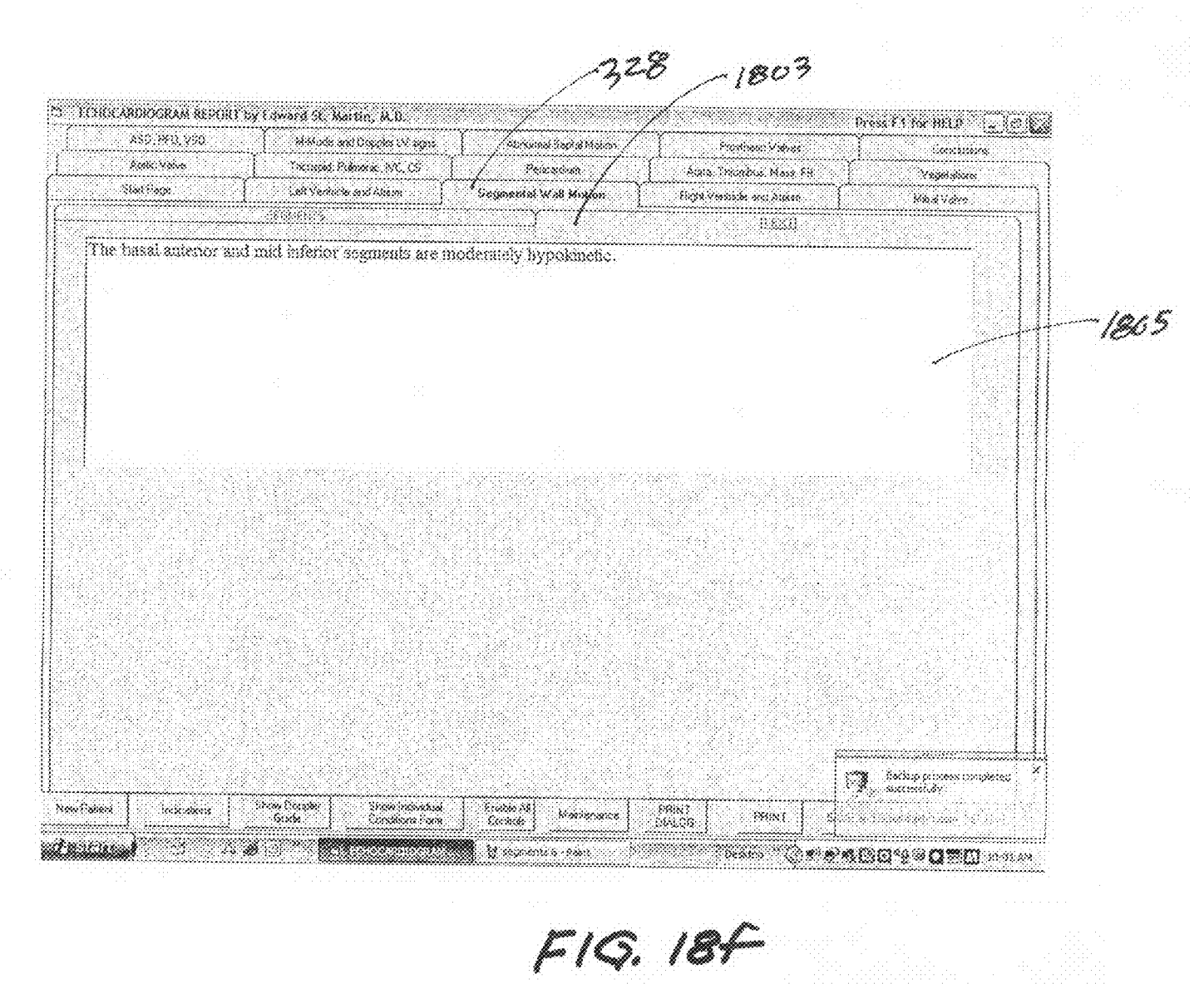

FIGS. 18a through 18f are all screen pages 1801 opened by clicking on the "Segmental Wall Motion" tab 328 on the start-up screen page 301. FIGS. 18a, 18c, and 18e are opened by clicking on the "Segments" tab 1802, and FIGS. 18b, 18d and 18e are opened by clicking on the "Text" tab 1803. Selection of the option boxes 1804 on FIGS. 18a, 18c, and 18e, generates complete grammatically complex sentences in the text boxes 1805 on FIGS. 18b, 18d and 18f in response to the option boxes selected.

Figure 19:
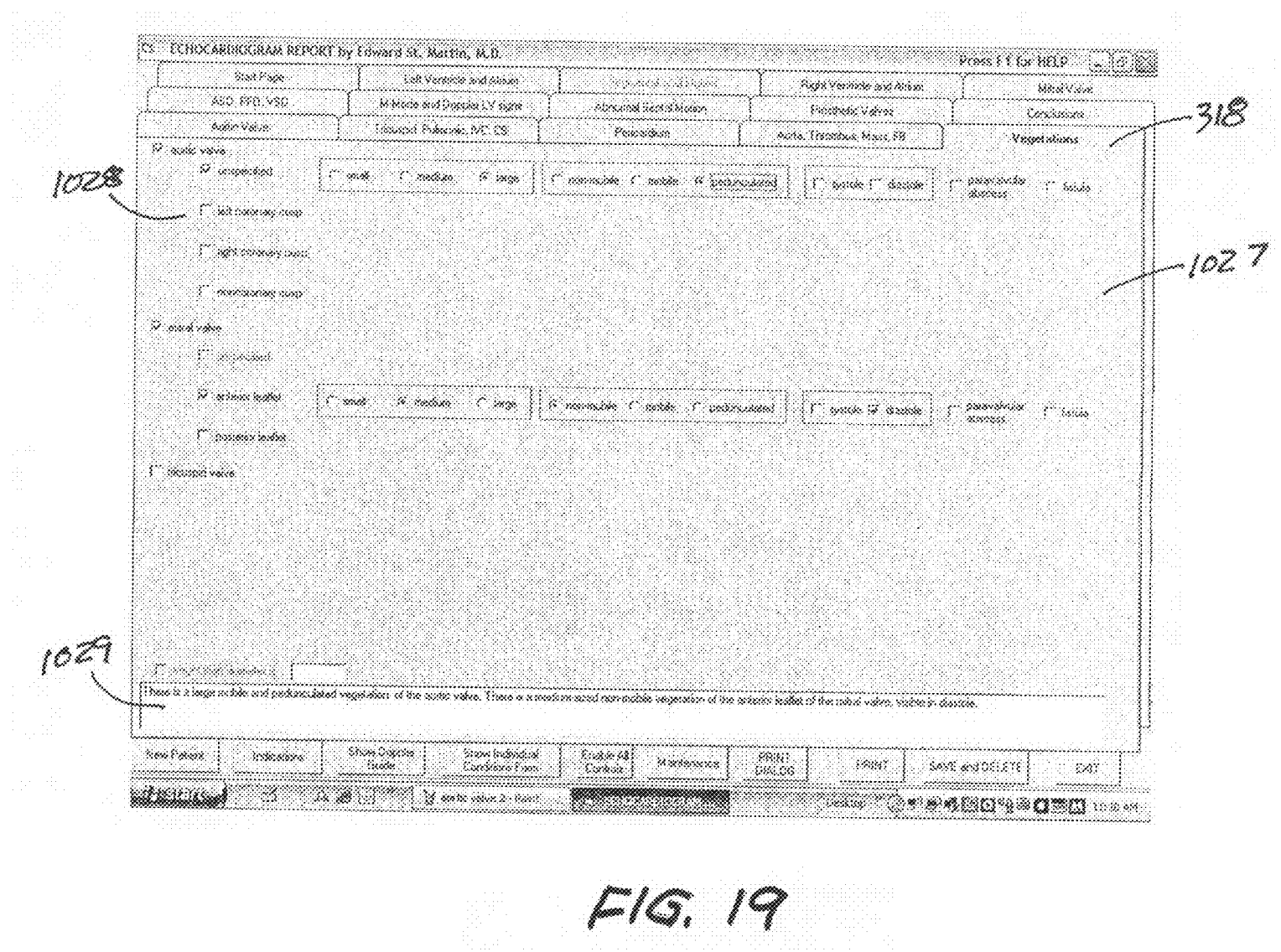

FIG. 19 is a screen page 1027 opened by clicking on the "Vegetations" tab 318 on the start-up screen 301. Selection of several option boxes 1028 automatically generates complete grammatically complex sentences in the text box 1029. In this case, the text box reads, "There is a large mobile and pedunculated vegetation of the aortic valve. There is a medium-sized non-mobile vegetation of the anterior leaflet of the mitral valve, visible in diastole."

I claim:

1. A computer-implemented method of generating a medical report describing an echocardiogram without dictation, transcription or typing, comprising the steps of:

creating at least one database comprising echocardiogram measurements for at least one patient;

providing a user with a prompting graphical user interface to log in and gain access to said database and the echocardiogram measurements for a patient;

providing the user with a start-up graphical user interface for display of echocardiogram measurements for the patient, said start-up graphical user interface having a plurality of tabbed anatomical-based graphical user interfaces pertaining to specific anatomical parts of a human heart for entry in option boxes of a diagnosis by the user pertaining to any of said anatomical parts of the human heart based upon the echocardiogram measurements for the patient available in said data base, and entry in the option boxes by the user of a diagnosis pertaining to any of said anatomical parts of the human heart based upon the echocardiogram measurements for the patient available in said data base;

wherein the plurality of tabbed anatomical-based graphical user interfaces pertaining to specific anatomical parts of a human heart comprises a graphical user interface for the aortic valve, a graphical user interface for the left ventricle and left atrium, a graphical user interface for the right ventricle and right atrium, a graphical user interface for the mitral valve, a graphical user interface for the tricuspid valve, the pulmonic valve and the inferior vena cava, a graphical user interface for the pericardium, a graphical user interface for the aorta, thrombus and foreign bodies, a graphical user interface for vegetations, a graphical user interface for atrial septal defect, patent foramen ovale and ventricular septal defect, a graphical user interface for M-mode and Doppler left ventricular signs; a graphical user interface for abnormal septal motion, a graphical user interface for prosthetic valves, and a graphical user interface for segmental wall motion;

providing the user with a plurality of disease-based graphical user interfaces pertaining to disease states of the human heart accessible from the anatomical-based graphical user interfaces to assist the user in the entry in option boxes of a diagnosis by the user pertaining to any of the specific anatomical parts of the human heart based upon the echocardiogram measurements for the patient available in said data base, and entry in the option boxes by the user of a diagnosis pertaining to any of the specific anatomical parts of the human heart based upon the echocardiogram measurements for the patient available in said data base;

wherein the plurality of disease-based graphical user interfaces pertaining to disease states of the human heart comprises a graphical user interface for cardiac source of emboli, a graphical user interface for diastolic analysis, a graphical user interface for myxoma, a graphical user interface for restrictive cardiomyopathy, a graphical user interface for aortic dissection, a graphical user interface for infective endocarditis, a graphical user interface for dilated cardiomyopthy, a graphical user interface for hypertropic cardiomyopathy, and a graphical user interface for myocardial infarction;

generating complete sentences including complex sentences, in response to the entry in the option boxes of diagnosis by the user pertaining to any of the specific anatomical parts of the human heart based upon the echocardiogram measurements for the patient available in said data base without dictation, transcription or typing generating complete sentences including complex sentences in response to the entry of diagnoses by the user pertaining to any of the disease states of the human heart based upon the echocardiogram measurements for the patient available in said data base, without dictation, transcription or typing providing the user with a graphical user interface to create a medical report for an individual patient in complete sentences including complex sentences in response to the entry of diagnoses by the user without dictation, transcription or typing;

generating a medical report for an individual patient in complete sentences including complex sentences in response to the entry of diagnoses by the user without dictation, transcription or typing.

2. The computer-implemented method of claim 1 wherein the plurality of tabbed anatomical-based graphical user interfaces pertaining to specific anatomical parts of a human heart further comprises at least one graphical user interface illustrating a diagram of wall segments of the human heart.

3. The computer-implemented method of claim 2 further comprising providing the user with a graphical user interface for comparison of prior echocardiogram measurements of a patient with current echocardiogram measurements for that patient.

4. The computer-implemented method of claim 3 further comprising providing the user with a graphical user interface providing a reference list of Medicare approved indications for echocardiograms and respective ICD-9 codes.

5. A tangible computer-readable storage medium for use with a graphics display device bearing program code for instructing a computer to perform a method of generating a medical report describing an echocardiogram for a patient without dictation, transcription or typing, said method comprising;

creating at least one database comprising echocardiogram measurements for at least one patient;

providing a user with a prompting graphical user interface to log in and gain access to said database and the echocardiogram measurements for a patient;

providing the user with a start-up graphical user interface for display of echocardiogram measurements for the patient, said start-up graphical user interface having a plurality of tabbed anatomical-based graphical user interfaces pertaining to specific anatomical parts of a human heart for entry in option boxes of a diagnosis by the user pertaining to any of said anatomical parts of the human heart based upon the echocardiogram measurements for the patient available in said data base and entry in option boxes by the user of a diagnosis pertaining to any of said anatomical parts of the human heart based upon the echocardiogram measurements for the patient available in said data base;

wherein the plurality of tabbed anatomical-based graphical user interfaces pertaining to specific anatomical parts of a human heart comprises a graphical user interface for the aortic valve, a graphical user interface for the left ventricle and left atrium, a graphical user interface for the right ventricle and right atrium, a graphical user interface for the mitral valve, a graphical user interface for the tricuspid valve, the pulmonic valve and the inferior vena cava, a graphical user interface for the pericardium, a graphical user interface for the aorta, thrombus and foreign bodies, a graphical user interface for vegetations, a graphical user interface for atrial septal defect, patent foramen ovale and ventricular septal defect, a graphical user interface for M-mode and Doppler left ventricular signs; a graphical user interface for abnormal septal motion, a graphical user interface for prosthetic valves, and a graphical user interface for segmental wall motion;

providing the user with a plurality of disease-based graphical user interfaces pertaining to disease states of the human heart accessible from the anatomical-based graphical user interfaces to assist the user in the entry in option boxes of a diagnosis by the user pertaining to any of the specific anatomical parts of the human heart based upon the echocardiogram measurements for the patient available in said data base and entry in option boxes by the user of a diagnosis pertaining to any of the specific anatomical parts of the human heart based upon the echocardiogram measurements for the patient available in said data base;

wherein the plurality of disease-based graphical user interfaces pertaining to disease states of the human heart comprises a graphical user interface for cardiac source of emboli, a graphical user interface for diastolic analysis, a graphical user interface for myxoma, a graphical user interface for restrictive cardiomyopathy, a graphical user interface for aortic dissection, a graphical user interface for infective endocarditis, a graphical user interface for dilated cardiomyopthy, a graphical user interface for hypertropic cardiomyopathy, and a graphical user interface for myocardial infarction;

generating complete sentences including complex sentences, in response to the entry of diagnosis by the user pertaining to any of the specific anatomical parts of the human heart based upon the echocardiogram measurements for the patient available in said data base without dictation, transcription or typing generating complete sentences including complex sentences, in response to the entry of diagnosis by the user pertaining to any of the disease states of the human heart based upon the echocardiogram measurements for the patient available in said data base without dictation, transcription or typing;

providing the user with a graphical user interface to create a medical report for an individual patient in complete sentences including complex sentences, based on the entry of diagnoses by the user without dictation, transcription or typing;

generating a medical report for an individual patient in complete sentences including complex sentences, based on the entry of diagnoses by the user without dictation, transcription or typing.

6. The computer-readable storage medium of claim 5, wherein the provided plurality of tabbed anatomical-based graphical user interfaces pertaining to specific anatomical parts of a human heart further comprises at least one graphical user interface illustrating a diagram of wall segments of the human heart.

7. The computer-readable storage medium of claim 6 wherein the instructed method further comprises providing the user with a graphical user interface for comparison of prior echocardiogram measurements of a patient with current echocardiogram measurements for that patient.

8. The computer-readable storage medium of claim 7 wherein the instructed method further comprises providing the user with a graphical user interface providing a reference list of Medicare approved indications for echocardiograms and respective ICD-9 codes.

* * * * *